US007445917B2

(12) United States Patent
DiCosimo et al.

(10) Patent No.: US 7,445,917 B2
(45) Date of Patent: Nov. 4, 2008

(54) PROCESS FOR PRODUCING GLYCOLIC ACID FROM FORMALDEHYDE AND HYDROGEN CYANIDE

(75) Inventors: Robert DiCosimo, Chadds Ford, PA (US); Anna Panova, Hockessin, DE (US); Jeffery Scott Thompson, West Chester, PA (US); Robert D. Fallon, Elkton, MD (US); F. Glenn Gallagher, Wilmington, DE (US); Thomas Foo, Wilmington, DE (US); Xu Li, Newark, DE (US); George C. Fox, Wilmington, DE (US); Joseph J. Zaher, Newark, DE (US); Mark S. Payne, Wilmington, DE (US); Daniel P. O'Keefe, Ridley Park, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 85 days.

(21) Appl. No.: 11/314,905

(22) Filed: Dec. 21, 2005

(65) Prior Publication Data

US 2006/0247467 A1 Nov. 2, 2006

Related U.S. Application Data

(60) Provisional application No. 60/638,168, filed on Dec. 22, 2004, provisional application No. 60/638,148, filed on Dec. 22, 2004, provisional application No. 60/638,176, filed on Dec. 22, 2004, provisional application No. 60/638,127, filed on Dec. 22, 2004, provisional application No. 60/638,128, filed on Dec. 22, 2004, provisional application No. 60/638,126, filed on Dec. 22, 2004.

(51) Int. Cl.

| | |
|---|---|
| ***C12P 21/06*** | (2006.01) |
| ***C12N 9/80*** | (2006.01) |
| ***C12N 1/20*** | (2006.01) |
| ***C12N 1/19*** | (2006.01) |
| ***C12N 15/74*** | (2006.01) |
| ***C07H 21/04*** | (2006.01) |

(52) U.S. Cl. .................... 435/146; 435/228; 435/252.3; 435/254.2; 435/471; 435/483; 536/23.2

(58) Field of Classification Search ................ 435/69.1, 435/228, 252.3, 254.2, 471, 483; 536/23.2
See application file for complete search history.

(56) References Cited

U.S. PATENT DOCUMENTS

| | | | | |
|---|---|---|---|---|
| 2,175,805 | A | 10/1939 | Jacobson | |
| 2,565,569 | A * | 8/1951 | McCants | 549/352 |
| 2,890,238 | A | 6/1959 | Sexton | |
| 3,940,316 | A | 2/1976 | Commeyras et al. | |
| 5,187,301 | A | 2/1993 | Cullen et al. | |
| 5,223,416 | A | 6/1993 | Endo et al. | |
| 5,234,826 | A | 8/1993 | Yamagami et al. | |
| 5,296,373 | A | 3/1994 | Endo et al. | |
| 5,326,702 | A | 7/1994 | Endo et al. | |
| 5,508,181 | A | 4/1996 | Hashimoto | |
| 5,756,306 | A | 5/1998 | Yamaguchi et al. | |
| 5,858,736 | A | 1/1999 | Di Cosimo et al. | |
| 5,922,589 | A | 7/1999 | Di Cosimo et al. | |
| 6,037,155 | A | 3/2000 | Kobayashi et al. | |
| 6,251,650 | B1 | 6/2001 | Fallon et al. | |
| 6,291,708 | B1 | 9/2001 | Cockrem | |
| 6,383,786 | B1 | 5/2002 | Chauhan et al. | |
| 6,416,980 | B1 | 7/2002 | Chauhan et al. | |
| 6,870,038 | B2 | 3/2005 | Chauhan et al. | |
| 7,148,051 | B2 * | 12/2006 | Payne et al. | 435/227 |
| 2004/0194810 | A1 * | 10/2004 | Strothoff et al. | 134/25.2 |
| 2004/0210087 | A1 | 10/2004 | Meng et al. | |

FOREIGN PATENT DOCUMENTS

| | | | |
|---|---|---|---|
| EP | 0 546 049 | B1 | 7/1995 |
| EP | 0 666 320 | A2 | 8/1995 |
| EP | 0 610 048 | B1 | 9/1999 |
| JP | 1986/056086 | A | 3/1986 |
| JP | 1997/028390 | A | 2/1997 |
| WO | WO 93/24631 | A1 | 12/1993 |
| WO | WO 01/75077 | A2 | 10/2001 |
| WO | WO 02/068658 | A1 | 9/2002 |
| WO | WO 2005/106005 | A1 | 11/2005 |

OTHER PUBLICATIONS

Su et al. Catalytic dehydrogenation of methanol to water-free formaldehyde, Chem. Eng. Technol. 17 (1994), 34-40.*
U.S. Appl. No. 60/638,148, filed Dec. 22, 2004, Li et al.
U.S. Appl. No. 60/638,126, filed Dec. 22, 2004, F. Glenn Gallagher.
U.S. Appl. No. 60/638,127, filed Dec. 22, 2004, Thomas Foo.
U.S. Appl. No. 10/919,182, filed Aug. 16, 2004, Payne et al.
U.S. Appl. No. 60/638,176, filed Dec. 22, 2004, Di Cosimo et al.
U.S. Appl. No. 60/638,128, filed Dec. 22, 2004, Xu Li.
U.S. Appl. No. 10/977,893, filed Oct. 29, 2004, Payne et al.
Shijun Wu et al., Cloning and Nucleotide Sequence of Amidase Gene From *Pseudomonas putida*, DNA and Cell Biology, vol. 17(10):915-920, 1998.
I. Inci, Distribution of Glycolic Acid Between Water and Different Organic Solutions, Chem. Biochem. Eng. Q., vol. 16(2):81-85, 2002.
David T. Mowry, The Preparation of Nitriles, Chemical Reviews, vol. 42:189-283, 1948.
Michihiko Kobayashi et al., Amidase Couple With Low-Molecular-Mass Nitrile Hydratase From *Rhodococcus rhodochrous* J1, Eur. J. Biochem., vol. 217:327-336, 1993.

(Continued)

*Primary Examiner*—Rebecca E. Prouty

*Assistant Examiner*—Iqbal H Chowdhury

(57) ABSTRACT

A process is provided for producing glycolic acid from formaldehyde and hydrogen cyanide. More specifically, heat-treated formaldehyde and hydrogen cyanide are reacted to produce glycolonitrile having low concentrations of impurities. The glycolonitrile is subsequently converted to an aqueous solution of ammonium glycolate using an enzyme catalyst having nitrilase activity derived from *Acidovorax facilis* 72W (ATCC 57746). Glycolic acid is recovered in the form of the acid or salt from the aqueous ammonium glycolate solution using a variety of methods described herein.

25 Claims, 7 Drawing Sheets

OTHER PUBLICATIONS

Li Feng et al., High-Level Expression and Mutagenesis of Recombinant Human Phosphatidylcholine Transfer Protein Using a Synthetic Gene: Evidence for a C-Terminal Membrane Binding Domain, Biochemistry, vol. 39:15399-15409, 2000.

Janet A. Tamada et al., Extraction of Carboxylic Acids With Amine Extractants. 1. Equilibria and Law of Mass Action Modeling, Ind. Eng. Chem. Res., vol. 29:1319-1326, 1990.

Janet A. Tamada et al., Extraction of Carboxylic Acids With Amine Extractants. 2. Chemical Interactions and Interpretation of Data, Ind. Eng. Chem. Res., vol. 29:1327-1333, 1990.

D. Tourneix et al., Regulation of Nitrile-Hydratase Synthesis in a *Brevibacterium* Species, Antonie Van Leeuwenhoek, vol. 52:173-182, 1986.

Yasuhisa Asano et al., Aliphatic Nitrile Hydratase From *Arthrobacter* Sp. J-1 Purification and Characterization, Agric. Biol. Chem., vol. 46(5):1165-1174, 1982.

Ismail Inci et al., Extraction of Glycolic Acid From Aqueous Solutions by Trioctyl Methylammonium Chloride and Organic Solvents, J. Chem. Eng. Data, vol. 50:536-540, 2005.

Mukund V. Deshpande, Ethanol Production From Cellulose by Coupled Saccharification/Fermentation Using *Saccharomyces cerevisiae* and Cellulase Complex From *Sclerotium rolfsii* UV-8 Mutant, Applied Biochemistry and Biotechnology, vol. 36:227-234, 1992.

Kailas L. Wasewar et al., Reactive Extraction of Lactic Acid Using Alamine 336 in MIBK: Equilibria and Kinetics, Journal of Biotechnology, vol. 97:59-68, 2002.

Nikolay S. Outchkourov et al., Optimization of the Expression of Equistatin in *Pichia pastoris*, Protein Expression and Purification, vol. 24:18-24, 2002.

S. Chauhan et al., Purification, Cloning, Sequencing, and Over-Expression in *Escherichia coli* of a Regioselective Aliphatic Nitrilase From *Acidovorax facilis* 72W, Appl. Microbiol. Biotechnol., vol. 61:118-122, 2003.

S. Azza et al., Cloning of the Wide Spectrum Amidase Gene From *Brevibacterium* Sp. R312 by Genetic Complementation. Overexpression in *Brevibacterium* Sp. and *Escherichia coli*, FEMS Microbiology Letters, vol. 122:129-136, 1994.

Methods in Biotechnology, vol. 1: Immobilization of Enzymes and Cells; Gordon F. Bickerstaff, Editor; Humana Press, Totowa, NJ, US; 1997 (Book Not Supplied).

Recombinant Microbes for Industrial and Agricultural Applications, Murooka et al., Eds., Marcel Dekker, Inc., New York, NY 1994 (Book Not Supplied).

Thomas D. Brock in Biotechnology: A Textbook of Industrial Microbiology, Second Edition, 1989, Sinauer Associates, Inc., Sunderland, Ma (Book Not Supplied).

Perry's Chemical Engineer's Handbook, 7th Ed., Perry, Robert H., et al., McGraw Hill Companies, Inc. New York, NY, 1997 (Book Not Supplied).

Perry's Chemical Engineers' Handbook, 7th Ed., Perry, Robert H. et al., Chapter 14.23 Through 14.61, McGraw Hill Companies, Inc., New York, NY, 1997 (Book Not Supplied).

Manual of Methods for General Bacteriology, 1994, Phillipp Gerhardt et al., Eds., American Society for Microbiology, Washington, DC. (Book Not Supplied).

T. J. Silhavy et al., Experiments With Gene Fusions, 1984 Cold Spring Harbor Laboratory Press, Cold Spring, NY (Book Not Supplied).

F. M. Ausubel et al., Current Protocols in Molecular Biology, 1994-1998, John Wiley & Sons, Inc., New York (Book Not Supplied).

International Search Report Dated Jun. 28, 2006, International Application No. PCT/US2005/046273, International Filing Date: Dec. 21, 2005.

Helen C. Pace et al., The nitrilase superfamily: classification, structure and function, Genome Biology, vol. 2, No. 1, 2001.

Don Cowan et al., Biochemistry and biotechnology of mesophilic and thermophilic nitrile metabolizing enzymes, Extremophiles 2:207-216, 1998.

* cited by examiner

SEQUENCE LISTING

```
<160> NUMBER OF SEQ ID NOS: 39

<210> SEQ ID NO 1
<211> LENGTH: 49
<212> TYPE: DNA
<213> ORGANISM: artificial sequence
<220> FEATURE:
<223> OTHER INFORMATION: Primer
```

-continued

<400> SEQUENCE: 1
cgactgcagt aaggaggaat aggacatggt ttcgtataac agcaagttc 49

<210> SEQ ID NO 2
<211> LENGTH: 40
<212> TYPE: DNA
<213> ORGANISM: artificial sequence
<220> FEATURE:
<223> OTHER INFORMATION: Primer

<400> SEQUENCE: 2
tgatctagag cttggagaat aaaggggaag accagagatg 40

<210> SEQ ID NO 3
<211> LENGTH: 31
<212> TYPE: DNA
<213> ORGANISM: artificial sequence
<220> FEATURE:
<223> OTHER INFORMATION: Primer

<400> SEQUENCE: 3
gcgcatatgg tttcgtataa cagcaagttc c 31

<210> SEQ ID NO 4
<211> LENGTH: 32
<212> TYPE: DNA
<213> ORGANISM: artificial sequence
<220> FEATURE:
<223> OTHER INFORMATION: Primer

<400> SEQUENCE: 4
ataggatcct tatggctact ttgctgggac cg 32

<210> SEQ ID NO 5
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 5

```
atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110
```

-continued

```
ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys


<210> SEQ ID NO 6
<211> LENGTH: 369
<212> TYPE: PRT
<213> ORGANISM: Acidovorax facilis 72W

<400> SEQUENCE: 6

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
```

-continued

```
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 7
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 7

```
atg gtt tcg tat aac agc aag ttc ctc gcg gca acc gtt cag gca gag       48
```

-continued

```
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa cag agc atc gaa gcc aac gcg acg      624
Pro Leu Gln Pro Asp Val Phe Gln Gln Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320
```

-continued

```
gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
        355                 360                 365

aag tag                                                              1110
Lys


<210> SEQ ID NO 8
<211> LENGTH: 369
<212> TYPE: PRT
<213> ORGANISM: Acidovorax facilis 72W

<400> SEQUENCE: 8

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Gln Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300
```

-continued

```
Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 9
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 9

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa gct agc atc gaa gcc aac gcg acg      624
Pro Leu Gln Pro Asp Val Phe Gln Ala Ser Ile Glu Ala Asn Ala Thr
        195                 200                 205

gtc acc cgc tcg tac gca atc gaa ggc caa acc ttt gtg ctt tgc tcg      672
```

-continued

```
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys


<210> SEQ ID NO 10
<211> LENGTH: 369
<212> TYPE: PRT
<213> ORGANISM: Acidovorax facilis 72W

<400> SEQUENCE: 10

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160
```

-continued

```
Gly Leu Asn Cys Trp Glu His Phe Gln Pro Leu Ser Lys Phe Met Met
            165                 170                 175

Tyr Ser Leu Gly Glu Gln Val His Val Ala Ser Trp Pro Ala Met Ser
        180                 185                 190

Pro Leu Gln Pro Asp Val Phe Gln Ala Ser Ile Glu Ala Asn Ala Thr
    195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
            245                 250                 255

Gly Pro Asp Gly Ser Glu Leu Ala Lys Pro Leu Ala Glu Asp Ala Glu
        260                 265                 270

Gly Ile Leu Tyr Ala Glu Ile Asp Leu Glu Gln Ile Leu Leu Ala Lys
    275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
            325                 330                 335

Leu Arg Gln Ala Ala Glu Gln Glu Arg Gln Ala Ser Lys Arg Leu Gly
        340                 345                 350

Thr Lys Leu Phe Glu Gln Ser Leu Leu Ala Glu Glu Pro Val Pro Ala
    355                 360                 365

Lys


<210> SEQ ID NO 11
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 11

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
```

-continued

```
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa tgt agc atc gaa gcc aac gcg acg      624
Pro Leu Gln Pro Asp Val Phe Gln Cys Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys
```

```
<210> SEQ ID NO 12
<211> LENGTH: 369
<212> TYPE: PRT
<213> ORGANISM: Acidovorax facilis 72W

<400> SEQUENCE: 12

Met Val Ser Tyr Asn Ser Lys Phe Leu Ala Ala Thr Val Gln Ala Glu
1               5                   10                  15
```

-continued

```
Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Cys Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 13
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 13
```

-continued

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190

cct ctt cag ccg gat gtt ttc caa acc agc atc gaa gcc aac gcg acg     624
Pro Leu Gln Pro Asp Val Phe Gln Thr Ser Ile Glu Ala Asn Ala Thr
        195                 200                 205

gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag     816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag     864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att     960
Val Gln Phe Asp Pro Arg Asn His Thr Pro Val His Arg Ile Gly Ile
```

-continued

```
305                 310                 315                 320

gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
            325                 330                 335

ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
        355                 360                 365

aag tag                                                              1110
Lys


<210> SEQ ID NO 14
<211> LENGTH: 369
<212> TYPE: PRT
<213> ORGANISM: Acidovorax facilis 72W

<400> SEQUENCE: 14

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
            85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
            165                 170                 175

Tyr Ser Leu Gly Glu Gln Val His Val Ala Ser Trp Pro Ala Met Ser
            180                 185                 190

Pro Leu Gln Pro Asp Val Phe Gln Thr Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
            245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285
```

-continued

```
Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 15
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 15

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa gga agc atc gaa gcc aac gcg acg      624
Pro Leu Gln Pro Asp Val Phe Gln Gly Ser Ile Glu Ala Asn Ala Thr
        195                 200                 205
```

-continued

```
gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys


<210> SEQ ID NO 16
<211> LENGTH: 369
<212> TYPE: PRT
<213> ORGANISM: Acidovorax facilis 72W

<400> SEQUENCE: 16

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140
```

-continued

```
Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Gly Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 17
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 17

atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95
```

-continued

```
atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa cac agc atc gaa gcc aac gcg acg      624
Pro Leu Gln Pro Asp Val Phe Gln His Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys
```

<210> SEQ ID NO 18
<211> LENGTH: 369
<212> TYPE: PRT
<213> ORGANISM: Acidovorax facilis 72W

<400> SEQUENCE: 18

-continued

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln His Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 19
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

-continued

<400> SEQUENCE: 19

```
atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa aag agc atc gaa gcc aac gcg acg      624
Pro Leu Gln Pro Asp Val Phe Gln Lys Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300
```

-continued

```
gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys


<210> SEQ ID NO 20
<211> LENGTH: 369
<212> TYPE: PRT
<213> ORGANISM: Acidovorax facilis 72W

<400> SEQUENCE: 20

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Lys Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
```

-continued

```
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 21
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 21

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa aat agc atc gaa gcc aac gcg acg      624
```

-continued

```
Pro Leu Gln Pro Asp Val Phe Gln Asn Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys


<210> SEQ ID NO 22
<211> LENGTH: 369
<212> TYPE: PRT
<213> ORGANISM: Acidovorax facilis 72W

<400> SEQUENCE: 22

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
```

-continued

```
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Asn Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 23
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 23

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
```

-continued

```
                85                  90                  95

atc gca ctc gtc atg ggc tat tcg gag cgg gaa gcc gga tcg cgc tat        336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg        384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc        432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt        480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg        528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc        576
Tyr Ser Leu Gly Glu Gln Val His Val Ala Ser Trp Pro Ala Met Ser
            180                 185                 190

cct ctt cag ccg gat gtt ttc caa tct agc atc gaa gcc aac gcg acg        624
Pro Leu Gln Pro Asp Val Phe Gln Ser Ser Ile Glu Ala Asn Ala Thr
        195                 200                 205

gtc acc cgc tcg tac gca atc gaa ggc caa acc ttt gtg ctt tgc tcg        672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac        720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac        768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
        355                 360                 365

aag tag                                                               1110
Lys
```

<210> SEQ ID NO 24
<211> LENGTH: 369
<212> TYPE: PRT
<213> ORGANISM: Acidovorax facilis 72W -continued

<400> SEQUENCE: 24

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Ser Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 25
<211> LENGTH: 1110
<212> TYPE: DNA
<213> ORGANISM: Acidovorax facilis 72W
<220> FEATURE:

-continued

```
<221> NAME/KEY: CDS
<222> LOCATION: (1)..(1110)

<400> SEQUENCE: 25

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat aaa caa ccg ctc agc aag ttc atg atg      528
Gly Leu Asn Cys Trp Glu His Lys Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
```

-continued

```
290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys


<210> SEQ ID NO 26
<211> LENGTH: 369
<212> TYPE: PRT
<213> ORGANISM: Acidovorax facilis 72W

<400> SEQUENCE: 26

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Lys Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270
```

-continued

```
Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 27
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 27

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat atg caa ccg ctc agc aag ttc atg atg      528
Gly Leu Asn Cys Trp Glu His Met Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190
```

-continued

```
cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys
```

<210> SEQ ID NO 28
<211> LENGTH: 369
<212> TYPE: PRT
<213> ORGANISM: Acidovorax facilis 72W

<400> SEQUENCE: 28

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125
```

-continued

```
Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Met Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 29
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 29

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80
```

-continued ggt gac gac cgt atg cgt cgc ctc cag ctg gcc gcg cgc cgc aac aaa 288
Gly Asp Asp Arg Met Arg Arg Leu Gln Leu Ala Ala Arg Arg Asn Lys
85 90 95 atc gca ctc gtc atg ggc tat tcg gag cgg gaa gcc gga tcg cgc tat 336
Ile Ala Leu Val Met Gly Tyr Ser Glu Arg Glu Ala Gly Ser Arg Tyr
100 105 110 ctg agc cag gtg ttc atc gac gag cgt ggc gag atc gtt gcc aat cgg 384
Leu Ser Gln Val Phe Ile Asp Glu Arg Gly Glu Ile Val Ala Asn Arg
115 120 125 cgc aag ctg aag ccc aca cac gtt gag cgt acg atc tac ggc gaa ggc 432
Arg Lys Leu Lys Pro Thr His Val Glu Arg Thr Ile Tyr Gly Glu Gly
130 135 140 aac gga acc gat ttc ctc acg cac gac ttc gcg ttc gga cgc gtc ggt 480
Asn Gly Thr Asp Phe Leu Thr His Asp Phe Ala Phe Gly Arg Val Gly
145 150 155 160 gga ttg aac tgc tgg gaa cat acc caa ccg ctc agc aag ttc atg atg 528
Gly Leu Asn Cys Trp Glu His Thr Gln Pro Leu Ser Lys Phe Met Met
165 170 175 tac agc ctc ggt gag cag gtc cac gtt gca tcg tgg ccg gcg atg tcc 576
Tyr Ser Leu Gly Glu Gln Val His Val Ala Ser Trp Pro Ala Met Ser
180 185 190 cct ctt cag ccg gat gtt ttc caa ctg agc atc gaa gcc aac gcg acg 624
Pro Leu Gln Pro Asp Val Phe Gln Leu Ser Ile Glu Ala Asn Ala Thr
195 200 205 gtc acc cgc tcg tac gca atc gaa ggc caa acc ttt gtg ctt tgc tcg 672
Val Thr Arg Ser Tyr Ala Ile Glu Gly Gln Thr Phe Val Leu Cys Ser
210 215 220 acg cag gtg atc gga cct agc gcg atc gaa acg ttc tgc ctc aac gac 720
Thr Gln Val Ile Gly Pro Ser Ala Ile Glu Thr Phe Cys Leu Asn Asp
225 230 235 240 gaa cag cgc gca ctg ttg ccg caa gga tgt ggc tgg gcg cgc att tac 768
Glu Gln Arg Ala Leu Leu Pro Gln Gly Cys Gly Trp Ala Arg Ile Tyr
245 250 255 ggc ccg gat gga agc gag ctt gcg aag cct ctg gcg gaa gat gct gag 816
Gly Pro Asp Gly Ser Glu Leu Ala Lys Pro Leu Ala Glu Asp Ala Glu
260 265 270 ggg atc ttg tac gca gag atc gat ctg gag cag att ctg ctg gcg aag 864
Gly Ile Leu Tyr Ala Glu Ile Asp Leu Glu Gln Ile Leu Leu Ala Lys
275 280 285 gct gga gcc gat ccg gtc ggg cac tat tcg cgg cct gac gtg ctg tcg 912
Ala Gly Ala Asp Pro Val Gly His Tyr Ser Arg Pro Asp Val Leu Ser
290 295 300 gtc cag ttc gac ccg cgc aat cat acg cca gtt cat cgc atc ggc att 960
Val Gln Phe Asp Pro Arg Asn His Thr Pro Val His Arg Ile Gly Ile
305 310 315 320 gac ggt cgc ttg gat gtg aat acc cgc agt cgc gtg gag aat ttc cga 1008
Asp Gly Arg Leu Asp Val Asn Thr Arg Ser Arg Val Glu Asn Phe Arg
325 330 335 ctg cga caa gcg gct gag cag gag cgt cag gca tcc aag cgg ctc gga 1056
Leu Arg Gln Ala Ala Glu Gln Glu Arg Gln Ala Ser Lys Arg Leu Gly
340 345 350 acg aaa ctc ttt gaa caa tcc ctt ctg gct gaa gaa ccg gtc cca gca 1104
Thr Lys Leu Phe Glu Gln Ser Leu Leu Ala Glu Glu Pro Val Pro Ala
355 360 365 aag tag 1110
Lys

<210> SEQ ID NO 30
<211> LENGTH: 369
<212> TYPE: PRT

-continued

<213> ORGANISM: Acidovorax facilis 72W

<400> SEQUENCE: 30

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Thr Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 31
<211> LENGTH: 1110
<212> TYPE: DNA

-continued

<213> ORGANISM: Acidovorax facilis 72W
<220> FEATURE:
<221> NAME/KEY: CDS
<222> LOCATION: (1)..(1110)

<400> SEQUENCE: 31

```
atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat gtg caa ccg ctc agc aag ttc atg atg      528
Gly Leu Asn Cys Trp Glu His Val Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285
```

-continued

```
gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys


<210> SEQ ID NO 32
<211> LENGTH: 369
<212> TYPE: PRT
<213> ORGANISM: Acidovorax facilis 72W

<400> SEQUENCE: 32

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255
```

-continued

```
Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 33
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 33

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
```

-continued

```
Tyr Ser Leu Gly Glu Gln Val His Val Ala Ser Trp Pro Ala Met Ser
            180                 185                 190

cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205

gtc gcc cgc tcg tac gca atc gaa ggc caa acc ttt gtg ctt tgc tcg      672
Val Ala Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys
```

<210> SEQ ID NO 34
<211> LENGTH: 369
<212> TYPE: PRT
<213> ORGANISM: Acidovorax facilis 72W

<400> SEQUENCE: 34

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110
```

-continued

```
Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Ala Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys


<210> SEQ ID NO 35
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 35

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
```

-continued

```
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205

gtc tgc cgc tcg tac gca atc gaa ggc caa acc ttt gtg ctt tgc tcg      672
Val Cys Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365

aag tag                                                             1110
Lys
```

<210> SEQ ID NO 36

-continued

<211> LENGTH: 369
<212> TYPE: PRT
<213> ORGANISM: Acidovorax facilis 72W

<400> SEQUENCE: 36

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Cys Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 37

-continued

```
<211> LENGTH: 1110
<212> TYPE: DNA
<213> ORGANISM: Escherichia coli SS1001
<220> FEATURE:
<221> NAME/KEY: CDS
<222> LOCATION: (1)..(1110)

<400> SEQUENCE: 37

atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15

ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30

atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45

gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60

tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80

ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95

atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110

ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125

cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140

aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160

gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175

tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190

cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205

gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220

acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240

gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255

ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270

ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
```

-continued

```
        275                 280                 285

gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300

gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320

gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335

ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350

acg aaa ctc ttt gaa caa tcc ctt ctg gct gaa gaa ccg gtc tca gca     1104
Thr Lys Leu Phe Glu Gln Ser Leu Leu Ala Glu Glu Pro Val Ser Ala
        355                 360                 365

aag tag                                                             1110
Lys


<210> SEQ ID NO 38
<211> LENGTH: 369
<212> TYPE: PRT
<213> ORGANISM: Escherichia coli SS1001

<400> SEQUENCE: 38

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
```

-continued

```
            245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Ser Ala
        355                 360                 365

Lys


<210> SEQ ID NO 39
<211> LENGTH: 12
<212> TYPE: PRT
<213> ORGANISM: artificial sequence
<220> FEATURE:
<223> OTHER INFORMATION: Conserved nitrilase catalytic domain
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid

<400> SEQUENCE: 39

Gly Xaa Leu Xaa Cys Xaa Glu Xaa Xaa Xaa Xaa Leu
1               5                   10
```

PROCESS FOR PRODUCING GLYCOLIC ACID FROM FORMALDEHYDE AND HYDROGEN CYANIDE

This application claims the benefit of U.S. Provisional Application Nos. 60/638,168; 60/638,148; 60/638,176; 60/638,127; 60/638,128; and 60/638,126; each filed Dec. 22, 2004.

FIELD OF THE INVENTION

This invention relates to the field of organic acid synthesis, molecular biology, and microbiology. More specifically, a process for the production of glycolic acid from formaldehyde and hydrogen cyanide is provided using an enzyme catalyst having nitrilase activity.

BACKGROUND OF THE INVENTION

Glycolic acid ($HOCH_2COOH$; CAS Registry Number is 79-14-1) is the simplest member of the α-hydroxy acid family of carboxylic acids. Its properties make it ideal for a broad spectrum of consumer and industrial applications, including use in water well rehabilitation, the leather industry, the oil and gas industry, the laundry and textile industry, as a monomer in the preparation of polyglycolic acid (PGA), and as a component in personal care products. Glycolic acid also is a principle ingredient for cleaners in a variety of industries (dairy and food processing equipment cleaners, household and institutional cleaners, industrial cleaners [for transportation equipment, masonry, printed circuit boards, stainless steel boiler and process equipment, cooling tower/heat exchangers], and metals processing [for metal pickling, copper brightening, etching, electroplating, electropolishing]). Recently, it has been reported that polyglycolic acid is useful as a gas barrier material (i.e., exhibits high oxygen barrier characteristics) for packing foods and carbonated drinks (WO 2005/106005 A1). However, traditional chemical synthesis of glycolic acid produces a significant amount of impurities that must be removed prior to use in preparing polyglycolic acid for gas barrier materials. New technology to commercially produce glycolic acid, especially one that produces glycolic acid in high purity and at low cost, would be eagerly received by industry.

Microbial catalysts can hydrolyze a nitrile (e.g., glycolonitrile) directly to the corresponding carboxylic acids (e.g., glycolic acid) using a nitrilase (EC 3.5.5.7), where there is no intermediate production of the corresponding amide (Equation 1), or by a combination of nitrile hydratase (EC 4.2.1.84) and amidase (EC 3.5.1.4) enzymes, where a nitrile hydratase (NHase) initially converts a nitrile to an amide, and then the amide is subsequently converted by the amidase to the corresponding carboxylic acid (Equation 2):

$$HOCH_2CN \xrightarrow[2H_2O]{\text{nitrilase}} HOCH_2CO_2H + NH_3 \quad (1)$$

$$HOCH_2CN \xrightarrow[H_2O]{\text{NHase}} HOCH_2CONH_2 \xrightarrow[H_2O]{\text{amidase}} HOCH_2CO_2H + NH_3 \quad (2)$$

Enzymatic synthesis of glycolic acid requires a substantially pure form of glycolonitrile. Methods to synthesize glycolonitrile by reacting aqueous solutions of formaldehyde and hydrogen cyanide have previously been reported (U.S. Pat. Nos. 2,175,805; 2,890,238; and 5,187,301; Equation 3).

$$HCN+HCHO \rightarrow HOCH_2CN \quad (3)$$

However, these methods typically result in an aqueous glycolonitrile reaction product that requires significant purification (e.g., distillative purification) as many of the impurities and/or byproducts of the reaction (including excess reactive formaldehyde) may interfere with the enzymatic conversion of glycolonitrile to glycolic acid, including catalyst inactivation. Inactivation of the enzyme catalyst decreases the overall productivity of the catalyst (i.e., total grams of glycolic acid formed per gram of catalyst), adding a significant cost to the overall process, which may make enzymatic production methods economically non-viable when compared to chemical methods of production. As such, reaction conditions that yield glycolonitrile with fewer impurities are needed, especially those that address the amount of free formaldehyde in the reaction product. The glycolonitrile synthesis conditions should 1) increase overall glycolonitrile yield, 2) minimize unwanted impurities and/or byproducts, and 3) decrease the cost to make a glycolonitrile preparation suitable for enzymatic synthesis.

Various methods are known for preparing a-hydroxy acids using the corresponding α-hydroxy nitrile as the starting material and a microorganism as the catalyst. Examples of α-hydroxy acids produced include: glycolic acid, lactic acid, 2-hydroxyisobutyric acid, 2-hydroxy-2-phenyl propionic acid, mandelic acid, 2-hydroxy-3,3-dimethyl-4-butyrolactone, and 4-methylthiobutyric acid. These products are synthesized using microorganisms, such as those belonging to the genera *Nocardia, Bacillus, Brevibacterium, Aureobacterium, Pseudomonas, Caseobacter, Alcaligenes, Acinetobacter, Enterobacter, Arthrobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium, Rhodopseudomonas, Rhodococcus, Corynebacterium, Microbacterium, Obsumbacterium* and *Gordona*. (JP-A-4-99495, JP-A-4-99496 and JP-A-4-218385 corresponding to U.S. Pat. No. 5,223,416; JP-A-4-99497 corresponding to U.S. Pat. No. 5,234,826; JP-A-5-95795 corresponding to U.S. Pat. No. 5,296,373; JP-A-5-21987; JP-A-5-192189 corresponding to U.S. Pat. No. 5,326,702; JP-A-6-237789 corresponding to EP-A-0610048; JP-A-6-284899 corresponding to EP-A-0610049; JP-A-7-213296 corresponding to U.S. Pat. No. 5,508,181).

However, most known methods for preparing α-hydroxy acids from the corresponding α-hydroxy nitriles as mentioned above do not produce and accumulate a product at a sufficiently high concentration to meet commercial needs. This is frequently a result of enzyme inactivation early in the reaction period. U.S. Pat. No. 5,756,306 teaches that "When an α-hydroxy nitrile is enzymatically hydrolyzed or hydrated using nitrilase or nitrile hydratase to produce an α-hydroxy acid or α-hydroxy amide, a problem occurs in that the enzyme is inactivated within a short period of time. It is therefore difficult to obtain the α-hydroxy acid or α-hydroxy amide in high concentration and high yield." (col. 1, lines 49-54). Maintaining the aldehyde concentration (formed by the dissociation of α-hydroxy nitrile to aldehyde and hydrogen cyanide) and/or the α-hydroxy nitrile concentration in the reaction mixture within a specified range is one method to avoid this problem.

U.S. Pat. No. 5,508,181 addresses further difficulties relating to rapid enzyme inactivation. Specifically, U.S. Pat. No. 5,508,181 mentions that α-hydroxy nitrile compounds partially disassociate into the corresponding aldehydes, according to the disassociation equilibrium. These aldehydes inactivate the enzyme within a short period of time by binding to the protein, thus making it difficult to obtain α-hydroxy acid or α-hydroxy amide in a high concentration with high productivity from α-hydroxy nitriles (col. 2, lines 16-29). As a solution to prevent enzyme inactivation due to accumulation of aldehydes, phosphate or hypophosphite ions were added to the reaction mixture. U.S. Pat. No. 5,326,702 uses sulfite, disulfite, or dithionite ions to sequester aldehyde and prevent enzyme inactivation. However, the concentration of α-hydroxy acid produced and accumulated even by using such additives as described above is not great.

U.S. Pat. No. 6,037,155 teaches that low accumulation of α-hydroxy acid product is related to enzyme inactivation within a short time due to the disassociated-aldehyde accumulation. These inventors suggest that enzymatic activity is inhibited in the presence of hydrogen cyanide (Asano et al., *Agricultural Biological Chemistry,* Vol. 46, pages 1165-1174 (1982)) generated in the partial disassociation of the α-hydroxy nitrile in water together with the corresponding aldehyde or ketone (Mowry, David T., *Chemical Reviews,* Vol. 42, pages 189-283 (1948)). The inventors solved the problem of aldehyde-induced enzyme inactivation by using microorganisms whose enzyme activity could be improved by adding a cyanide substance to the reaction mixture. The addition of a cyanide substance limited the disassociation of α-hydroxy nitrile to aldehyde and hydrogen cyanide.

With specific respect to the production of glycolic acid, glycolonitrile is known to reversibly disassociate to hydrogen cyanide and formaldehyde, either of which may be involved in enzyme inactivation. U.S. Pat. No. 3,940,316 describes a process for preparing an organic acid from the corresponding nitrile using bacteria with "nitrilasic" activity, and lists glycolonitrile as a substrate. In particular, this patent describes the use of *Bacillus, Bacteridium, Micrococcus,* and *Brevibacterium* for this purpose. Though described as having nitrilasic activity, *Brevibacterium* R312 is the only strain used in all of the U.S. Pat. No. 3,940,316 examples. *Brevibacterium* R312 is known to have nitrile hydratase and amidase activities, but no nitrilase activity (Tourneix et al., *Antonie van Leeuwenhoek,* 52:173-182 (1986)).

A method for preparing lactic acid, glycolic acid, and 2-hydroxyisobutyric acid by using a microorganism belonging to *Corynebacterium* spp. is disclosed in Japanese Patent Laid-open No. Sho 61-56086. JP 09028390 discloses a method for manufacturing glycolic acid from glycolonitrile by the action of *Rhodococcus* or *Gordona* hydrolase. Selectivity for glycolic acid is reported as almost 100%, without formation of glycolic acid amide. U.S. Pat. No. 6,037,155 discloses examples of methods for producing α-hydroxy acids from α-hydroxy nitriles, including glycolic acid. This disclosure acknowledges that not all microbial catalysts can produce high concentrations of glycolic acid due to the aforementioned problems and instructs that screening studies must be conducted in order to find industrially advantageous microorganisms. U.S. Pat. No. 6,037,155 specifically identifies *Variovorax spp.* and *Arthrobacter spp.* microorganisms that are resistant to the suppressing effect of α-hydroxy nitrile or α-hydroxy acid, have durable activity, and can produce the desired product at high concentration.

*Acidovorax facilis* 72W (ATCC 55746) is characterized by aliphatic nitrilase (EC 3.5.5.7) activity, as well as a combination of nitrile hydratase (EC 4.2.1.84) and amidase (EC 3.5.1.4) activities. The gene encoding the *A. facilis* 72W (ATCC 55746) nitrilase has been cloned and recombinantly expressed (WO 01/75077 corresponding to U.S. Pat. No. 6,870,038) and Chauhan et al., *Appl Microbiol Biotechnol,* 61:118-122 (2003)). The *A. facilis* 72W nitrilase converts α-hydroxynitriles to the corresponding α-hydroxycarboxylic acids in high yield (U.S. Pat. No. 6,383,786), including glycolic acid (U.S. Pat. No. 6,416,980). However, enzyme catalysts having improved nitrilase activity relative to the *A. facilis* 72W nitrilase when converting glycolonitrile to glycolic acid in high yield at up to 100% conversion would be very useful in reducing the cost of manufacturing glycolic acid.

A process to economically produce glycolic acid using an enzyme catalyst requires 1) a source of high purity glycolonitrile, 2) the use of an enzyme catalyst that can convert glycolonitrile to glycolic acid in high concentrations with high purity, and 3) a method recovering the glycolic acid produced. In one embodiment, the process includes use of an enzyme catalyst having high catalyst productivity (kg glycolic acid/kg enzyme catalyst) and volumetric productivity (grams of glycolic acid/L/h). The enzyme catalyst may be employed in multiple consecutive batch reactions, or in a continuous reaction that employs constant addition of glycolonitrile and removal of glycolic acid; in either mode of operation, the catalyst activity and lifetime should be such that a high volumetric productivity and catalyst productivity are obtained, and in the case of batch reactions, the catalyst must be utilized in multiple reaction cycles without significant loss in enzyme activity between consecutive batch reactions. Nitrilases having improved activity for glycolonitrile hydrolysis can provide improvements in volumetric productivity. Given the fact that the inactivating effect of free formaldehyde (and possibly other impurities) in the glycolonitrile reaction mixture will negatively affect all nitrilase catalysts to varying extents, improvements that stabilize enzyme activity under reaction conditions for hydrolysis of glycolonitrile (resulting in a relative increase in catalyst productivity) are also needed.

Enzymatic conversion of glycolonitrile to glycolic acid using an enzyme catalyst normally results in the production of an aqueous solution comprising mostly ammonium glycolate (i.e., reactions are typically run at a pH of about 6 to about 9). Various methods can be used to obtain glycolic acid from aqueous solutions of ammonium glycolate including, but not limited to ion exchange (anionic and/or cationic), electrodialysis, reactive solvent extraction, polymerization, thermal decomposition (salt cracking), alcoholysis, and combinations thereof.

The problem to be solved is to provide a process to produce glycolic acid (in the form of the salt of acid) in high yield and with high purity. In one embodiment, the desired process should include 1) preparation of an aqueous solution comprising glycolonitrile from formaldehyde and hydrogen cyanide suitable for enzymatic conversion to ammonium glycolate (i.e., "high purity" glycolonitrile), 2) use of an enzyme catalyst having nitrilase activity the hydrolyzes the high purity glycolonitrile into ammonium glycolate, and 3) a method to obtain high purity glycolic acid from the ammonium glycolate. In another embodiment, the process includes use of an enzyme catalyst having improved nitrilase activity (thereby increasing volumetric productivity) relative to the nitrilase activity of the *Acidovorax facilis* 72W nitrilase, and reaction conditions that improve catalyst stability and productivity.

SUMMARY OF THE INVENTION

The present problem has been solved by providing a process to produce glycolic acid from formaldehyde and hydrogen cyanide comprising:

a) providing an aqueous formaldehyde feed stream heated to a temperature of about 90° C. to about 150° C. for a determinable period of time;

b) contacting the heated aqueous formaldehyde feed stream of (a) with hydrogen cyanide at a temperature suitable for glycolonitrile synthesis, whereby glycolonitrile is produced;

c) contacting the glycolonitrile produced in step (b) in a suitable aqueous enzymatic reaction mixture with an enzyme catalyst comprising a polypeptide having nitrilase activity, said polypeptide having an amino acid sequence of SEQ ID NO: 6 with at least one amino acid substitution selected from the group consisting of:

(1) a substitution at amino acid residue 168 with lysine, methionine, threonine or valine; and (2) a substitution at amino acid residue 201 with glutamine, glycine, histidine, lysine, asparagine, serine, alanine, cysteine, or threonine; whereby glycolic acid is produced in the form of a salt or acid; wherein said enzyme catalyst provides at least a 1.5-fold increase in nitrilase activity relative to the nitrilase activity of the *Acidovorax facilis* 72W nitrilase catalyst when converting glycolonitrile to glycolic acid under identical reaction conditions; and d) recovering the glycolic acid produced in (c) in the form of a salt or acid.

In one embodiment, the methods of recovering the glycolic acid in step d) include, but are not limited to ion exchange, electrodialysis, reactive solvent extraction, thermal decomposition, alcoholysis, polymerization, and combinations thereof.

The high purity glycolonitrile produced using the present process enables production of high purity glycolic acid when using an enzyme catalyst comprising a polypeptide having nitrilase activity (i.e, a nitrilase) in combination with ion exchange. As such, a process for producing glycolic acid from formaldehyde and hydrogen cyanide is provided comprising:

(a) providing an aqueous formaldehyde feed stream that is heated to a temperature of about 90° C. to about 150° C. for a determinable period of time;

(b) contacting the heated aqueous feed stream of (a) with hydrogen cyanide at a temperature suitable for glycolonitrile synthesis, whereby glycolonitrile is produced;

(c) contacting the glycolonitrile of step (b) in a suitable aqueous reaction mixture with an enzyme catalyst comprising a polypeptide having nitrilase activity, whereby glycolic acid is produced; and (d) recovering the glycolic acid produced in (c) by ion exchange;

wherein said glycolic acid has a purity of at least 99.9%.

BRIEF DESCRIPTION OF THE FIGURES, THE SEQUENCE LISTING, AND THE BIOLOGICAL DEPOSITS

The invention can be more fully understood from the figures, the sequence listing, the biological deposits, and the detailed description that together form this application.

FIGURES

FIG. 1 shows $^{13}C$ NMR spectrum of the resulting glycolonitrile solution from Comparative Example A, qualitatively indicating the purity of the glycolonitrile product. The $^{13}C$ NMR spectrum shows the major glycolonitrile $^{13}C$ resonances at about δ 48 and 119 ppm. There are also substantial resonances around δ 80-90 ppm for unreacted formaldehyde and around δ 60 ppm for other by-product species derived from unreacted formaldehyde.

FIG. 2 shows $^{13}C$ NMR spectrum of the resulting glycolonitrile solution from Example 1, qualitatively indicating the purity of the glycolonitrile product. The major resonances for glycolonitrile at about δ 48 and 119 ppm are observed. The resonances around δ 80-90 ppm evident in FIG. 1 for unreacted formaldehyde are noticeably reduced in FIG. 2. However, the resonances around δ 60 ppm for by-products derived from unreacted formaldehyde remain, most likely due to the initial formaldehyde reactor charge.

FIG. 3 shows $^{13}C$ NMR spectrum of the resulting glycolonitrile solution from Example 2, qualitatively indicating the purity of the glycolonitrile product. The major resonances for glycolonitrile at about δ 48 and 119 ppm are evident in FIG. 3, while the levels of impurities are substantially reduced from the levels observed in FIG. 1 and FIG. 2.

FIG. 4 shows $^{13}C$ NMR spectrum of the resulting glycolonitrile solution from Example 3, qualitatively indicating the purity of the glycolonitrile product. The major resonances for glycolonitrile at about δ 48 and 119 ppm are evident in FIG. 4, while the levels of impurities are substantially reduced from the levels observed in FIG. 1 and FIG. 2. FIG. 4 also clearly shows the resonance at δ 49 ppm for the methanol from the formalin feed used in Example 3.

SEQUENCE LISTING

Figure 1:
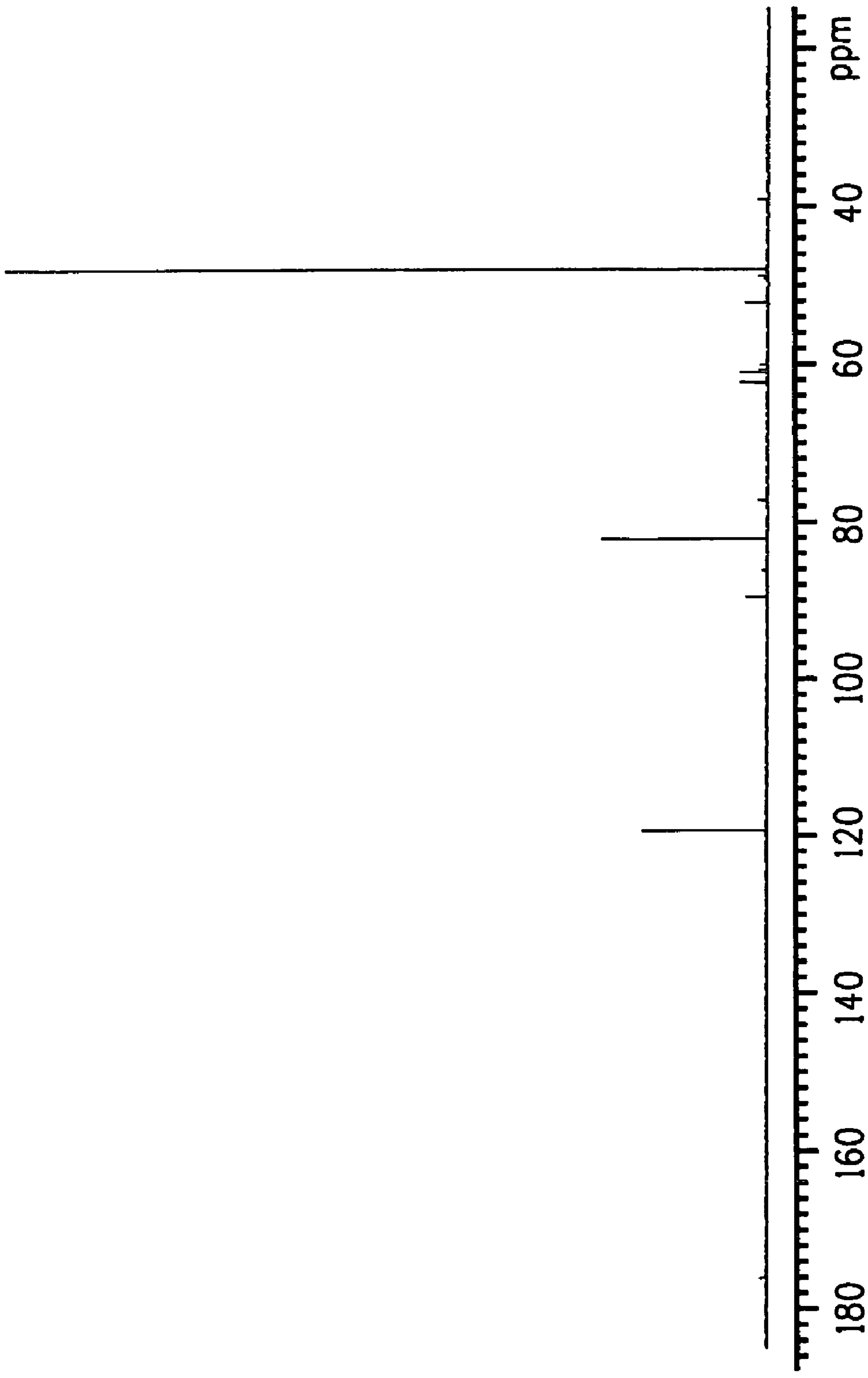

The following sequence descriptions and sequences listings attached hereto comply with the rules governing nucleotide and/or amino acid sequence disclosures in patent applications as set forth in 37 C.F.R. §1.821-1.825. The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NO: 1 is the nucleotide sequence of a primer 165 used to amplify the *Acidovorax facilis* 72W nitrilase coding sequence. The amplified PCR product was subsequently cloned into pUC19 (New England Biolabs, Beverly, Mass.; GenBank® L09137) to create plasmid pSW138.

SEQ ID NO: 2: is the nucleotide sequence of a primer 166 used to amplify the *Acidovorax facilis* 72W nitrilase coding sequence. The amplified PCR product was subsequently cloned into pUC19 (New England Biolabs, Beverly, Mass.; GenBank® L09137) to create plasmid pSW138.

SEQ ID NO: 3 is the nucleotide sequence of a primer used to amplify the *Acidovorax facilis* 72W nitrilase.

SEQ ID NO: 4 is the nucleotide sequence of a primer used to amplify the *Acidovorax facilis* 72W nitrilase.

SEQ ID NO: 5 is the nucleotide sequence of the *Acidovorax facilis* 72W nitrilase coding sequence comprising a change in the start codon from TTG to ATG to facilitate recombinant expression in *E. coli.*

SEQ ID NO: 6 is the deduced amino acid sequence of the *Acidovorax facilis* 72W nitrilase encoded by the nucleotide sequence of SEQ ID NO: 5 comprising a change in the start codon from TTG to ATG to facilitate recombinant expression in *E. coli.*

SEQ ID NO: 7 is the nucleotide sequence of an *A. facilis* 72W nitrilase mutant comprising a codon change, which resulted in a single amino acid substitution at residue position 201 (L201Q; Leu→Gln).

SEQ ID NO: 8 is the deduced amino acid sequence of the mutant nitrilase (SEQ ID NO: 7) comprising a single amino acid substitution at residue position 201 (Leu201→Gln) of the *A. facilis* 72W nitrilase.

SEQ ID NO: 9 is the nucleotide sequence of an *A. facilis* 72W nitrilase mutant comprising a codon change, which resulted in a single amino acid substitution at residue position 201 (L201A; Leu→Ala).

SEQ ID NO: 10 is the deduced amino acid sequence of the mutant nitrilase (SEQ ID NO: 9) comprising a single amino acid substitution at residue position 201 (Leu201→Ala) of the *A. facilis* 72W nitrilase.

SEQ ID NO: 11 is the nucleotide sequence of an *A. facilis* 72W nitrilase mutant comprising a codon change, which resulted in a single amino acid substitution at residue position 201 (L201C; Leu→Cys).

SEQ ID NO: 12 is the deduced amino acid sequence of the mutant nitrilase (SEQ ID NO: 11) comprising a single amino acid substitution at residue position 201 (Leu201→Cys) of the *A. facilis* 72W nitrilase.

SEQ ID NO: 13 is the nucleotide sequence of an *A. facilis* 72W nitrilase mutant comprising a codon change, which resulted in a single amino acid substitution at residue position 201 (L201T; Leu→Thr).

SEQ ID NO: 14 is the deduced amino acid sequence of the mutant nitrilase (SEQ ID NO: 13) comprising a single amino acid substitution at residue position 201 (Leu201→Thr) of the *A. facilis* 72W nitrilase.

SEQ ID NO: 15 is the nucleotide sequence of an *A. facilis* 72W nitrilase mutant comprising a codon change, which resulted in a single amino acid substitution at residue position 201 (L201G; Leu→Gly).

SEQ ID NO: 16 is the deduced amino acid sequence of the mutant nitrilase (SEQ ID NO: 15) comprising a single amino acid substitution at residue position 201 (Leu201→Gly) of the *A. facilis* 72W nitrilase.

SEQ ID NO: 17 is the nucleotide sequence of an *A. facilis* 72W nitrilase mutant comprising a codon change, which resulted in a single amino acid substitution at residue position 201 (L201 H; Leu→His).

SEQ ID NO: 18 is the deduced amino acid sequence of the mutant nitrilase (SEQ ID NO: 17) comprising a single amino acid substitution at residue position 201 (Leu201→His) of the *A. facilis* 72W nitrilase.

SEQ ID NO: 19 is the nucleotide sequence of an *A. facilis* 72W nitrilase mutant comprising a codon change, which resulted in a single amino acid substitution at residue position 201 (L201K; Leu→Lys).

SEQ ID NO: 20 is the deduced amino acid sequence of the mutant nitrilase (SEQ ID NO: 19) comprising a single amino acid substitution at residue position 201 (Leu201→Lys) of the *A. facilis* 72W nitrilase.

SEQ ID NO: 21 is the nucleotide sequence of an *A. facilis* 72W nitrilase mutant comprising a codon change, which resulted in a single amino acid substitution at residue position 201 (L201 N; Leu→Asn).

SEQ ID NO: 22 is the deduced amino acid sequence of the mutant nitrilase (SEQ ID NO: 21) comprising a single amino acid substitution at residue position 201 (Leu201→Asn) of the *A. facilis* 72W nitrilase.

SEQ ID NO: 23 is the nucleotide sequence of an *A. facilis* 72W nitrilase mutant comprising a codon change, which resulted in a single amino acid substitution at residue position 201 (L201S; Leu→Ser).

SEQ ID NO: 24 is the deduced amino acid sequence of the mutant nitrilase (SEQ ID NO: 23) comprising a single amino acid substitution at residue position 201 (Leu201→Ser) of the *A. facilis* 72W nitrilase.

SEQ ID NO: 25 is the nucleotide sequence of an *A. facilis* 72W nitrilase mutant comprising a codon change, which resulted in a single amino acid substitution at residue position 168 (F168K; Phe→Lys).

SEQ ID NO: 26 is the deduced amino acid sequence of the mutant nitrilase (SEQ ID NO: 25) comprising a single amino acid substitution at residue position 168 (Phe168→Lys) of the *A. facilis* 72W nitrilase.

SEQ ID NO: 27 is the nucleotide sequence of an *A. facilis* 72W nitrilase mutant comprising a codon change, which resulted in a single amino acid substitution at residue position 168 (F168M; Phe→Met).

SEQ ID NO: 28 is the deduced amino acid sequence of the mutant nitrilase (SEQ ID NO: 27) comprising a single amino acid substitution at residue position 168 (Phe168→Met) of the *A. facilis* 72W nitrilase.

SEQ ID NO: 29 is the nucleotide sequence of an *A. facilis* 72W nitrilase mutant comprising a codon change, which resulted in a single amino acid substitution at residue position 168 (F168T; Phe→Thr).

SEQ ID NO: 30 is the deduced amino acid sequence of the mutant nitrilase (SEQ ID NO: 29) comprising a single amino acid substitution at residue position 168 (Phe168→Thr) of the *A. facilis* 72W nitrilase.

SEQ ID NO: 31 is the nucleotide sequence of an *A. facilis* 72W nitrilase mutant comprising a codon change, which resulted in a single amino acid substitution at residue position 168 (F168V; Phe→Val).

SEQ ID NO: 32 is the deduced amino acid sequence of the mutant nitrilase (SEQ ID NO: 31) comprising a single amino acid substitution at residue position 168 (Phe168→Val) of the *A. facilis* 72W nitrilase.

SEQ ID NO: 33 is the nucleotide sequence of an *A. facilis* 72W nitrilase mutant comprising a codon change, which resulted in a single amino acid substitution at residue position 168 (T210A; Thr→Ala).

SEQ ID NO: 34 is the deduced amino acid sequence of the mutant nitrilase (SEQ ID NO: 33) comprising a single amino acid substitution at residue position 210 (Thr210→Ala) of the *A. facilis* 72W nitrilase.

SEQ ID NO: 35 is the nucleotide sequence of an *A. facilis* 72W nitrilase mutant comprising a codon change, which resulted in a single amino acid substitution at residue position 168 (T210C; Thr→Cys).

SEQ ID NO: 36 is the deduced amino acid sequence of the mutant nitrilase (SEQ ID NO: 35) comprising a single amino acid substitution at residue position 210 (Thr210→Cys) of the *A. facilis* 72W nitrilase.

SEQ ID NO: 37 is the nucleotide sequence of an *A. facilis* 72W nitrilase gene expressed in *E. coli* SS1001 (ATCC PTA-1177; U.S. Pat. No. 6,870,038 herein incorporated by reference).

SEQ ID NO: 38 is the deduced amino acid sequence of the *A. facilis* 72W nitrilase (SEQ ID NO: 33) expressed in *E. coli* SS1001 (ATCC PTA-1177).

SEQ ID NO: 39 is the amino acid sequence of catalytic region conserved among polypeptides having nitrilase activity.

BIOLOGICAL DEPOSITS

The following biological deposits have been made under the terms of the Budapest Treaty on the International Recognition of the Deposit of Microorganisms for the Purposes of Patent Procedure:

| Depositor Identification Reference | Int'l. Depository Designation | Date of Deposit |
|---|---|---|
| *Acidovorax facilis* 72W | ATCC 55746 | 8 Mar. 1996 |
| *E. coil* SS1001 | ATCC PTA-1177 | 11 Jan. 2000 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

An integrated process for producing glycolic acid from formaldehyde and hydrogen cyanide is provided. The process begins with the synthesis of glycolonitrile by contacting heat-treated formaldehyde and hydrogen cyanide at a temperature suitable for glycolonitrile synthesis. The product of this reaction is an aqueous solution of glycolonitrile having fewer impurities (e.g., unreacted monomeric "free" formaldehyde). The high-purity glycolonitrile is subsequently contacted with an enzyme catalyst having nitrilase activity whereby an aqueous solution comprising ammonium glycolate is produced. High purity glycolic acid (having a purity of at least 99.9%) can then be obtained from the ammonium glycolate using a method such as ion exchange.

In one embodiment, the process uses an enzyme catalyst comprising a polypeptide providing a significant (i.e., at least 1.5-fold) improvement nitrilase activity when compared to the nitrilase activity of the *Acidovorax facilis* 72W (ATCC 55746) nitrilase (SEQ ID NO: 6) under identical reaction conditions. The improvement in catalyst activity increases catalyst productivity and volumetric productivity, decreasing the overall cost of manufacturing high purity glycolic acid.

In another embodiment, the enzyme catalyst having a significant improvement in nitrilase activity comprises a polypeptide having an amino acid sequence of SEQ ID NO: 6 with at least one amino acid substitution selected from the group consisting of:

(a) a substitution at amino acid residue 168 with lysine, methionine, threonine or valine; and (b) a substitution at amino acid residue 201 with glutamine, glycine, histidine, lysine, asparagine, serine, alanine, cysteine, or threonine.

In a further embodiment, the enzyme catalyst provides a catalyst productivity of at least 300 grams of glycolic acid per gram dry cell weight of enzyme catalyst.

The aqueous solution comprising glycolonitrile is converted into the ammonium salt of the glycolic acid (ammonium glycolate) using an enzyme catalyst having nitrilase activity where the pH of the reaction is generally maintained between about pH 6 and about pH 8 (pKa of glycolic acid ~3.83). A variety of methods can than be used to obtain glycolic acid from the aqueous solution of ammonium glycolate including, but not limited to ion exchange, electrodialysis, reactive solvent extraction, thermal decomposition (salt cracking), alcoholysis, and combinations thereof. One of skill in the art will recognize that the preferred isolation/purification strategy for glycolic acid is determined by location-specific factors such as energy cost, by-product values, waste disposal costs, capital equipment investment, financing opportunities, as well as local, state and national laws, rules and regulations including environmental considerations.

Several process conditions are also provided that improve enzyme catalyst stability and productivity, thereby decreasing catalyst cost and overall cost of manufacture. These process conditions include 1) the use of additives to stabilize enzyme catalyst activity, 2) running the enzymatic catalyzed reaction under substantially oxygen free conditions, and 3) controlling the feed rate of glycolonitrile to the reaction mixture so that a targeted concentration of glycolonitrile is maintained.

Definitions:

In this disclosure, a number of terms and abbreviations are used. The following definitions apply unless specifically stated otherwise.

As used herein, he term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein, the term "recovering" means isolating, purifying, or transferring the product formed by the present process. Methods to isolate and purify the product(s) from the reaction mixture are well known in the art may include, but are not limited to selective precipitation, crystallization, filtration, reactive solvent extraction, ion exchange, electrodialysis, polymerization, distillation, thermal decomposition, alcoholysis, column chromatography, and combinations thereof. In one embodiment, the term "recovering" may also include transferring the product mixture (typically after filtering out the enzyme catalyst) to another reaction to create one or more additional products. In a preferred embodiment, ion exchange is used to recover the glycolic acid.

As used herein, the term "glycolonitrile" is abbreviated as "GLN" and is synonymous with hydroxyacetonitrile, 2-hydroxyacetonitrile, hydroxymethylnitrile, and all other synonyms of CAS Registry Number 107-16-4.

As used herein, the term "glycolic acid" is abbreviated as "GLA" and is synonymous with hydroxyacetic acid, hydroxyethanoic acid, and all other synonyms of CAS Registry Number 79-14-1. The glycolic acid produced by the present processes may in the form of the protonated carboxylic acid and/or the corresponding ammonium salt.

As used herein, the term "ammonium glycolate" is abbreviated "$NH_4GLA$".

As used herein, the term "glycolamide" is the amide derived from the reaction of ammonia with glycolic acid and refers to all other synonyms of compounds having CAS Registry Number 598-42-5.

As used herein, the term "glycolide" refers to the compound of CAS Registry Number 502-97-6.

As used herein, the term "formaldehyde" is abbreviated as "FA" and is synonymous with formic aldehyde, methyl aldehyde, oxomethane, and all other synonyms of CAS Registry Number 50-00-0. Commercially available formaldehyde is typically comprised of a mixture of monomeric formaldehyde ("free formaldehyde") and various oligomers of formaldehyde along with some methanol (typically about 1 wt % to about 15 wt %).

As used herein, the term "hydrogen cyanide" is synonymous with prussic acid, hydrocyanic acid, and all other synonyms of CAS Registry Number 200-821-6.

As used herein, the terms "formaldehyde heat treatment", "heat-treated formaldehyde", "heating the formaldehyde feed stream", "pre-heated formaldehyde", and "an aqueous formaldehyde feed stream that is heated" are used to describe the process of subjecting an aqueous formaldehyde solution to a prescribed temperature for a determinable period of time prior to reacting with hydrogen cyanide. As used herein, the term "determinable period of time" is used to describe the amount of time the formaldehyde feed stream is heated to the specified temperature. The optimal length of time the formaldehyde is heat-treated can be easily determined and may be adjusted depending upon the selected temperature in combination with the specific design of the heat treatment system and the reactor. The length of the heat treatment is chosen to maximize the amount of monomeric formaldehyde in the heated feed stream. The monomeric formaldehyde reacts with the hydrogen cyanide to produce a glycolonitrile solution with substantially fewer impurities (i.e. unreacted formaldehyde and impurities associated with polymeric forms of formaldehyde). Typically, the heat treatment period can last from about 10 seconds to about 24 hours, preferably about 10 seconds to about 6 hours, more preferably about 10 seconds to about 20 minutes, and most preferably about 2 minutes to about 10 minutes. In one embodiment, the heat treatment time is about 2 minutes to about 10 minutes in the presence of a base catalyst. The heated formaldehyde is then promptly fed to the reaction chamber. The heated formaldehyde is promptly fed to the reactor and contacted with hydrogen cyanide whereby glycolonitrile at "a temperature suitable for glycolonitrile synthesis".

As used herein, the term "a temperature suitable for glycolonitrile synthesis" is used to describe a reaction temperature range suitable for reacting hydrogen cyanide and the heat-treated formaldehyde. In one embodiment, the reaction temperature is typically about 70° C. or less in order to minimize glycolonitrile decomposition. In another embodiment, the reaction temperature is between about −20° C. to about 70° C., preferably about 0° C. to about 70° C., more preferably about 0° C. to about 55° C., even more preferably about 10° C. to about 30° C., and most preferably about 20° C. to about 25° C.

As used herein, the terms "promptly fed to the reactor" and "promptly adding the heated formaldehyde" are used to described the time period between the end of the heat treatment period and the initiation of the reaction with hydrogen cyanide, typically less than about 24 hours, preferably less than about 1 hour, more preferably less than about 15 minutes, most preferably less than about 5 minutes.

As used herein, the terms "*Acidovorax facilis*" and "*A. facilis*" are used interchangeably and refer to *Acidovorax facilis* 72W deposited to the American Type Culture Collection (an international depository authority) having accession number 55746 ("ATCC 55746"). The present mutant nitrilases having improved nitrilase activity were engineered by subjecting the *Acidovorax facilis* 72W nitrilase to error-prone PCR and/or targeted saturation mutagenesis.

As used herein, the terms "*Escherichia coli*" and "*E. coli*" are used interchangeably. Several strains of *E. coli* suitable for recombinant expression are described herein including, but not limited to *E. coli* MG1655 having international depository number ATCC 47076, *E. coli* FM5 having international depository number ATCC 53911, *E. coli* W3110 having international depository number ATCC 27325, *E. coli* MC4100 having international depository number ATCC 35695, and *E. coli* W1485 having international depository number ATCC 12435. In one embodiment, suitable *Escherichia coli* strains include *E. coli* FM5 (ATCC 53911) and *E. coli* MG1655 (ATCC 47076).

As used herein, the terms "*E. coli* SS1001" or "SS1001" refer to a transformed *E. coli* strain expressing the *Acidovorax facilis* 72W nitrilase having ATCC Accession No. PTA-1177 (U.S. Pat. No. 6,870,038; herein incorporated in its entirety by reference). The recombinantly expressed *E. coli* SS1001 nitrilase (SEQ ID NO: 38) contains 2 minor sequence changes in comparison to the wild-type 72W nitrilase sequence (SEQ ID NO: 6). The start codon was changed from GTG to ATG to facilitate recombinant expression and an artifact was introduced during cloning that resulted in a single amino acid change near the C-terminal (Pro367 [CCA]→Ser [TCA]).

As used herein, the term "stabilizing agent" will be used to describe materials that may be added to the enzymatic catalyst reaction mixture that may help stabilize catalyst activity. The stabilizing agents may include, but are not limited to thiosulfates (e.g. potassium thiosulfate, $K_2S_2O_3$), dithionites (e.g., sodium dithionite, $Na_2S_2O_4$), and cyanide compounds (e.g. HCN, NaCN, KCN, etc.).

As used herein, the terms "suitable aqueous glycolonitrile reaction mixture" and "suitable aqueous reaction mixture" refer to the materials and water in which the glycolonitrile and enzyme catalyst come into contact. The components of the suitable aqueous reaction mixture are provided herein and those skilled in the art appreciate the range of component variations suitable for this process.

As used herein, the terms "aqueous ammonium glycolate solution", "aqueous solution comprising ammonium glycolate", and "aqueous solution of ammonium glycolate" will be used to describe an aqueous solution comprising ammonium glycolate produced by the enzymatic hydrolysis of glycolonitrile under typical enzymatic reaction conditions (i.e., a pH range of about 6 to about 8). The aqueous solution of ammonium glycolate comprises ammonium glycolate at a concentration of at least about 0.1 weight percent (wt %) to about 99 wt % ammonium glycolate. In another embodiment, the aqueous solution of ammonium glycolate is comprised of at least about 10 wt % to about 75 wt % ammonium glycolate. In a further embodiment, the aqueous solution of ammonium glycolate is comprised of at least about 20 wt % to about 50 wt % ammonium glycolate. The pH of the aqueous solution of ammonium glycolate can be about 2 to about 12, preferably 5 to about 10, more preferably 6 to about 8. The pH may be adjusted as needed prior to initiating process steps related to recovering glycolic acid (in the form of the acid or salt) from the aqueous ammonium glycolate solution.

As used herein, the term "aqueous ammonium glycolate feed stream" will be used to describe an aqueous solution comprising ammonium glycolate when used as a feed stream in a process step used to obtain and/or recover glycolic acid from the aqueous solution of ammonium glycolate. In one embodiment, the aqueous ammonium glycolate feed stream may also be concentrated and/or acidified (typically using a mineral acid such as $H_2SO_4$) prior to isolation of the final glycolic acid product in the present invention. A variety of processing techniques known and the art and several described herein can be used to obtain and/or recover glycolic acid from the aqueous solution of ammonium glycolate produced by the present method.

As used herein, the term "enzyme catalyst" or "nitrilase catalyst" refers to a catalyst that is characterized by a nitrilase activity (EC 3.5.5.7). The enzyme catalyst comprises a polypeptide ("nitrilase") having nitrilase activity for converting glycolonitrile to glycolic acid and ammonia. A nitrilase enzyme directly converts an aliphatic nitrile to the corresponding carboxylic acid, without forming the corresponding amide as intermediate (see Equation 1). Nitrilases share several conserved signature domains known in the art including a signature domain herein referred to as the "catalytic domain" or "catalytic region". This region comprises an essential cysteine residue (e.g., Cys164 of SEQ ID NO: 6). As such, polypeptides having nitrilase activity can be identified by the existence of the catalytic domain amino acid sequence (G-Xaa-L-Xaa-C-Xaa-E-Xaa-Xaa-Xaa-Xaa-L; SEQ ID NO: 39 wherein Xaa is a non-conserved amino acid).

The enzyme catalyst may be in the form of a whole microbial cell, a permeabilized microbial cell, one or more cell components of a microbial cell extract, partially purified enzyme, or purified enzyme. As used herein, "recycled enzyme catalyst" refers to an enzyme catalyst that is reused as an enzyme catalyst in batch reactions.

As used herein, the terms "improved nitrilase", "mutant nitrilase", "*Acidovorax facilis* 72W mutant nitrilase", and "protein engineered nitrilase" will be used interchangeably to refer to the present enzyme catalyst comprising a polypeptide providing a significant improvement in nitrilase activity towards the conversion of glycolonitrile to glycolic acid in comparison to the activity of the *A. facilis* 72W nitrilase (SEQ ID NO: 6) under identical reaction conditions. In one embodiment, the improvement in nitrilase activity can be determined by comparing the nitrilase activity of present nitrilases against the nitrilase activity of the *A. facilis* 72W nitrilase when recombinantly expressed (using identical expression systems) and assayed under essentially identical reaction conditions. SDS-PAGE analysis indicated that protein expression levels between the present mutants and their respective controls (SEQ ID NO: 6) were essentially identical. As such, improvements in nitrilase activity are attributed to structural modifications to the native *A. facilis* 72W nitrilase.

As used herein, the terms "catalyst productivity" and "enzyme catalyst productivity" refer to the total amount of product produced per gram of catalyst. In the present invention, the catalyst is a nitrilase enzyme (EC 3.5.5.7) and the product formed is glycolic acid and/or ammonium glycolate (depending upon the pH of the reaction). In general, the present methods are conducted under essentially pH neutral conditions so that the glycolic acid produced is predominantly in the form of the corresponding salt of glycolic acid (i.e. ammonium glycolate). Generally, in batch reactions with catalyst recycle, the catalyst activity decreases with each recycle reaction (enzyme inactivation).

The term "nitrilase activity" refers to the enzyme activity per unit mass (for example, milligram) of protein, dry cell weight, or bead weight (immobilized catalyst) when converting glycolonitrile to glycolic acid (or the corresponding ammonium glycolate). Comparisons in nitrilase activity were measured proportional to the dry cell weight or bead weight. Since nitrilase expression levels between the *A. facilis* 72W controls (transformed microbial cells expressing the *A. facilis* 72W nitrilase having the amino acid sequence of SEQ ID NO: 6) and the improved mutants (transformed microbial cells expressing the present nitrilases) were indistinguishable as quantified using laser densitometry analysis of an SDS-PAGE gel, comparisons and reported improvements in nitrilase activity were measured relative to dry cell weight (dcw) or bead weight (bw).

As used herein, the term "one unit of enzyme activity" or "one unit of nitrilase activity" or "U" is defined as the amount of enzyme activity required for the production of 1 μmol of glycolic acid product per minute (GLA U/g dry cell weight or bead weight) at a specified temperature (e.g. 25° C.).

As used herein, the terms "relative nitrilase activity", "improved nitrilase activity", and "relative improvement in nitrilase activity" refers to the nitrilase activity expressed as a multiple (or fraction) of a reference (control) nitrilase activity. The present mutant nitrilases exhibit a significant improvement in nitrilase activity relative to the nitrilase activity observed with native *Acidovorax facilis* 72W nitrilase. In the present invention, a "significant improvement" in relative nitrilase activity is an improvement of at least 1.5-fold higher nitrilase activity in comparison to the nitrilase activity of the control (*A. facilis* 72W nitrilase; SEQ ID NO: 6) under identical reaction conditions. In another embodiment, the improvement is at least 2-fold higher nitrilase activity in comparison to the nitrilase activity of the control under identical reaction conditions. In a further embodiment, the improvement is at least 4-fold higher nitrilase activity in comparison to the nitrilase activity of the control under identical reaction conditions.

As used herein, the term "initial reaction rate" is a measurement of the rate of conversion of glycolonitrile to glycolic acid under the stated reaction conditions, where the measurement of reaction rate begins upon the initial addition of glycolonitrile to the reaction mixture, and where the reaction rate is measured over a period of time where the concentration of glycolonitrile remains above ca. 50 millimolar (mM) during the course of the reaction. The reaction rate is measured as the change in concentration of glycolic acid produced per unit time (e.g., mole glycolic acid/L/min or mM glycolic acid/hour).

As used herein, the terms "recombinant organism", "transformed host", "transformant", "transgenic organism", and "transformed microbial host" refer to a host organism having been transformed with heterologous or foreign DNA. The recombinant organisms of the present invention express foreign coding sequences or genes that encode active nitrilase enzyme. "Transformation" refers to the transfer of a DNA fragment into the host organism. The transferred DNA fragment can be chromosomally or extrachromosomally incorporated (i.e., via a vector) into the host organism. As used herein, the term "transformation cassette" refers to a specific fragment of DNA containing a set of genetic elements conveniently arranged for insertion into a host cell, usually as part of a plasmid. As used herein, the term "expression cassette" refers to a specific fragment of DNA containing a set of genetic elements conveniently arranged for insertion into a host cell, usually as part of a plasmid, that also allows for enhanced gene expression in the host.

As used herein, the terms "nucleic acid fragment" and "nucleic acid molecule" refer to DNA molecule that may encode an entire gene, coding sequence, and/or regulatory sequences preceding (5', upstream) or following (3', downstream) the coding sequence. In one aspect, the present nucleic acid molecules encode for polypeptides having nitrilase activity.

As used herein, the term "gene" refers to a nucleic acid molecule that expresses a specific protein. As used herein, it may or may not including regulatory sequences preceding (5' non-coding sequences) and following (3' non-coding sequences) the coding sequence. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, the term "coding sequence" refers to a DNA sequence that codes for a specific amino acid sequence. As used herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. Promoters that cause a gene to be expressed in most cell types at most times or under most environmental conditions are commonly referred to as "constitutive promoters". Promoters that cause a gene to be expressed only in the presence of a particular compound or environmental condition are commonly referred to as "inducible promoters". Since in most cases the exact boundaries of regulatory sequences have not been completely defined, DNA fragments of different lengths may have identical promoter activity.

As used herein, the term "operably linked" refers to the association of nucleic acid sequences on a single nucleic acid molecule so that the function of one sequence is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, the term "3' non-coding sequences" refers to DNA sequences located downstream of a coding sequence and include polyadenylation recognition sequences (normally limited to eukaryotes) and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

The skilled artisan is well aware of the "codon-bias" exhibited by a specific host cell in using nucleotide codons to specify a given amino acid. Therefore, when synthesizing a gene for improved expression in a host cell, it is desirable to design the gene such that its codon usage reflects the preferred codon bias of the host cell. A survey of genes derived from the host cell where sequence information is available can determine its codon bias. Codon-optimization is well known in the art and has been described for various systems including, but not limited to yeast (Outchkourov et al., *Protein Expr Purif,* 24(1):18-24 (2002)) and *E. coli* (Feng et al., *Biochemistry,* 39(50):15399-15409 (2000)).

Definitions Applying to Reactive Solvent Extraction

As used herein, the term "reactive extraction process" refers to the process of contacting (i.e., mixing) an aqueous solution comprising glycolic acid (i.e., second phase) with a water-immiscible organic solvent (i.e., first phase) whereby the glycolic acid reacts with the tertiary trialkylamine to form an glycolic acid:trialkylamine complex. The complex is soluble in the organic phase, thereby extracting glycolic acid from the aqueous phase (i.e., second phase comprising substantial amounts of impurities) into the organic phase, forming a "glycolic acid-loaded first phase". The glycolic acid-loaded first phase is subsequently isolated from the aqueous second phase. A back extraction process is then used to extract the glycolic acid from the organic phase back into an aqueous phase (i.e. the "third phase"). The length of time and temperature used for the reactive extraction process may be adjusted to optimize the extraction efficiency. In one embodiment, the mixing period of the first and second phase is about 5 minutes to about 8 hours, preferably about 5 minutes to about 1 hour, more preferably about 10 minutes to about 30 minutes. The temperature may range from about 5° C. to about 90° C., more preferably about 25° C. to about 75° C., and most preferably about 25° C. to about 50° C.

As used herein, the term "back extraction process" refers to the process of contacting a water-immiscible organic solvent comprising glycolic acid (i.e. "glycolic acid-loaded first phase") with water (i.e. "third phase") to extract the glycolic acid from the organic phase into the aqueous phase. In one embodiment, the third phase is deionized water. After back extraction, the third phase comprises a substantially purified form of glycolic acid (substantially less mineral salts and other impurities). The glycolic acid in the third phase can be optionally isolated using a variety of techniques know in the art. The length of time and temperature used for the back extraction process may be adjusted to optimize the extraction efficiency. In one embodiment, the mixing period of the "glycolic acid-loaded first phase" and aqueous phase (i.e., third phase) is about 10 minutes to about 8 hours, preferably about 30 minutes to about 4 hours, more preferably about 30 minutes to about 60 minutes. Typically, the back extraction process occurs under pressurized conditions under a non-reactive gas (i.e., nitrogen) blanket. The pressure in the back extraction chamber may be varied but is typically less than about 100 psi (less than about 690 kPa). The temperature may range from about 5° C. to about 150° C., preferably about 100° C. to about 150° C., and most preferably about 125° C. to about 140° C.

As used herein, the terms "water-immiscible organic solvent" and "first phase" are used to describe an organic solvent mixture comprising at least one tertiary trialkylamine having the formula:

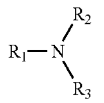

wherein $R_1$, $R_2$, and $R_3$ are independently C8 to C12 alkyl group; and at least one diluent selected from the group consisting of methyl isobutyl ketone, 1-octanol, 1-decanol, methylene chloride, 1-chlorobutane, chlorobenzene, chloroform, kerosene, toluene, mixed xylenes, tributyl phosphate, and mixtures thereof.

As used herein, the term "second phase" refers to an aqueous solution comprising glycolic acid having a pH of about 4 or less, preferably about 3 or less, and most preferably about 1 to about 2. The "second phase" is prepared by adjusting the pH of an aqueous solution comprising ammonium glycolate with a strong mineral acid, such as $H_2SO_4$. However, the addition of the strong acid increases the amount of mineral salts (an undesirable impurity) in the second phase. Extraction (i.e., reactive solvent extraction) of the glycolic acid from the second phase into an organic phase (typically as a complex with a trialkyl amine) separates the glycolic acid from the mineral salt impurities.

Definitions Applying to Thermal Salt Cracking

As used herein, the terms "direct deammoniation", "thermal salt cracking", "thermal salt decomposition", "thermal decomposition", and "salt cracking" refer to the process where a heat treatment is applied to the ammonium salt of the organic acid (i.e., ammonium glycolate) for a period of time to decompose the ammonium salt of the acid into the free organic acid and ammonia. In the present invention, thermal decomposition is used to produce primarily glycolic acid and ammonia. Various byproducts, such as glycolamide and oligomers of glycolic acid, may also be formed in the product mixture.

As used herein, the term "substantially anhydrous salt of ammonium glycolate" will refer to the resulting salt of ammonium glycolate (a liquid at room temperature) formed after removing at least about 90 wt %, preferably at least about 95 wt %, more preferably at least about 99%, and most preferably at least about 99.5 wt % of the free water from the aqueous ammonium glycolate feed stream. Typically, the "substantially anhydrous salt of ammonium glycolate" is formed an the initial step when using direct deammoniation ("thermal salt cracking"; see copending U.S. application 60/638148) to obtain glycolic acid from an aqueous solution comprising ammonium glycolate.

As used herein, the term "free water" will refer to the water that is readily removed from the feed stream prior to thermal salt cracking, where some small but measurable amount of water may not be removed from the feed stream prior to thermal salt cracking (for example, water of hydration of the ammonium glycolate salt). As used herein, the term "molten salt of ammonium glycolate" will refer to the substantially anhydrous salt of ammonium glycolate that is thermally decomposed in the presence of a strong vacuum.

As used herein the term "first liquid product mixture" or "first liquid product mixture comprising glycolic acid" refers to the product obtained after thermally decomposing a substantially anhydrous salt of ammonia glycolate as described in the present methods. The first liquid product mixture comprises glycolic acid, oligomers of glycolic acid, glycolamide, ammonium salts of oligomers of glycolic acid, and unreacted ammonium glycolate.

As used herein, the term "second liquid product mixture" refers to the product obtained by the process of 1) adding water to said first product mixture to form a rehydrated first product mixture; and 2) heating said rehydrated first product mixture whereby a portion of the glycolic acid oligomers are hydrolyzed into free glycolic acid. Subsequent processing to obtain glycolic acid from the partially deammoniated products (i.e., first product mixture or second product mixture) produces significantly less waste in comparison to ammonium glycolate that was not thermally decomposed prior to processing.

As used herein, the term "rehydrated first liquid product mixture" refers to the aqueous product obtained when water is added to the first liquid product mixture produced by the present methods.

Definitions Applying to Alcoholysis

As used herein, the term "alcoholysis" refers to the process of reacting an aqueous solution of a ammonium glycolate with a heated alcohol vapor that acts as both an esterifying agent and stripping gas, producing a vapor product stream comprising the glycolic acid ester (see copending U.S. provisional patent application 60/638,126). As used herein, the term "methanolysis" refers to the process of alcoholysis wherein the alcohol is methanol, and the corresponding ester is methyl glycolate.

As used herein, the terms "heated alcohol vapor" and "alcohol vapor feed stream" refer to the heated alcohol vapor that is contacted with the aqueous solution comprising ammonium glycolate whereby glycolic acid ester is produced; wherein the carboxylic acid ester product is in the vapor product phase ("alcoholysis"). In one embodiment, the heated alcohol vapor is a heated methanol vapor and the resulting ester vapor is a methyl glycolate vapor.

As used herein, the terms "first vapor product stream", "vapor product stream", and "alcohol vapor product stream" refer to the vapor product stream comprising the heated alcohol vapor and the glycolic acid ester (vapor) produced by alcoholysis. Methods to recover/isolate glycolic acid ester (e.g., methyl glycolate) from the first vapor product stream are well known in the art and include, but are not limited to membrane separation, adsorption, direct or indirect contact condensation (e.g., partial condenser), use of distillation column(s), and combinations. The recovered glycolic acid ester (liquid) is collected in the "first liquid product stream". As used herein, the term "first liquid product stream" refers to the liquid product comprising the glycolic acid ester recovered from the first vapor product stream (produced during the process of alcoholysis). In one embodiment, a partial condenser is used to recover the glycolic acid ester from the first vapor product stream where the most of the heated alcohol vapor passes through the partial condenser ("hot condenser")

and is subsequently recovered using a total condenser ("cold condenser"). The recovered alcohol may be recycled and reused at the starting material for the heated vapor feed stream. Any ammonia or water recovered may be optionally removed from the recovered alcohol prior to being recycled.

Synthesis of Glycolonitrile from Formaldehyde and Hydrogen Cyanide

Methods to synthesize glycolonitrile by reacting aqueous solutions of formaldehyde and hydrogen cyanide have previously been reported (U.S. Pat. Nos. 2,175,805; 2,890,238; and 5,187,301; Equation 3).

Concentrated aqueous solutions of formaldehyde (e.g., 37 wt % solutions commercially known as formalin) typically are comprised of free formaldehyde and various oligomers of formaldehyde (for example, paraformaldehyde and trixoxymethylene). The presence of formaldehyde oligomers can influence overall conversion to glycolonitrile. Hence, a method to pre-treat the formaldehyde that transforms formaldehyde oligomers to more free formaldehyde in the feed stream prior to reacting with hydrogen cyanide should increase the yield of glycolonitrile and should decrease the conversion of unwanted secondary products produced from the oligomers.

Jacobson (U.S. Pat. No. 2,175,805) discloses a method of obtaining pure glycolonitrile by the reaction of hydrogen cyanide and formaldehyde in the presence of an acidic compound followed by distillation at subatmospheric pressure (vacuum distillation step conducted at about 125° C.). The reactants are preferably mixed "in the cold" (i.e., below 26° C. to maintain the hydrogen cyanide in liquid form). Also described in U.S. Pat. No. 2,175,805 is the observation that 1) glycolonitrile decomposes at ambient temperature, and 2) glycolonitrile contacted with bases decomposes violently within hours at ambient temperature. Jacobson does not disclose pre-treatment of the concentrated aqueous formaldehyde feed prior to reacting with hydrogen cyanide.

Sexton (U.S. Pat. No. 2,890,238) discloses a method of preparing glycolonitrile in which formaldehyde is fed into an aqueous solution of HCN. The reaction is run "with efficient reflux or a closed pressure system, with the reaction allowed to go as high as 100° C." However, as described in Jacobson, glycolonitrile decomposes at room temperature. A reaction run at temperatures as high as 100° C. would be expected to result in an increase in the decomposition of the glycolonitrile. Similar to Jacobson, Sexton does not describe a method to pre-treat the formaldehyde prior to reacting with hydrogen cyanide.

Cullen et al. (U.S. Pat. No. 5,187,301) discloses a method for making iminodiacetonitrile from glycolonitrile. This reference describes how glycolonitrile can be formed in a process (either batch or continuous) by maintaining the pH of the formaldehyde above about 3, preferably in the range of about 5-7, most preferably about 5.5, with suitable acids and bases. The formaldehyde is then reacted with hydrogen cyanide in a temperature range of about 20 to 80° C., preferably about 30° C., to form glycolonitrile. However, as shown in the present examples, a reaction run within the conditions specified in Cullen et al. results in a significant amount of unreacted free formaldehyde after 2 hours of reaction time.

All of the above mentioned methods produce a purity of glycolonitrile that typically requires extensive processing steps, such as distillative purification, to remove some of the secondary products (impurities). Many of the impurities found in glycolonitrile, such as unreacted formaldehyde, have been reported to interfere with the enzymatic conversion to glycolic acid by inactivating the enzyme catalyst (U.S. Pat. Nos. 5,756,306; 5,508,181; and 6,037,155; herein incorporated in their entirety by reference).

Concentrated aqueous formaldehyde solutions are typically comprised of monomeric formaldehyde ("free formaldehyde", the desired substrate for the reaction) and oligomers of formaldehyde. Applying a heat treatment to the formaldehyde feed stream prior to reacting with hydrogen cyanide improves the purity of the resulting glycolonitrile product (See "Comparative Example A" and Examples 1-10 of the present application and copending U.S. Provisional Application 60/638,127; herein incorporated by reference). The reaction of formaldehyde with hydrogen cyanide is temperature-controlled to minimize glycolonitrile decomposition. The reaction product formed is an aqueous solution of glycolonitrile comprising significantly less unreacted formaldehyde when compared to a reaction product obtained without preheating the aqueous formaldehyde feed stream.

The resulting aqueous glycolonitrile solution (see Examples 4-8; Table 1 where glycolonitrile purity was greater than 99.9%) requires fewer, if any, post reaction purification steps (such as distillative purification), thus reducing the cost of producing glycolonitrile that is suitable for enzymatic synthesis of glycolic acid. In one embodiment, the glycolonitrile produced in the present process does not require any post reaction purification steps prior to being contacted with an enzyme catalyst having nitrilase activity. Additionally, reducing the amount of unreacted formaldehyde in the aqueous glycolonitrile solution used for enzymatic synthesis of glycolic acid should extend the enzymatic catalyst's lifespan (i.e., the number of recycle reactions). This improves the catalyst's productivity and reduces the cost for preparing glycolic acid. In one embodiment, the invention yields a glycolonitrile product that may be used directly for enzymatic conversion without purification, significantly reducing the cost of producing glycolic acid.

Suitable Reaction Conditions to Produce Improved Purity Glycolonitrile

The present method to produce glycolic acid includes a process to produce aqueous glycolonitrile by contacting heat-treated formaldehyde and hydrogen cyanide at reaction temperature suitable for glycolonitrile synthesis (see Comparative Example A and Examples 1-10). The formaldehyde is heated prior to reacting with the hydrogen cyanide to make glycolonitrile. The starting concentration of the formaldehyde is typically an aqueous solution of about 5 wt % to about 70 wt % formaldehyde. In one embodiment, the formaldehyde feed stream is comprised of about 20 wt % to about 55 wt % formaldehyde. In another embodiment, the formaldehyde feed stream is comprised of about 37 wt % formaldehyde (e.g., formalin). The formaldehyde feed stream may optionally be comprised of about 0.1 wt % to about 15 wt % (typically 6-8 wt %) methanol (an additive typically found in some 37 wt % solutions).

A base catalyst (KOH, NaOH, etc.) may be added to the aqueous formaldehyde solution prior to heating the aqueous formaldehyde feed stream. As exemplified herein, sodium hydroxide may be added to the aqueous formaldehyde feed stream prior to heating the formaldehyde feed stream. In one embodiment, the molar ratio of NaOH:formaldehyde in the heated aqueous formaldehyde feed stream is about 1:50 to about 1:2000. In another embodiment, the molar ratio of NaOH:HCHO in the heated aqueous formaldehyde feed stream is about 1:100 to about 1:2000.

The formaldehyde feed stream may be heated to a temperature of about 35° C. to about 200° C. In one embodiment, the formaldehyde feed stream is heated to a temperature of about 90° C. to about 150° C. In another embodiment, the formaldehyde feed stream is heated to a temperature of about 100° C. to about 125° C.

The optimal length of time the formaldehyde is heat-treated can be easily determined and may be adjusted depending upon the selected temperature in combination with the specific design of the heat treatment system and the reactor. The length of the heat treatment is chosen to maximize the amount of monomeric formaldehyde in the heated feed stream. Hence, the amount of time the formaldehyde is heated to the desired temperature may be easily determined. As used herein, the term "determinable period of time" is used to describe the amount of time the formaldehyde feed stream is heated to the specified temperature. Typically, the heat treatment period can last from about 10 seconds to about 24 hours, preferably about 10 seconds to about 6 hours, more preferably about 10 seconds to about 20 minutes, and most preferably about 2 minutes to about 10 minutes. In one embodiment, the heat treatment time is about 2 minutes to about 10 minutes in the presence of a base catalyst. The heated formaldehyde is then promptly fed to the reaction chamber.

The hydrogen cyanide feed stream is typically added at a rate sufficient to maintain a slight molar excess of hydrogen cyanide relative to the amount of formaldehyde added to the reaction chamber. In one embodiment, the molar ratio of hydrogen cyanide to formaldehyde is at least about 1.01:1, preferably no greater than about 10:1. In another embodiment, the molar ratio of HCN to formaldehyde is about 1.01:1, more preferably no greater than about 2:1. In a further embodiment, the molar ratio of HCN to formaldehyde is about 1.05:1 to about 1.15:1.

The reaction chamber may optionally be pre-charged with hydrogen cyanide so that the formaldehyde is immediately in contact with the hydrogen cyanide upon addition to the reaction chamber. Pre-charging the reaction chamber with hydrogen cyanide aids in maintaining the slight excess of hydrogen cyanide during the reaction. One skilled in the art recognizes that when an HCN pre-charge is used, the molar ratio of the HCN to formaldehyde rapidly transitions from infinity to the more sustainable ration of 10:1 or less, preferably 2:1 or less, more preferably about 1.01:1 to about 1.15:1, and most preferably about 1.01:1 to about 1.05:1.

The temperature of the reaction chamber (ire., the temperature suitable for producing glycolonitrile) is typically maintained about 70° C. or less in order to minimize glycolonitrile decomposition. In one embodiment, the reaction temperature is between about −20° C. to about 70° C. In another embodiment, the reaction temperature is about 0° C. to about 70° C. In yet another embodiment, the reaction chamber temperature is about 0° C. to about 55° C. In a further embodiment, the reaction temperature is about 10° C. to about 30° C. In yet a further embodiment, the reaction temperature is about 20° C. to about 25° C.

Atmospheric pressure is satisfactory for carrying out the reaction of formaldehyde and hydrogen cyanide, and hence pressures of from about 0.5 to about 10 atmospheres (50.7 kPa to 1013 kPa) are preferred. Higher pressures, up to 20,000 kPa or more may be used, if desired, but any benefit that may be obtained thereby would probably not justify the increased cost of such operations.

The pH in the glycolonitrile synthesis reaction chamber is typically about 3 to about 10, preferably about 5 to about 8.

The present glycolonitrile synthesis reaction can be run in continuous, batch, or fed batch mode. The fed batch reaction typically is run for about 10 seconds to about 24 hours, preferably about 30 minutes to about 8 hours, more preferably about 0.5 hours to about 4 hours.

Stabilization of Glycolonitrile Under Acidic Conditions

The glycolonitrile produced by the present process steps is subsequently contacted with the present enzyme catalysts and converted into glycolic acid (typically in the form of the ammonium salt of glycolic acid). In one embodiment, the glycolonitrile produced by the present process steps may be stabilized (typically when the glycolonitrile is to be stored for a period of time prior to enzymatic conversion) with a mineral acid (e.g., HCl, $H_2SO_4$, or $H_3PO_4$) to maintain the pH of the glycolonitrile below 7 (glycolonitrile has been reported to decompose under basic conditions). The need to stabilize the glycolonitrile determines on a variety of factors including storage time and conditions. One of skill in the art can easily determine whether or not the glycolonitrile produced using the present process steps should be acid stabilized. In another preferred embodiment, glycolic acid is added to the glycolonitrile mixture obtained by the present method to maintain the pH of the glycolonitrile below 7. In a further embodiment, the amount of glycolic acid added is sufficient to maintain the pH of the glycolonitrile below about 6, preferably below about 5, more preferably below about 4, and most preferably below about 3.5. Stabilization with glycolic acid is a preferred embodiment in the instance where the glycolonitrile is subsequently converted to glycolic acid using an enzyme catalyst. The use of glycolic acid to adjust the pH in this instance avoids the addition of a mineral acid, where, upon conversion of glycolonitrile to glycolic acid, the presence of a mineral acid and/or the production of the corresponding mineral acid salt may require a purification step to remove the mineral acid and/or the corresponding salt from the glycolic acid product. The pH of the acid-stabilized glycolonitrile solution is typically adjusted with a base to a more neutral pH range (i.e. pH of about 6 to about 8) prior to enzymatic conversion of glycolonitrile to glycolic acid (typically in the form of the ammonium salt of glycolic acid).

*Acidovorax facilis* 72W (ATCC 55746) Nitrilase

The *A. facilis* 72W nitrilase (EC 3.5.5.1) is a robust catalyst for producing carboxylic acids from aliphatic or aromatic nitriles (WO 01/75077; U.S. Pat. No. 6,870,038; and Chauhan et al., supra). It has also been shown to catalyze the conversion of α-hydroxynitriles (i.e., glycolonitrile) to α-hydroxycarboxylic acids (i.e., glycolic acid) (see U.S. Pat. Nos. 6,383,786 and 6,416,980). However, nitrilase catalysts having improved nitrilase activity and/or stability (relative to the *A. facilis* 72W nitrilase) when converting glycolonitrile to glycolic acid would reduce the cost of manufacturing glycolic acid. As such, a method of producing glycolic acid using an improved nitrilase catalyst is needed to reduce the cost of manufacturing glycolic acid.

All known nitrilases, including the *A. facilis* 72W nitrilase, have a nucleophilic cysteine in the enzyme active site (Cowan et al., *Extremophiles,* 2:207-216 (1998); Pace, H. and Brenner, C., *Genome Biology,* 2(1):reviews 1-9 (2001); and Chauhan et al., supra) and all are susceptible to inactivation by thiol reagents (1.0 mM concentrations of copper chloride, silver nitrate, mercuric acetate, or ferric chloride each produced major decreases in *A. facilis* 72W nitrilase enzyme activity). Cysteine residues are also capable of being irreversibly oxidized to sulfinic acids, resulting in a loss of enzyme activity. Despite the sensitivity of nitrilase enzymes to various inactivating mechanisms, immobilized *A. facilis* 72W cells are robust, capable of retaining much of their nitrilase activity after numerous recycle reactions (U.S. Pat. No. 6,870,038).

Sequence comparisons of the *A. facilis* 72W nitrilase to other bacterial nitrilases have been reported (U.S. Pat. No. 6,870,038; Chauhan et al., supra). The 72W nitrilase has several conserved signature domains including a 16-amino acid region near the amino terminus (amino acid residues 40-55 of SEQ ID NO:6) and the catalytic region (SEQ ID NO: 39; see amino acid residues 160-173 of SEQ ID NO:6) containing the essential cysteine residue. This cysteine residue (Cys164 of SEQ ID NO:6), along with conserved glutamic acid (Glu48 of SEQ ID NO:6) and lysine residues (Lys130 of SEQ ID NO:6), form the catalytic triad motif found in all nitrilases (Pace, H., and Brenner, C., supra).

Nitrilase Enzymes Providing Improved Nitrilase Activity

Several mutant nitrilases (polypeptides having nitrilase activity) derived from the *A. facilis* 72W nitrilase have been previously reported (U.S. Pat. No. 10/919182; herein incorporated by reference). In U.S. Pat. No. 10/919182, various mutant nitrilases were selected and screened for relative improvements (relative to the activity of recombinantly expressed, native 72W nitrilase) in nitrilase activity for converting 3-hydroxynitriles to 3-hydroxyacids.

The expression system used with the nitrilase mutants described in U.S. Ser. No. 10/919,182 is based on the plasmid pTrcHis2-TOPO® and the *E. coli* host TOP10 (both from Invitrogen, La Jolla, Calif.). The activity of nitrilase mutants F168L (residue 168 changed from Phe to Leu in SEQ ID NO: 6), F168V (residue 168 changed from Phe to Val; SEQ ID NO: 32), F168K (residue 168 changed from Phe to Lys; SEQ ID NO: 26), T210A (residue 210 changed form Thr to Ala; SEQ ID NO: 34), and T210C (residue 210 change from Thr to Cys; SEQ ID NO: 36) were compared to the native enzyme ("control"; SEQ ID NO: 6) in the same expression system using the method described in Example 12. Mutants F168L, T210A, and T210C, which were initially identified as possibly having significantly improved nitrilase activity when converting GLN to GLA, were later found to have similar nitrilase activity to the 72W nitrilase control. Unexpectedly, two of the mutant nitrilases (F168K, Phe168→Lys; F168V, Phe168→Val) described in U.S. Ser. No. 10/919,182 (herein represented by SEQ ID NOs: 26 and 32; respectively) also exhibited a significant improvement in nitrilase activity when converting glycolonitrile (a 2-hydroxynitrile) to glycolic acid. However, the other mutant nitrilases described in U.S. Ser. No. 10/919,182 (e.g. T210A, SEQ ID NO: 34; T210C, SEQ ID NO: 36) did not show a significant improvement in nitrilase activity when converting glycolonitrile to glycolic acid.

As described in Examples 13-17 of the present application and in copending U.S. Provisional Application 60/638,176 (herein incorporated by reference), error-prone PCR and targeted saturation mutagenesis was used to randomly mutate the native 72W nitrilase coding sequence (SEQ ID NO: 5). Mutations that resulted in an amino acid substitution at amino acid residue positions 168 (phenylalanine in the wild type sequence) and 201 (leucine in the wild type sequence) appeared to increase nitrilase activity significantly (Examples 15-17). As used herein, the term "amino acid residue position" refers to the amino acid found at a particular location relative to the reference sequence (SEQ ID NO: 6) as measured from the N-terminal methionine residue. Targeted saturation mutagenesis was conducted to evaluate all amino acid substitutions at both residue positions (168 and 201). Several additional mutants were identified having a significant improvement nitrilase activity of converting glycolonitrile to glycolic acid (e.g. in the form of the ammonium glycolate salt under the present reaction conditions). In one embodiment, suitable nitrilases useful in the present process comprise a nucleotide sequence encoding a polypeptide having an amino acid of SEQ ID NO: 6 with at least one mutation that results in at least one amino acid substitution selected from the group consisting of:

a) a substitution of lysine, methionine, threonine, or valine at amino acid position 168; and
b) a substitution of glutamine, glycine, histidine, lysine, asparagine, serine, alanine, cysteine, or threonine at amine acid position 201; wherein said mutant has at least a 1.5-fold improvement in nitrilase activity when converting glycolonitrile to glycolic acid.

In another embodiment, suitable mutant nitrilase useful in the present process have an amino acid sequence selected from the group consisting of SEQ ID NOs: 8, 10, 12, 14, 16, 18, 20, 22, 24, 26, 28, 30, and 32. In yet another embodiment, suitable mutant nitrilase useful in the present process have a nucleotide sequence selected from the group consisting of SEQ ID NOs: 7, 9, 11, 13, 15, 17, 19, 21, 23, 25, 27, 29, and 31.

Nitrilase activity was calculated by dividing the measured units of activity (U) by catalyst weight. The catalyst weight can be measured in terms of purified protein weight, wet cell weight, dry cell weight or weight of the immobilized catalyst (i.e., using carrageenan and/or GA/PEI-crosslinked catalyst/alginate beads). In the present invention, the nitrilase activity was reported as units of activity per gram of dry cell weight (U/g DCW) or units of activity per gram of catalyst bead (immobilized catalyst comparisons). With nitrilase activity comparisons based on dry cell weight as the unit catalyst weight, the level of nitrilase protein production must be considered. The expression levels of nitrilase enzyme between the various transformants and their respective controls were measured and observed to be essentially identical (i.e., when compared in the same genetic background). Thus, improvements in the reported nitrilase activity for the various mutants were attributed to structural modifications to the enzymes.

The coding sequences of the mutant nitrilases (and also of the *A. facilis* 72W (ATCC 55746) nitrilase control) were expressed in identical vector backgrounds (pTrcHis2-TOPO® or pUC19) and hosts: *E. coli* TOP10 (Invitrogen), *E. coli* FM5 (ATCC 53911), or *E. coli* MG1655 (ATCC 47076). Relative improvements were based on comparisons to the appropriate control using the same vector and host background. SDS-PAGE analyses (as quantified using laser densitometry) demonstrated that nitrilase protein expression levels in each mutant (and control) were essentially equal (as expected due to the identical expression system and host used). The relative enzyme activity was reported as the fold increase in nitrilase activity measured for the various mutant catalysts relative to the nitrilase activity measured in the respective *E. coli* control transformant expressing the *A. facilis* 72W nitrilase (SEQ ID NO: 6).

For unimmobilized catalysts, nitrilase activity of the mutant nitrilases (U/g dry cell weight) was determined by measuring the rate of conversion of glycolonitrile to glycolic acid (μmol GLA/min) at 25° C. per gram of dry cell weight. For immobilized catalyst comparisons, activity was determined by measuring the rate of conversion of glycolonitrile to glycolic acid (μmol GLA/min) at 25° C. and reported as units of nitrilase activity per gram of immobilized cell catalyst bead (U/g bead). One unit of nitrilase activity (U) is equivalent to production of 1 micromole glycolic acid/min at 25° C. (μmol GLA/min).

For a particular mutant nitrilase, point substitution mutations within the DNA coding region and the resulting amino acid change are specified with reference to the *Acidovorax facilis* 72W amino acid sequence (SEQ ID NO: 6), using one of the following formats:

1. Extended format: the wild-type amino acid is provided (using the standard 3-letter abbreviation) along with the corresponding amino acid residue position within SEQ ID NO:6 followed by the new amino acid found within the mutant at the same residue position. For example, "Phe168 to Lys" or "Phe168→Lys" describes a mutation in the SEQ ID NO:6 at amino acid residue position 168 where phenylalanine was changed to lysine as a result of the mutation.
2. Short-hand format: the wild-type amino acid (denoted by the standard single letter abbreviation) is followed by the amino acid residue position of SEQ ID NO:6 followed by the mutant amino acid (also denoted by the standard single letter abbreviation). For example, "F168K" describes a mutation in SEQ ID NO: 6 at amino acid residue position 168 where phenylalanine was changed to lysine as a result of the mutation.

Hydrolysis of Glycolonitrile to Glycolic Acid Using a Nitrilase Catalyst

The enzymatic conversion of glycolonitrile to glycolic acid (in the form of the acid and/or the corresponding ammonium salt) was performed by contacting an enzyme catalyst (comprising a polypeptide having nitrilase activity) with a suitable aqueous reaction mixture comprising glycolonitrile using a suitable set of enzymatic reaction conditions (pH range, temperatures, concentrations, etc.) described below. In one embodiment, whole recombinant microbial cells can be used as an enzyme catalyst without any pretreatment. In another embodiment, the microbial cell catalyst can be added directly to a reaction mixture, or maintained separately from the bulk reaction mixture using hollow-fiber membrane cartridges or ultrafiltration membranes. In a further embodiment, the microbial cells can be immobilized in a polymer matrix (e.g., carrageenan or polyacrylamide gel (PAG) particles) or on an insoluble solid support (e.g., celite) to facilitate recovery and reuse of the enzyme catalyst (U.S. Pat. No. 6,870,038; herein incorporated by reference). In yet a further embodiment, purified or partially-purified enzyme(s) can also be isolated from the whole cells and used directly as a catalyst, or the enzyme (s) can be immobilized in a polymer matrix or on an insoluble support. Methods for the immobilization of cells or for the isolated enzymes have been widely reported and are well known to those skilled in the art (Methods in Biotechnology, Vol. 1: *Immobilization of Enzymes and Cells;* Gordon F. Bickerstaff, Editor; Humana Press, Totowa, N.J., USA; 1997). The immobilization of the *A. facilis* 72W nitrilase catalyst has previously been reported (U.S. Pat. No. 6,870,038).

The concentration of enzyme catalyst in the aqueous reaction mixture depends on the specific activity of the enzyme catalyst and is chosen to obtain the desired rate of reaction. The wet cell weight of the microbial cells used as catalyst in hydrolysis reactions typically ranges from 0.001 grams to 0.250 grams of wet cells per mL of total reaction volume, preferably from 0.002 grams to 0.050 grams of wet cells per mL.

The temperature of the glycolonitrile hydrolysis reaction is chosen to control both the reaction rate and the stability of the enzyme catalyst activity. The temperature of the reaction may range from just above the freezing point of the reaction mixture (approximately 0° C.) to about 65° C., with a preferred range of reaction temperature of from about 5° C. to about 35° C. The microbial cell catalyst suspension may be prepared by suspending the cells in distilled water, or in a aqueous solution of a buffer which will maintain the initial pH of the reaction between about 5.0 and about 10.0, preferably between about 5.5 and about 8.0, more preferably between about 5.5 and about 7.7, and most preferably about 6.0 to about 7.7. As the reaction proceeds, the pH of the reaction mixture may change due to the formation of an ammonium salt of the carboxylic acid from the corresponding nitrile functionality. The reaction can be run to complete conversion of glycolonitrile with no pH control, or a suitable acid or base can be added over the course of the reaction to maintain the desired pH.

Glycolonitrile was found to be completely miscible with water in all proportions at 25° C. In cases where reaction conditions are chosen such that the solubility of the substrate (i.e., an α-hydroxynitrile) is also dependent on the temperature of the solution and/or the salt concentration (buffer or product glycolic acid ammonium salt, also known as ammonium glycolate) in the aqueous phase, the reaction mixture may initially be composed of two phases: an aqueous phase containing the enzyme catalyst and dissolved α-hydroxynitrile, and an organic phase (the undissolved α-hydroxynitrile). As the reaction progresses, the α-hydroxynitrile dissolves into the aqueous phase, and eventually a single phase product mixture is obtained. The reaction may also be run by adding the α-hydroxynitrile to the reaction mixture at a rate approximately equal to the enzymatic hydrolysis reaction rate, thereby maintaining a single-phase aqueous reaction mixture, and avoiding the potential problem of substrate inhibition of the enzyme at high starting material concentrations.

Glycolic acid may exist in the product mixture as a mixture of the protonated carboxylic acid and/or its corresponding ammonium salt (dependent on the pH of the product mixture; pKa of glycolic acid is about 3.83), and may additionally be present as a salt of the carboxylic acid with any buffer that may additionally be present in the product mixture. Typically, the glycolic acid produced is primarily in the form of the ammonium salt (pH of the glycolonitrile hydrolysis reaction is typically between about 5.5 and about 7.7). The glycolic acid product may be isolated from the reaction mixture as the protonated carboxylic acid, or as a salt of the carboxylic acid, as desired.

The final concentration of glycolic acid in the product mixture at complete conversion of glycolonitrile may range from 0.001 M to the solubility limit of the glycolic acid product. In one embodiment, the concentration of glycolic acid will range from about 0.10 M to about 5.0 M. In another embodiment, the concentration of glycolic acid Will range from about 0.2 M to about 3.0 M.

Glycolic acid may be recovered in the form of the acid or corresponding salt using a variety of techniques including, but not limited to ion exchange (Example 38), electrodialysis, reactive solvent extraction (Examples 39-61), polymerization, thermal decomposition (Examples 62-66), alcoholysis (Examples 67-74), and combinations thereof.

Microbial Expression

The present nitrilase mutants may be produced in heterologous host cells, preferably in microbial hosts. Particularly useful in the present invention will be cells that are readily adaptable to large-scale fermentation methods. Such organisms are well known in the art of industrial bioprocessing, examples of which may be found in *Recombinant Microbes for Industrial and Agricultural Applications,* Murooka et al., eds., Marcel Dekker, Inc., New York, N.Y. (1994), and include fermentative bacteria as well as yeast and filamentous fungi. Host cells may include, but are not limited to *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccha-*

*romyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. Particularly preferred is *E. coli*. Examples of suitable *E. coli* host cells in which a mutant nitrilase gene can be expressed include, but are not limited to, host cells specified herein and MG1655 (ATCC 47076), FM5 (ATCC 53911), W3110 (ATCC 27325), MC4100 (ATCC 35695), W1485 (ATCC 12435), and their derivatives. In another aspect, the preferred *E. coli* host strains are MG1655 (ATCC 47076) or FM5 (ATCC 53911), Heterologous expression of the *A. facilis* 72W nitrilase has previously been reported (Chauhan et al., supra and U.S. Pat. No. 6,870,038). Chauhan et al. report an *E. coli* strain (*E. coli* SS1001 (ATCC PTA-1177)) that expressed active *A. facilis* 72W nitrilase (SEQ ID NO: 38). The coding sequence of the recombinantly expressed (*E. coli* SS1001) nitrilase contained two minor sequence changes in comparison to the wild-type 72W nitrilase sequence (SEQ ID NOs: 5 and 6). The start codon was changed from GTG to ATG to facilitate recombinant expression and an artifact was introduced during cloning that resulted in a single amino acid change near the C-terminal (Pro367 [CCA]→Ser [TCA]).

Recombinant expression in an industrially-suitable host has several advantages. First, the genetic toolbox for many of the commonly used production hosts is usually well developed in comparison to the genetic tools available for many of the microorganisms from which the gene of interest was obtained. Recombinant expression in these hosts is normally more cost effective than expression in the native host. For example, it has been shown that *A. facilis* 72W cells grow on glycerol, a relatively expensive carbon substrate, when grown by fermentation, and have not been successfully grown using inexpensive glucose. In contrast, *E. coli* transformants can be grown on glucose to the same cell density as *A. facilis* 72W cells in about half the time, significantly reducing biocatalyst production costs (U.S. Pat. No. 6,870,038).

Microbial expression systems and expression vectors containing regulatory sequences that direct high level expression of foreign proteins are well-known to those skilled in the art. These could be used to construct chimeric genes for production of the gene products of the present mutant nitrilases. These chimeric genes could then be introduced into appropriate microorganisms via transformation to provide high level expression of the mutant nitrilase enzymes. The nucleic acid molecules of the present invention are used to produce gene products having enhanced or altered nitrilase activity levels relative to that of the native *A. facilis* 72W nitrilase. In one aspect, the polypeptides encoded by the present mutant genes provide at least a 1.5 fold improvement in nitrilase activity (as compared to the activity of the *A. facilis* 72W nitrilase "control" represented by SEQ ID NO: 6) for converting glycolonitrile to glycolic acid.

Chimeric genes will be effective in altering the properties of a host cell. For example, introducing at least one copy of chimeric genes encoding the present nitrilases under the control of the appropriate promoters into a host cell gives the host cell an improved ability to convert glycolonitrile to glycolic acid. The chimeric genes will comprise suitable regulatory sequences useful for driving gene expression of the present mutant nitrilase sequences. Suitable regulatory sequences may include, but are not limited to promoters, translation leader sequences, and ribosomal binding sites. It is preferred if these sequences are derived from the host organism; however, the skilled person will recognize that heterologous regulatory sequences may also be used.

Chimeric genes can be introduced into an appropriate host by cloning it into a suitable expression vector. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the coding sequence that harbors transcriptional initiation controls and a region 3' of the DNA fragment which controls transcriptional termination. It is most preferred when both control regions are derived from genes homologous to the host cell, although such control regions need not be derived from the genes native to the specific species chosen as a production host.

In one embodiment, the regulatory sequences will include a promoter. Promoters may be constitutive or inducible. Inducible promoters are generally responsive to a specific stimulus (e.g., IPTG or lactose inducing the lac promoter). Inducible promoters may be responsive to a variety of stimuli, including, chemicals, growth cycle, changes in temperature, changes in pH and changes in osmolarity, to name only a few.

Initiation control regions or promoters that are useful to drive expression of the present mutant nitrilases in the desired host cell are numerous and familiar to those skilled in the art, including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $IP_L$, $IP_R$, T7, tac, $P_{BAD}$, npr, and trc (particularly useful for expression in *Escherichia coli*). Additional examples of promoters particularly suitable for driving expression in *E. coli* include, but are not limited to the tryptophan operon promoter Ptrp of *E. coli,* a lactose operon promoter Plac of *E. coli,* a Ptac promoter of *E. coli,* a phage lambda right promoter $P_R$, a phage lambda left promoter $P_L$, a T7 promoter, and a promoter of the GAP gene from *Pichia pastoris,* or is at least one promoter isolated from the group of microorganisms selected from the group consisting of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Pichia, Zygosaccharomyces, Kluyveromyces, Candida, Hansenula, Dunaliella, Debaryomyces, Mucor, Torulopsis, Methylobacteria, Bacillus, Escherichia, Pseudomonas, Rhizobium,* and *Streptomyces.*

Termination control regions may also be derived from various genes native to the preferred hosts. Optionally, a termination site may be unnecessary; however, it is most preferred if included.

Additionally, the inserted genetic material may include a ribosome binding site (RBS). The ribosome binding site may be from a phage lambda CII gene or is selected from the group consisting of ribosome binding sites from a gene of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Zygosaccharomyces, Pichia, Kluyveromyces, Candida, Hansenula, Dunaliella, Debaryomyces, Mucor, Torulopsis, Methylobacteria, Bacillus, Escherichia, Pseudomonas, Rhizobium,* and *Streptomyces.*

Optionally, the gene products may preferably be a secreted product of the transformed host. Secretion of desired proteins into the growth media simplifies purification procedures and reduces costs. Secretion signal sequences are often useful in facilitating the active transport of expressible proteins across cell membranes. A transformed host capable of secretion may be created by incorporating in the host a DNA sequence that codes for a secretion signal. Methods for choosing appropriate signal sequences are well known in the art (see for example EP 546049; WO 93/24631). The secretion signal DNA may be located between the expression-controlling DNA and the instant coding sequence or coding sequence fragment, and in reading frame with the latter.

Method to Improve Nitrilase Stability and Productivity When Converting Glycolonitrile to Glycolic Acid Stabilizing Agents Glycolonitrile can be synthesized by reacting formaldehyde with hydrogen cyanide (U.S. Pat. Nos. 2,175,805, 2,890,238, 5,187,301, and copending U.S. Provisional Patent Application 60/638,127). Depending upon the purity of the reactants and the reaction conditions used to make glycolonitrile, a variety of impurities may exist in the final product. These impurities can interfere with the efficiency of converting glycolonitrile to glycolic acid. In one embodiment, the aqueous glycolonitrile solution may be optionally treated to remove undesirable impurities prior to being enzymatically converted to glycolic acid. In a preferred embodiment, the glycolonitrile produced in the present process does not require any additional purification steps prior to contact with the present enzyme catalysts.

Another method to increase the stability/productivity of an enzyme catalyst is the addition of one or more compounds that will react with undesirable compounds in the glycolonitrile solution that may interfere with the catalyst stability and/or productivity (See copending U.S. Patent Application 60/638,176; herein incorporated by reference). The undesirable compounds include, but are not limited to formaldehyde, formaldehyde-derived impurities, formaldehyde-derived oligomers and polymers, glycolamide, glycolamide-derived impurities, hydrogen cyanide-derived impurities, hydrogen cyanide-derived oligomers and polymers, glycolonitrile-derived impurities, glycolonitrile-derived oligomers and polymers, glycolide, linear oligomers of glycolic acid, and possibly oxygen (reactions conducted under substantially oxygen free conditions improved catalyst stability). The undesirable compounds may also include those that 1) react with and inactivate the nitrilase catalyst, 2) compete with glycolonitrile in the reaction, 3) react with glycolonitrile or glycolic acid to form unwanted byproducts, or 4) adversely affect the recombinant host cell (i.e. promote cell lysis). Examples of suitable compounds that can be added to the glycolonitrile reaction mixture may include, but are not limited to thiosulfates (e.g. potassium thiosulfate, $K_2S_2O_3$), dithionites (e.g., sodium dithionite, $Na_2S_2O_4$), and cyanide compounds (e.g. HCN, NaCN, KCN, etc.). In one embodiment, the compound is added to the glycolonitrile reaction mixture before, during, or after the addition of the enzyme catalyst. In another embodiment, the compound is added to the reaction mixture so that the final concentration in the reaction mixture is at least about 0.001 M to less than about 5 wt % of the reaction mixture. In a further embodiment, the compound is added to the reaction mixture so that the final concentration is at least about 0.01 M. In yet a further embodiment, the compound is added to the reaction mixture so that the final concentration of compound is about 0.01 M to about 1 M.

In a further aspect of the invention, the present process is conducted under substantially oxygen free conditions. As used herein, the terms "oxygen free conditions", "oxygen free atmosphere" and "substantially oxygen free conditions" refers to a reaction condition where a non-reactive gas, such as nitrogen, is used to purge and/or blanket the reaction vessel so that molecular oxygen ($O_2$) is not present during present process. One of skill in the art recognizes that trace amounts of molecular oxygen may exist under substantially oxygen free conditions. In one aspect, the term "substantially oxygen free" means a reaction condition where the molecular oxygen concentration is less than about 5%, preferably less than 2%, more preferably less than 1%, and most preferably less than 0.1% of the gas in the reaction vessel. In another aspect, the present process is conducted under substantially oxygen free conditions where nitrogen ($N_2$) is used to blanket the aqueous reaction mixture in the reaction vessel.

Controlling the Concentration of Glycolonitrile

Another method to increase the nitrilase stability is controlling the maximum concentration of glycolonitrile in the aqueous reaction mixture (U.S. 60/638176). As described previously, glycolonitrile dissociates in polar solvents to release formaldehyde and hydrogen cyanide. Formaldehyde in the reaction mixture may react with the enzyme catalyst leading to premature inactivation and a decrease in catalyst productivity. Controlling the concentration of the glycolonitrile in solution can increase both the catalyst stability and productivity of the catalyst (grams of glycolic acid produced per gram of catalyst). As shown in Examples 22-25 (Table 10), a nitrilase catalyst derived from the *Acidovorax facilis* 72W rapidly loses its activity in reactions that contain 3 M glycolonitrile after only 3 recycle reactions. Decreasing the concentration to 1 M and/or the stepwise addition of 3 M glycolonitrile in 1 M increments (added after the previous additions of glycolonitrile have been converted to ammonium glycolate) increases the catalyst productivity significantly (Table 10). In one embodiment, a stepwise addition (aliquots) of glycolonitrile to the aqueous reaction mixture increases the productivity of the catalyst. In another embodiment, the glycolonitrile is added to the aqueous reaction mixture in a stepwise fashion so that the total concentration of glycolonitrile remains about 1 M or less during the reaction.

As shown in Example 25, a continuous addition of glycolonitrile also increases the catalyst productivity over several recycle reactions. In one embodiment, the method to produce ammonium glycolate from glycolonitrile uses a continuous addition of glycolonitrile. In another embodiment, the rate of glycolonitrile addition is at least 5-times the Km of the catalyst. The present catalysts typically have a Km for glycolonitrile of approximately 1 mM (wild type *A. facilis* 72W; SEQ ID NO: 6) to about 2.7 mM. As known in the art, a substrate concentration of approximately 5-times the Km value (i.e., 5×2.7 mM=13.5 mM) results in a reaction rate that is approximately 97% of the maximum reaction rate (Vmax). In yet another embodiment, the glycolonitrile feed rate is controlled to maintain a glycolonitrile concentration in the reaction mixture of about 5 mM to about 1 M, preferably about 100 mM to about 1 M, more preferably about 100 mM to about 500 mM.

Control of pH

Reactions using the nitrilase catalysts of the present process are typically run at a pH ranging from about 5 to about 10, preferably between 5.5 and about 8, more preferably about 5.5 to about 7.7, and most preferably about 6 to about 7.7.

Industrial Production of the Microbial Catalyst

Where commercial production of the present nitrilases using the present mutated nitrilase genes is desired, a variety of culture methodologies may be used. Fermentation runs may be conducted in batch, fed-batch, or continuous mode, methods well-known in the art (Thomas D. Brock in *Biotechnology: A Textbook of Industrial Microbiology,* Second Edition (1989) Sinauer Associates, Inc., Sunderland, Mass., (1989); Deshpande, Mukund V., *Appl. Biochem. Biotechnol.* 36(3): 227-234 (1992)).

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch culturing methods are common and well known in the art and examples may be found in Brock (supra) and Deshpande (supra).

Commercial production of the present nitrilase catalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end cell concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady-state growth conditions and thus the cell loss due to media being drawn off must be balanced against the cell growth rate in the culture. Methods of modulating nutrients and growth factors for continuous culture processes, as well as techniques for maximizing the rate of cell formation, are well known in the art of industrial microbiology and a variety of methods are detailed by Brock (supra).

Fermentation media in the present invention must contain suitable carbon substrates. Suitable substrates may include, but are not limited to monosaccharides such as glucose and fructose, disaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Hence, it is contemplated that the source of carbon utilized in the present invention may encompass a wide variety of carbon-containing substrates and will only be limited by the choice of organism.

Analysis of Glycolic Acid and Glycolonitrile

Analytical methods suitable for analyzing the production of glycolic acid are well-known in the art including, but not limited to $^{1}$H NMR, $^{13}$C NMR, HPLC, CE, GC, and MS. For example, HPLC analysis was used to determine the amount of glycolic acid production using a refractive index detector and a Bio-Rad HPX-87H column (30 cm×7.8 mm dia.) and 0.01 N sulfuric acid at 1.0 mL/min (isocratic) as a mobile phase at 50° C. The HPLC method was suitable for quantification of both the substrate (glycolonitrile) and product (glycolic acid).

Methods to Recover Glycolic Acid from Ammonium Glycolate

There are many methods that can be used to recover/isolate an α-hydroxyacid (i.e., glycolic acid) from an aqueous solution comprising ammonium glycolate including, but not limited to ion exchange (anionic and/or cationic), electrodialysis, reactive solvent extraction, alcoholysis (esterification followed by hydrolysis of the glycolic acid ester into glycolic acid), thermal salt cracking, and combinations thereof.

Ion Exchange (Cationic)

Cationic ion exchange is a reversible process is which a dissolved ionic species is taken up by a solid in a stoichiometric manner. Cationic ion exchange is well known in the art. In the present process, ammonium glycolate is fed to the cationic ion exchange resin where the ammonium ion is exchanged with a proton, forming glycolic acid (see Example 38). The glycolic acid passes through the column and is collected.

Once the resin is saturated with ammonium ion, regeneration with an acid, for example sulfuric acid, will produce the byproduct, ammonium sulfate salt. The cationic exchange can be performed in batches, using a simulated moving bed or carrousel (see *Perry's Chemical Engineers' Handbook,* 7$^{th}$ ed., Perry, Robert H., Green, Dow W., and Maloney, James O., editors; McGraw Hill Companies, Inc., New York, N.Y., 1997; hereinafter "Perry's"). Selection of the resin may impact feed concentration, which may range from about 0.02 wt % salt to about 50 wt % ammonium glycolate, preferably about 0.02 wt % to about 40 wt %. The regeneration acid used typically ranges from about 0.5 wt % to about 20 wt %.

Ion Exchange (Anionic)

Anionic ion exchange is also well known in the art. Anionic exchange is similar to cationic exchange except that a weak anionic resin is used (see Perry's, supra). Once again, selection of the resin may impact feed concentration, which may range from about 0.02 wt % to about 90 wt % ammonium glycolate, preferably about 0.02 wt % to about 40 wt %. Regeneration of the resin would typically use a weak acid.

Solvent Extraction (Reactive)

One method that has been used to isolate carboxylic acids is reactive extraction. This method has been reported to be useful for extracting lactic acid from ammonium lactate (Wasewar et al., *J. Biotechnol.,* 97:59-68 (2002)). Reactive extraction involves the use of a reactive organic solvent (i.e., an amine) to complex with the acid in the aqueous phase. The first step in the process typically involves acidification of the aqueous solution containing the salt of the desired acid. The acidified aqueous solution is then contacted with an organic solvent typically comprised of a reactive tertiary amine and one or more diluents. The reactive amine (typically a tertiary C8-C10 trialkylamine such as Alamine® 336, Cognis Corp, Cincinnati, Ohio) reacts with the carboxylic acid forming an acid/amine complex that is preferentially soluble in the organic phase (Tamada et al., *Ind. Eng. Chem. Res.* 29:1319-1326 (1990); Tamada et al., *Ind. Eng. Chem. Res.* 29:1327-1333 (1990)). The use of a tertiary alkylamine typically provides much higher distribution coefficients than would be obtainable with normal solvent extraction. Back extraction is then used to recover the acid from the organic phase.

Inci, I. (*Chem. Biochem. Eng. Q.,* 16(2):81-85 (2002); Inci, I. and Uslu, H., *J. Chem. Eng. Data,* 50:536-540 (2005)) report the use of reactive amine solvents for the extraction of glycolic acid. However, these experiments reported the extraction coefficients of pure glycolic acid dissolved in pure water. Inci does not illustrate or teach a process to obtain glycolic acid from a complex aqueous matrix (e.g., aqueous solutions of glycolic acid comprising significant amounts of mineral salts and other impurities), such as concentrated aqueous solutions of ammonium glycolate.

Reactive solvent extraction may also be used to obtain glycolic acid from an aqueous solution of ammonium glycolate (see present Examples 39-61 and Co-pending U.S. provisional patent application 60/638,128; herein incorporated by reference). More specifically, a method to isolate glycolic acid from an aqueous solution comprising ammonium glycolate is provided comprising:

a) providing a first phase, wherein said first phase is a water-immiscible organic solvent mixture comprising:
   i) about 30 volume percent to about 99 volume percent of said first phase is at least one tertiary alkyl amine having the formula

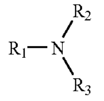

wherein $R_1$, $R_2$, and $R_3$ are independently a C8 to C12 alkyl group; and
   ii) about 1 volume percent to about 70 volume percent of said first phase is at least one diluent selected from the group consisting of methyl isobutyl ketone, 1-octanol, 1-decanol, methylene chloride, 1-chlorobutane, chlorobenzene, chloroform, kerosene, toluene, mixed xylenes, tributyl phosphate, and mixtures thereof;
b) providing a second phase, wherein said second phase is an aqueous solution comprising glycolic acid having a pH of about 3 or less; said second phase formed by the process of:
   i) providing an aqueous solution of ammonium glycolate; said aqueous solution of ammonium glycolate having a concentration about 5 weight % to about 40 weight % ammonium glycolate; and
   ii) adding an amount of mineral acid sufficient to lower the pH of the aqueous ammonium glycolate solution of (b)(i) to about 3 or less; whereby an aqueous solution comprising glycolic acid is formed;
c) contacting said first phase with said second phase in a reactive extraction process; thereby forming a glycolic acid-loaded first phase;
d) isolating said glycolic acid-loaded first phase;
e) contacting said glycolic acid-loaded first phase with a third phase in a back extraction process; whereby glycolic acid in the glycolic acid-loaded first phase is extracted into said third phase; wherein said third phase is an aqueous solution that is immiscible in said glycolic acid-loaded first phase; and
f) recovering the glycolic acid from said third phase.

In one embodiment, the tertiary trialkylamine is selected from the group consisting of tri-n-octylamine, tri-isooctylamine, tri-n-nonylamine, tri-n-decylamine, and tri-n-dodecylamine. In another embodiment, the tertiary trialkylamine is selected from the group consisting of Alamine® 308 (CAS# 2757-28-0), Alamine® 300 (CAS# 1116-76-3), Alamine® 304-1 (CAS# 102-87-4), and Alamine® 336 (CAS# 68814-95-9) (Cognis Corp., Cincinnati, Ohio.). In a further embodiment, the diluent is selected from the group consisting of methyl isobutyl ketone (MIBK), kerosene, toluene, mixed xylenes, 1-octanol, and mixtures thereof. In yet another embodiment, the water-immiscible organic solvent is selected from the group consisting of 90% (vol/vol) Alamine® 336:10% (vol/vol) MIBK; 90% Alamine® 336: 10% 1-octanol; 90% Alamine® 336:10% toluene; and 90% Alamine® 336:10% mixed xylenes.

The concentration of tertiary trialkyl amine in the first phase may range from about 30 percent (vol/vol) to about 99 percent (vol/vol), preferably about 50 percent (vol/vol) to about 90 percent (vol/vol), and most preferably about 70 percent (vol/vol) to about 90 percent (vol/vol). The amount of diluent in the first phase may range from about 1 percent (vol/vol) to about 70 percent (vol/vol), preferably about 10 percent to about 50 percent, and most preferably about 10 to about 30 percent A suitable organic extraction mixture for extracting glycolic acid is comprised of a mixture of Alamine® 336 with one or more diluents selected from the group consisting of methyl isobutyl ketone (MIBK), 1-octanol, 1-decanol, methylene chloride, 1-chlorobutane, chlorobenzene, chloroform, kerosene, toluene, mixed xylenes, and tributyl phosphate. In one embodiment, the organic phase extractant is comprised of Alamine® 336 in combination with one or more diluents selected from the group consisting of MIBK, 1-octanol, toluene, xylene, and kerosene. In another embodiment, the reactive organic solvent is comprised of about 50% to about 95% Alamine® 336, preferably about 65% to about 95% of the organic solvent mixture. The organic solvent is comprised of one or more diluents in a range of about 50% to about 5% diluent, preferably 35% to about 5% of the organic solvent mixture. In one embodiment, the mixed organic solvent is comprised of about 70% Alamine® 336, about 10% MIBK, and about 20% kerosene. In another embodiment, the mixed organic solvent is comprised of about 90% Alamine® 336 and about 10% diluent selected from the group consisting of MIBK, 1-octanol, toluene, and xylene.

One of skill in the art can determine the preferred temperature of the organic phase extraction. In one embodiment, the extraction reaction is conducted at a temperature from about 10° C. to about 90° C., more preferably about 20° C. to about 75° C., and most preferably about 25° C. to about 75° C.

The amount of mixed organic solvent required to extract the glycolic acid from the acidified aqueous phase is dependent upon the degree of solvent loading. One of skill in the art can adjust the volume of the mixed organic solvent used to extract the glycolic acid depending upon the amount of glycolic acid present in the aqueous phase. The glycolic acid can be recovered from the organic phase by back extraction.

Another method to obtain glycolic acid from ammonium glycolate is thermal decomposition in the presence of an esterifying agent. The solvent may act by protecting the glycolic acid from reactive ammonia (thereby preventing amide formation) or may act as an organic reactive extraction solvent, thereby aiding in the separation of the acid (Meng et al., US 2004/0210087; hereby incorporated by reference in its entirety). Optionally, this method can also include an alcohol, thereby creating the ester (which may be more soluble in the organic solvent). The organic solvent may be selected from the group consisting of tertiary alkylamines, alcohols, amides, ethers, ketones, phosphorus esters, phosphine oxides, phosphine sulfides, alkyl sulfides, and combinations thereof. Glycolic acid (or the corresponding ester) is then recovered from the organic solvent (liquid phase) during a back extraction step. The recovered solvent can be recycled to the salt splitting reaction step. Unfortunately, solvent extraction/back extraction may be problematic as various immiscible fluids form complex physical mixtures that are difficult to separate.

Alcoholysis (Esterification)

Cockrem (U.S. Pat. No. 6,291,708 B1) teaches rapid heating of a mixture of ammonium salt of an organic acid with alcohol to produce a liquid stream containing acid, ester, and unreacted ammonium salt. Cockrem fails to address the separation of unreacted salts from the acid and ester. However, a process of using alcoholysis (heated alcohol vapor that acts as both an esterification agent and stripping gas) to separate the glycolic acid ester (as a vapor) from the aqueous solution comprising ammonium glycolate has been described that addresses this problem (See present Examples 67-74 and copending U.S. Provisional application 60/638,126; herein incorporated by reference).

In order to overcome the problems associated with separating an ester from unreacted ammonium glycolate in a liquid matrix, alcoholysis may be used (U.S. 60/638,126). The ammonium salt of a carboxylic acid (i.e., ammonium glycolate) will react with alcohols to form an ester of the alcohol and acid while liberating ammonia with water as shown in Equation 4.

$$HOCH_2CO_2^-NH_4^+ + R_2OH \rightarrow HOCH_2CO_2R_2 + NH_3 + H_2O \quad (4)$$

U.S. 60/638,126 provides a process to obtain glycolic acid from an aqueous solution comprising ammonium glycolate comprising:

(a) providing
  (i) an aqueous solution comprising ammonium glycolate; and
  (ii) a heated alcohol vapor feed stream comprising an alcohol having the formula:

$R_2$—OH wherein $R_2$ is a C1 to C4 straight chain or branched alkyl group; and
  (iii) a reaction vessel;
(b) contacting said aqueous solution comprising ammonium glycolate with said heated alcohol vapor feed stream in said reaction vessel whereby a first vapor product stream is produced comprising a glycolic acid ester;
(c) recovering the glycolic acid ester from said first vapor product stream;
(d) hydrolyzing the glycolic acid ester of (c) into glycolic acid; and
(e) recovering the glycolic acid produced in step (d).

In one embodiment, the alcohol is selected from the group consisting of methanol, ethanol, n-propanol, isopropanol, n-butanol, isobutyl alcohol, and t-butanol. In a preferred embodiment, the alcohol is methanol (i.e., forming methyl glycolate in the vapor product stream).

The amount of heated alcohol vapor contacted with the carboxylic acid ammonium salt is typically in a molar excess relative to the amount of carboxylic acid ammonium salt in the aqueous feed stream. The molar ratio of the heated alcohol vapor to the carboxylic acid ammonium salt may vary, but it typically from about 5 to about 300 moles per mole of carboxylic acid ammonium salt (molar ration at least about 5:1 to about 300:1), preferably about 5 to about 200 moles per mole of the carboxylic acid ammonium salt, most preferably about 20 to about 100 moles per mole of carboxylic acid ammonium salt. A molar excess of the alcohol vapor tends to inhibit amide formation.

The alcohol vapor feed stream (e.g., methanol) temperature is typically chosen to ensure that the alcohol generally remains in its vapor phase so that it acts as both an esterifying agent and a stripping/carrying gas. The temperature of the heated alcohol vapor feed stream entering the reaction chamber may vary according to the selected alcohol as well as the specific equipment geometry. The heated alcohol vapor fed acts as a source of heat for the reaction, an esterifying agent, and as a stripping/carrying gas for the carboxylic acid ester formed by the present process.

The present examples illustrate the use a heated methanol vapor to form methyl glycolate (which is subsequently hydrolyzed to glycolic acid). Typically, the temperature of the heated methanol vapor is about 140° to about 350° C. In one embodiment, the temperature of the methanol vapor feed stream is about 170° C. to about 300° C. In another embodiment, the temperature of the methanol vapor feed stream is about 230° C. to about 250° C.

The reactor pressure and temperature can be adjusted to optimize production of the desired product. Selecting the appropriate operating temperature and pressure for the reaction must consider the vapor pressure of both the alcohol and the corresponding carboxylic acid ester. At the selected operating pressure, the reaction temperature is selected so that the vapor pressure of the carboxylic acid ester is typically at least about one quarter (¼) of the operating pressure of the system. At this temperature the vapor pressure of the alcohol should exert at least about 4 times (4×) the operating pressure. A typical operating pressure is from about 0 psig (~0 kilopascals (kPa)) to about 80 psig (~550 kPa), preferably about 0 psig (0 kPa) to about 50 psig (345 kPa), and most preferably about 10 psig (69 kPa) to about 50 psig (345 kPa).

A typical operating temperature for the alcoholysis reactor is about 140° C. to about 300° C., preferably about 170° C. to about 200° C. In one aspect, the carboxylic acid ammonium salt is ammonium glycolate and the alcohol is methanol. The reactor temperature used this particular combination is typically about 100° C. to about 300° C., preferably about 150° C. to about 250° C., more preferably about 170° C. to about 225° C., and most preferably about 170° C. to about 200° C.

The reactor may optionally include a packing material or a high boiling point fluid/liquid to improve the yield of the desired carboxylic acid ester. The benefit of the packing or high boiling point fluid is to improve the contacting between the aqueous salt solution and the alcohol vapor. The packing may be random packing, engineered packing, or various distillation plate designs. See Perry's 7$^{th}$ edition Chapter 14.23 through 14.61 (*Perry's Chemical Engineers' Handbook, 7$^{th}$* ed., Perry, Robert H., Green, Dow W., and Maloney, James O., editors; McGraw Hill Companies, Inc., New York, N.Y., 1997). Commercial designs for gas liquid reaction systems are illustrated in Perry's FIGS. 23-25, 23-26, and 13-79. The high boiling point fluid should be selected to have a low vapor pressure at the chosen operating conditions or be easily separated from the recovered ester. The fluid may be inert to the esterification chemistry (such as mineral oil) or potentially participate in the esterification chemistry such as a polyol. The polyol is a material with a molecular weight greater than 150 and at least one hydroxyl group, including alcohols such as decanol and dodecanol. Typical polyols include polyethylene ether glycol (PEG), polypropylene ether glycol (PPG) and polytetramethylene ether glycol (PTMEG), as well as copolymers of these polyalkylene ether glycols.

Recovering the ester as a liquid from the first vapor product may be accomplished by reducing the temperature of the vapor to form a condensate. The cooling may be accomplished in a direct or indirect contact condenser (see Perry's Chapter 11; supra). The condenser ("hot condenser") temperature is typically maintained at or below the boiling point of the respective carboxylic acid ester but above the normal boiling point of the heated alcohol vapor. Typically, the partial condenser temperature is maintained at least about 10° C. to about 100° C. below the normal boiling point of the ester. Control of the alcohol vapor temperature, the reactor pressure, and the partial condenser temperatures should be used to selectively condense the desired carboxylic acid ester from the corresponding esterifying agent (i.e. the alcohol), water, and ammonia vapors.

Distillation may also be used to obtain the carboxylic acid ester from the vapor product stream. Distillation designs (e.g., generally comprised of a reflux column, an overhead condenser, and reflux control) are well know. Commercial designs for distillation systems may be found in Perry's Chapter 13. Designs with multiple product removal may be particularly well suited for recovering the ester (See Perry's FIGS. 13-6.).

In one embodiment, the gas liquid contacting operation and the ester recovery from the first vapor product operation may be accomplished in a single device.

The corresponding carboxylic acid can be subsequently obtained by hydrolyzing the carboxylic acid ester collected in the first liquid product stream (i.e., from the partial condenser). Techniques to hydrolyze esters to acids are known to those skilled in the art. The recovered ester can be combined with water and placed into a short path batch distillation apparatus containing a short fractionating column and a total condenser. Heating the mixture will drive methanol overhead as well as some of the water, leaving the carboxylic acid behind in the heated mixture.

Electrodialysis

Electrodialysis with bipolar membrane (EDBM) has been proposed to recovering organic acids from their corresponding ammonium salt. For EDBM to work, the solutions must be conductive. For the ammonium salt of weak acids, the products of EDBM (organic acid and ammonium hydroxide) are very weak conductors resulting in high resistance of the solutions and low production rates. To offset this, a conductive salt (i.e., ammonium chloride) is added to the base loop (ammonium hydroxide stream). As the base concentration increases, ammonia can be stripped from the solution and the ammonium salt recycled to maintain conductivity.

The composition of the ammonium salt of the organic acid must be carefully monitored for multivalent cations such as calcium. These cations may precipitate by associating with hydroxyl groups and destroy the membranes. Concentrations of the multivalent cations are preferably below about 5 ppm, most preferably below about 1 ppm.

For example, a typical lab scale EDBM system can be set up with membranes suitable for ammonium salts. First, a recirculating base loop containing about 5 wt % ammonium chloride is established. An approximately 3 M ammonium glycolate recirculation loop is also established. A typical batch test run is conducted at constant current of about 0.5 to about 1.0 kA/$m^2$. The circulation loops are maintained for about 1 hour to about 5 hours. As the EDBM proceeds, conductivity and pH in the ammonium glycolate loop decreases. Typically, an EDBM run under such conditions would be expected to convert at least about 80% of the ammonium glycolate into glycolic acid. The resulting glycolic acid/ammonium glycolate solution can be subsequently treated with a strong cationic ion exchange resin or other methods to complete the conversion.

Polymerization

The ammonium salt of a carboxylic acid comprised of a hydroxyl group can undergo condensation polymerization to form dimers, oligomers, and polymers while liberating ammonia. The resulting polymers can be separated from the reaction mixture using any number of techniques. Once separated from the reaction mixture, depolymerization can be used to obtain the free acid.

Thermal Salt Cracking of Substantially Anhydrous Ammonium Glycolate Salt

Thermal decomposition ("salt cracking") may be used to obtain a product comprising glycolic acid (see present Examples 62-66 and co-pending U.S. Provisional Patent Application U.S. 60/638,148; herein incorporated by reference in its entirety). This process does not require the addition of one or more chemicals prior to thermally decomposing the substantially anhydrous ammonium glycolate salt.

U.S. 60/638,148 describes a process to obtain glycolic acid from an aqueous solution comprising ammonium glycolate comprising:

a) providing a feed stream comprising an aqueous solution of ammonium glycolate;
b) removing free water from the feed stream to produce a substantially anhydrous salt of ammonium glycolate; and
c) heating the product of step b) to a temperature of less than about 140° C. under a vacuum sufficient to remove ammonia whereby a first liquid product mixture comprised of glycolic acid is produced.

In one embodiment, the method may also include the steps of:

d) adding water to the first liquid product mixture of step (c) to form a first rehydrated liquid product mixture; said rehydrated liquid product mixture comprising glycolic acid, glycolic acid oligomers, glycolamide, glycolic acid oligomer ammonium salts, and unreacted ammonium glycolate; and
e) heating the rehydrated liquid product mixture of step (d) under conditions whereby a portion of the glycolic acid oligomers are hydrolyzed into free glycolic acid, wherein a second liquid product mixture comprising glycolic acid is formed.

Thermal salt cracking typically produces a product mixture comprising glycolic acid. Thermal salt cracking may be combined with one or more of the methods described herein in order to isolate the glycolic acid produced. In one embodiment, thermal salt cracking is used to prepare a partially deammoniated product that is subsequently used as a starting material for one or more of the additional recovery methods described herein.

The first step in the process is the removal of free water from a feed stream comprising an aqueous solution of ammonium glycolate, so that a substantially anhydrous ammonium glycolate salt is formed (the substantially anhydrous salt is a viscous liquid at room temperature (~25° C.)). Methods of removing the free water from the aqueous reaction mixture are well-known in the art including, but not limited to distillation, vacuum distillation, lyophilization, and evaporation. In one embodiment, the free water is removed using vacuum distillation. Typically the aqueous solution of ammonium glycolate is heated to a temperature of about 40° C. to about 90° C., preferably about 40° C. to about 80° C. under a vacuum. The vacuum pressure may vary, but is typically about 0.5 mm Hg to about 700 mm Hg absolute pressure, preferably about 0.5 mm Hg to about 635 mm Hg absolute pressure, more preferably about 0.5 mm Hg to about 50 mm Hg absolute pressure. The length of time required to remove the free water may vary and can be determined by measuring the amount of free water removed. Typically, the amount of time required to form the substantially anhydrous salt is about 5 minutes to about 24 hours, preferably about 5 minutes to about 8 hours, more preferably about 1 hour to about 6 hours.

In one embodiment, the feed stream is heated to about 40° C. to about 80° C. using a vacuum of about 5 to about 25 mm Hg absolute pressure. In another embodiment, the vacuum applied is about 10 mm Hg absolute pressure and the temperature is about 40° C. to about 80° C. In yet another embodiment, the feed stream is heated to about 40° C. to about 70° C.; preferably about 40° C. to about 60° C., in vacuum of about 0.5 to 5 mm Hg absolute pressure; preferably at least about 1 mm Hg to about 5 mm Hg absolute pressure until a substantially anhydrous salt is formed. Optionally, a non-reactive gas (e.g., nitrogen) is used to aid in the removal of water when making the anhydrous ammonium glycolate salt. The amount of water removed can be measured using a variety of techniques well known in the art including, but not limited to weight loss (i.e., a 25 wt % ammonium glycolate solution should lose up to about 75% of its weight), changes in boiling temperature, and direct analysis of the of the vapor being removed. Some water may continue to evolve from the reaction mixture as side reactions (e.g., condensation polymerization) may generate some additional water.

The next step in the process involves heating the substantially anhydrous salt under a vacuum to a temperature sufficient to thermally decompose the ammonium salt into glycolic acid and ammonia as shown in Equation 5.

$$HOCH_2CO_2^-NH_4^+ \rightarrow NH_3 + HOCH_2CO_2H$$

The temperature used should be chosen so that thermal decomposition of the salt occurs while minimizing decomposition of the acid and/or minimizing unwanted side reactions that may generate undesirable byproducts such as glycolamide. Suitable vacuum pressures can be determined by one of skill in the art. An example of a typical vacuum range is about 0.5 to about 385 mm Hg absolute pressure. In one embodiment, the vacuum range is about 0.5 to about 80 mm Hg absolute pressure and the temperature is less than about 140° C. In another embodiment, the anhydrous salt is heated to a temperature of about 100° C. to about 140° C. under a vacuum of about 0.5 to about 1.5 mm Hg absolute pressure. In yet another embodiment, the substantially anhydrous salt is heated to a temperature of about 120° C. to about 140° C. under a vacuum of about 0.5 to about 5 mm Hg absolute pressure. In yet a further embodiment, the anhydrous salt is thermally decomposed at a temperature of about 120° C. to about 140° C. under a vacuum of about 0.5 to about 1.5 mm Hg absolute pressure. The absolute pressure during the thermal decomposition of the molten ammonium salt is in part dependent on the rate of generation of ammonia gas, and may be greater than the absolute pressure of the vacuum applied during the thermal decomposition. The thermal decomposition of the molten ammonium salt can use any evaporator design, however a wipe film evaporator is preferred.

The present process includes the step of heating the substantially anhydrous salt of ammonium glycolate. As used herein, the term "heating the substantially anhydrous salt of ammonium glycolate" or "salt heating period" refers to heat treatment step that includes both a time and temperature component. The heating period used to thermally decompose the molten ammonium glycolate salt into a fir product mixture (first "deammoniated" product mixture) comprising glycolic acid and may be adjusted depending upon the temperature and pressure used. The products of the reaction can be monitored (i.e., ammonia generated during thermal decomposition) to determine the amount of time necessary to obtain the desired product. In one embodiment, the amount of ammonia released is monitored to determine the length of time sufficient to produce the desired deammoniated product. In another embodiment, the heating period used to produce the deammoniated product is about 10 minutes to about 24 hours, preferably about 30 minutes to about 8 hours, more preferably about 1 hour to about 8 hours, and most preferably about 1 hour to about 6 hours.

The liquid product mixture (first liquid product mixture) produced by thermal decomposition of the anhydrous salt of ammonium glycolate is generally comprised of glycolic acid, oligomers of glycolic acid (both linear and cyclic species such as glycolide), glycolamide, ammonium salts of oligomers of glycolic acid, and unreacted ammonium glycolate. In one aspect, the first liquid product mixture may be further processed to chemically hydrolyze the oligomers of glycolic acid into free glycolic acid (see Example 63). This can be accomplished by first adding water to the liquid product mixture to produce a rehydrated liquid product mixture. The rehydrated liquid product mixture is subsequently heated for a period of time sufficient to hydrolyze at least a portion of the glycolic acid oligomers into free glycolic acid (monomeric) thereby forming a second liquid product mixture. The amount of water added to the first liquid product mixture may vary, but is typically about 5 wt % to about 95 wt %, preferably about 20 wt % to about 80 wt %, more preferably about 40 wt % to about 60 wt %, and more preferably about 50 wt % based on the total weight of the resulting rehydrated liquid product mixture. As used herein, the term "heating the rehydrated liquid product mixture" is used to describe a process wherein the rehydrated liquid product mixture is heated to a temperature sufficient to hydrolyze at least a portion of the glycolic acid oligomers into free glycolic acid. In one embodiment, the heating (refluxing) conditions includes a temperature of about 90° C. to about 110° C., preferably about 100° C. to about 105° C. for a period of time from about 10 minutes to about 6 hours, preferably about 30 minutes to about 6 hours, more preferably about 1 hour to about 4 hours, and most preferably about 1.5 to about 3 hours.

Thermally decomposing the salt under the specified conditions converts a significant portion of the molten ammonium glycolate salt into glycolic acid and some additional byproducts such as glycolide (cyclic dimer of glycolic acid), linear polymeric forms of glycolic acid (typically dimers up to pentamers), the ammonium salts of linear polymeric forms of glycolic acid (typically dimers up to pentamers), and glycolamide. One of skill in the art can adjust the conditions used to thermally decompose the ammonium glycolate to optimize free glycolic acid production while minimizing undesirable side reactions, such as the production of glycolamide. The ammonia produced during thermal decomposition can be recovered and recycled. Optionally, the aqueous ammonium glycolate solution is partially deammoniated to produce a deammoniated product that contains significantly less ammonium ion. This deammoniated product is particularly attractive for subsequent processing as less waste (mineral salts) is generated In addition to recovery of glycolic acid from a solution comprising ammonium glycolate, the solution comprising ammonium glycolate may be recovered directly by separation from the nitrilase catalyst by known techniques including but not limited to decantation or filtration, and subsequently optionally concentrated by distillation of water from the filtrate.

Glycolamide Byproduct Deamidation

The formation of glycolamide is an unwanted byproduct sometimes generated (depending upon the recovery method employed) when producing glycolic acid from ammonium glycolate. Glycolamide is formed by the reaction of ammonia with glycolic acid. Equation 6.

$$HOCH_2CO_2H+NH3 \rightarrow HOCH_2CONH_2+H_2O \quad (6)$$

However, glycolic acid can be produced from the glycolamide by reversing this reaction (chemical hydrolysis). The can be accomplished by hydrolyzing glycolamide with water under refluxing conditions (Equation 7). Optionally, the aqueous refluxing may also contain an acid or base, or an acidic or basic catalyst.

$$HOCH_2CONH_2+H_20 \rightarrow HOCH_2CO_2H+NH_3 \quad (7)$$

Alternatively, glycolamide can also react with an alcohol or polyol to liberate the corresponding ester and ammonia as shown in Equation 8.

$$HOCH_2CONH_2+R_2OH \rightarrow HOCH_2CO_2R_2+NH_3 \quad (8)$$

Alternatively, any glycolamide produced can be treated with an amidase (under appropriate conditions) to convert glycolamide to glycolic acid. Methods of converting amides to the corresponding acids using an amidase (under appropriate conditions) are known in the art. Genes encoding enzymes having amidase activity have also been cloned, sequenced, and expressed in recombinant organisms. For example, Azza et al., (*FEMS Microbiol. Lett.,*122:129 (1994)) disclose the cloning and over-expression in *E. coli* of an amidase gene from *Brevibacterium* sp. R312 under the control of the native promoter. Similarly, Kobayashi et al., (*Eur. J. Biochem.,* 217: 327 (1993)) teach the cloning of both a nitrile hydratase and amidase gene from *R. rhodococcus* J1 and their co-expression in *E. coli.* Wu et al. (*DNA Cell Biol.,* 17:915-920 (1998); U.S. Pat. No. 6,251,650) report the cloning and overexpressing of a gene for amidase from *Pseudomonas putida* 5B in *E. coli.*

In one embodiment, the amidase activity of *Comamonas testosteroni* 5-MGAM-4D is used to convert glycolamide to glycolic acid (ATCC 55744; U.S. Pat. Nos. 5,858,736, 5,922, 589, and U.S. Ser. No. 10/977,893; all hereby incorporated by reference in its entirety). *Comamonas testosteroni* 5-MGAM-4D has been shown to contain thermally-stable, regiospecific nitrile hydratase (EC 4.2.1.84) and amidase (EC 3.5.1.4) activities useful in the conversion of a variety of nitriles to their corresponding amides and carboxylic acids (Equation 2).

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

General Methods

The following examples are provided to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and methods suitable for the maintenance and growth of bacterial cultures are well known in the art. Techniques suitable for use in the following examples may be found as set out in *Manual of Methods for General Bacteriology* (1994) (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C.) or by Thomas D. Brock, in *Biotechnology: A Textbook of Industrial Microbiology,* (1989) Second Edition, (Sinauer Associates, Inc., Sunderland, Mass.).

Procedures required for genomic DNA preparation, PCR amplification, DNA modifications by endo- and exo-nucleases for generating desired ends for cloning of DNA, ligations, and bacterial transformation are well known in the art. Standard recombinant DNA and molecular cloning techniques used here are well known in the art and are described by Maniatis, supra; and by T. J. Silhavy, M. L. Bennan, and L. W. Enquist, *Experiments with Gene Fusions,* (1984) Cold Spring Harbor Laboratory Press, Cold Spring, N.Y.; and by Ausubel, F. M. et al., *Current Protocols in Molecular Biology,* (1994-1998) John Wiley & Sons, Inc., New York.

All reagents and materials were obtained from Aldrich Chemicals (Milwaukee, Wis.), DIFCO Laboratories (Detroit, Mich.), GIBCO/BRL (Gaithersburg, Md.), or Sigma/Aldrich Chemical Company (St. Louis, Mo.) unless otherwise specified.

The abbreviations in the specification correspond to units of measure, techniques, properties, or compounds as follows: "sec" means second(s), "min" means minute(s), "h" or "hr" means hour(s), "d" means density in g/mL, "μL" means microliters, "mL" means milliliters, "L" means liters, "mM" means millimolar, "M" means molar, "mmol" means millimole(s), "wt" means weight, "wt %" means weight percent, "g" means grams, "μg" means micrograms, HPLC" means high performance liquid chromatography, "O.D." means optical density at the designated wavelength, "dcw" means dry cell weight, "U" means units of nitrilase activity, "EDTA" means ethylenediaminetetraacetic acid, and "DTT" means dithiothreitol.

Analytical Methodology

HPLC Analysis

The reaction product mixtures were analyzed by the following HPLC method. Aliquots (0.01 mL) of the reaction mixture were added to 1.50 mL of water, and analyzed by HPLC (HPX 87H column, 30 cm×7.8 mm; 0.01 N $H_2SO_4$ mobile phase; 1.0 mL/min flow at 50° C.; 10 μL injection volume; RI detector, 20 min analysis time). The method was calibrated for glycolonitrile at a series of concentrations using commercially available glycolonitrile purchased from Aldrich.

Quantitative $^{13}C$ NMR Analysis

Quantitative $^{13}C$ NMR spectra were obtained using a Varian Unity Inova spectrometer (Varian, Inc., Palo Alto, Calif.) operating at 400 MHz. Samples were prepared by taking 3.0 mL of the reaction product along with 0.5 mL of $D_2O$ in a 10 mm NMR tube. $^{13}C$ NMR spectra were typically acquired using a spectral width of 26 KHz with the transmitter located at 100 ppm, 128K points, and a 90-degree pulse (pw90=10.7 microseconds at a transmitter power of 56 db). The longest 13C T1 (23 sec) was associated with the GLN nitrile carbon, and the total recycle time was set greater than ten times this value (recycle delay d1=240 sec, acquisition time at=2.52 sec). Signal averaging of 360 scans gave a total experiment time of 26.3 hours. The Nuclear Overhauser Enhancement (NOE) was suppressed by gating on the Waltz-modulated 1 H decoupling only during the acquisition time (at).

COMPARATIVE EXAMPLE A

Pre-Heating 0% of Formaldehyde Continuous Feed

Approximately 10.18 g of 52 wt % aqueous solution of formaldehyde (<1% methanol, E.I. DuPont de Nemours; Wilmington, Del.) was mixed with 12.81 g of water, and the slurry was heated to about 76° C. for about 40 min until the mixture became a clear homogeneous liquid solution. The solution was allowed to cool to ambient temperature and remained a homogeneous liquid. 0.14 mL of 16.7 wt % aqueous NaOH solution was then added to the formaldehyde solution. 1.56 g of the resulting solution (23 wt % formaldehyde) was placed in the reaction vessel, and the remainder was used for the continuous formaldehyde feed.

The reaction vessel, equipped with stirring, was placed within an oil bath maintained at 55° C. The reactants were then each continuously pumped into the reaction vessel over a period of about 2.0 hr, as follows:

4.41 mL/hr of 50 wt % aqueous HCN solution (d=0.86 g/mL)

7.00 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.07 mL of 37 wt % aqueous HCl.

FIG. 1 shows the $^{13}C$ NMR spectrum of the resulting glycolonitrile solution, qualitatively indicating the purity of the glycolonitrile product. The $^{13}C$ NMR spectrum shows the major glycolonitrile $^{13}C$ resonances at about δ 48 and 119 ppm. There are also substantial resonances around δ 80-90 ppm for unreacted formaldehyde and around δ 60 ppm for other by-product species derived from unreacted formaldehyde.

EXAMPLE 1

Pre-Heating 90% of Formaldehyde Continuous Feed

Approximately 10.18 g of 52 wt % aqueous solution of formaldehyde (<1% methanol, DuPont) was mixed with 12.81 g of water, and the slurry was heated to about 76° C. for about 40 min until the mixture became a clear homogeneous liquid solution. The solution was allowed to cool to ambient temperature and remained a homogeneous liquid. 0.16 mL of 16.7 wt % aqueous NaOH solution was then added to the formaldehyde solution. 1.56 g of the resulting solution (23 wt % formaldehyde) was placed in the reaction vessel, and the remainder was used for the continuous formaldehyde feed.

The reaction vessel, equipped with stirring, was placed within an oil bath maintained at 55° C. The approximately 12-inch section of the formaldehyde feed line (1/16" OD (about 1.6 mm)×0.040" ID (about 1.02 mm)) directly preceding the inlet to the reaction flask was heated to 120° C., and the reactants were then each continuously pumped into the reaction vessel over a period of about 2.0 hr, as follows:

4.41 mL/hr of 50 wt % aqueous HCN solution (d=0.86 g/mL)

7.00 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.08 mL of 37 wt % aqueous HCl.

Figure 2:
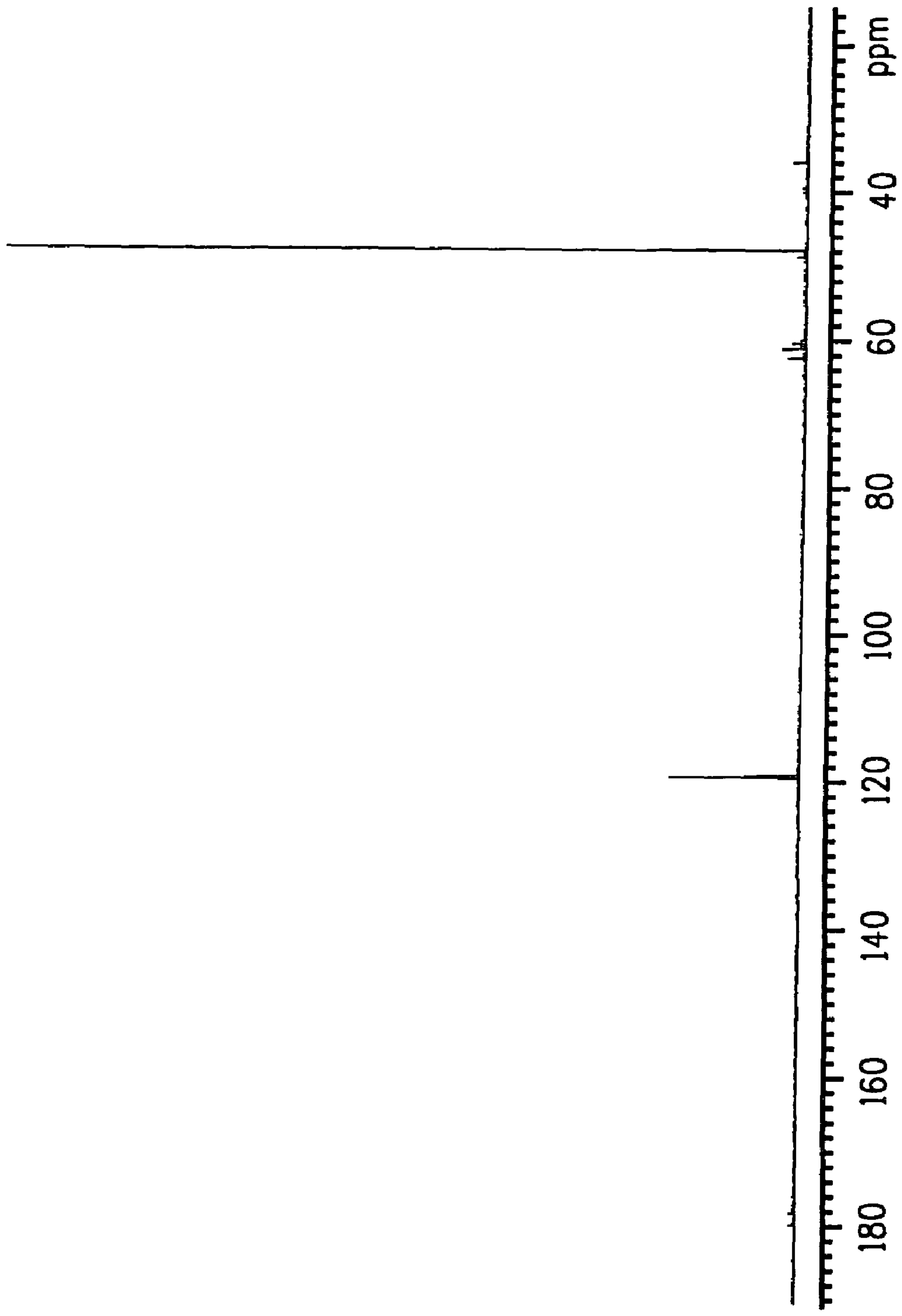

FIG. 2 shows the $^{13}C$ NMR spectrum of the resulting glycolonitrile solution, qualitatively indicating the purity of the glycolonitrile product. Once again, the major resonances for glycolonitrile at about δ 48 and 119 ppm are observed. But the resonances around δ 80-90 ppm evident in FIG. 1 for unreacted formaldehyde are noticeably reduced in FIG. 2. However, the resonances around δ 60 ppm for by-products derived from unreacted formaldehyde remain, most likely due to the initial formaldehyde reactor charge.

EXAMPLE 2

Pre-Heating 100% of Formaldehyde Continuous Feed

Approximately 10.18 g of 52 wt % aqueous solution of formaldehyde (<1% methanol, E.I. DuPont de Nemours) was mixed with 12.81 g of water, and the slurry was heated to about 76° C. for about 40 min until the mixture became a clear homogeneous liquid solution. The solution was allowed to cool to ambient temperature and remained a homogeneous liquid. 0.14 mL of 16.7 wt % aqueous NaOH solution was then added to the formaldehyde solution. The resulting solution (23 wt % formaldehyde) was used for the continuous formaldehyde feed.

The reaction vessel, equipped with stirring, was charged with a mixture of 0.18 g of HCN in 3.4 g of water and then placed within an oil bath maintained at 55° C. The approximately 12-inch section of the formaldehyde feed line (1/16" OD×0.040" ID) directly preceding the inlet to the reaction flask was heated to 120° C., and the reactants were then each continuously pumped into the reaction vessel over a period of about 2.0 hr, as follows:

4.41 mL/hr of 50 wt % aqueous HCN solution (d=0.86 g/mL)

7.67 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.07 mL of 37 wt % aqueous HCl.

Figure 3:
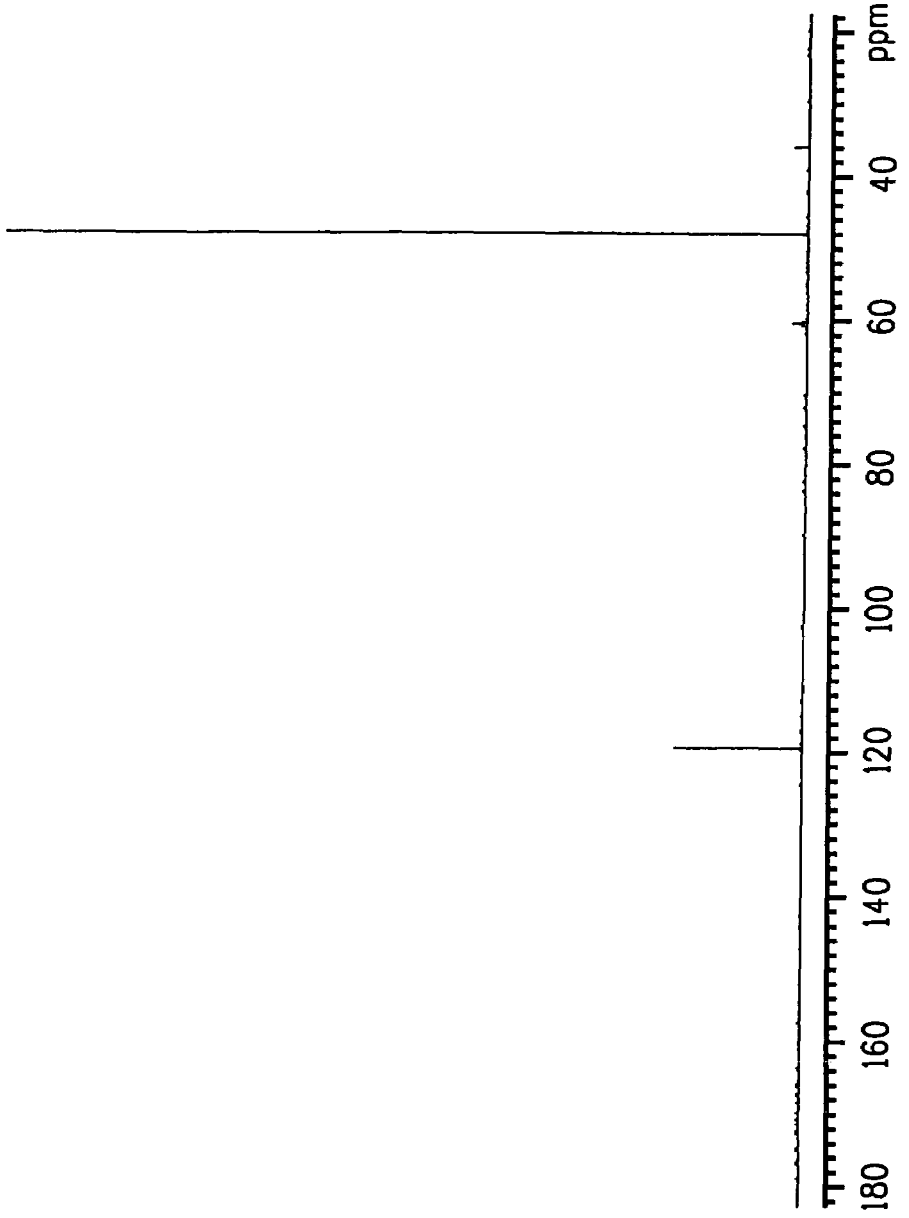

FIG. 3 shows the $^{13}C$ NMR spectrum of the resulting glycolonitrile solution, qualitatively indicating the purity of the glycolonitrile product. The major resonances for glycolonitrile at about δ 48 and 119 ppm are evident in FIG. 3, while the levels of impurities are substantially reduced from the levels observed in FIG. 1 and FIG. 2.

EXAMPLE 3

Pre-Heating 100% of Formaldehyde Continuous Feed

Approximately 14.20 g of 37 wt % aqueous solution of formaldehyde (10-15% methanol, Acros Organics, Morris Plains, N.J.) was mixed with 8.78 g of water and 0.14 mL of 16.7 wt % aqueous NaOH. The resulting solution (23 wt % formaldehyde) was used for the continuous formaldehyde feed.

The reaction vessel, equipped with stirring, was charged with a mixture of 0.18 g of HCN in 3.4 g of water and then placed within an oil bath maintained at 55° C. The approximately 12-inch section of the formaldehyde feed line (1/16" OD×0.040" ID) directly preceding the inlet to the reaction flask was heated to 120° C., and the reactants were then each continuously pumped into the reaction vessel over a period of about 2.0 hr, as follows:

4.21 mL/hr of 50 wt % aqueous HCN solution (d=0.86 g/mL)

7.67 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.07 mL of 37 wt % aqueous HCl.

Figure 4:
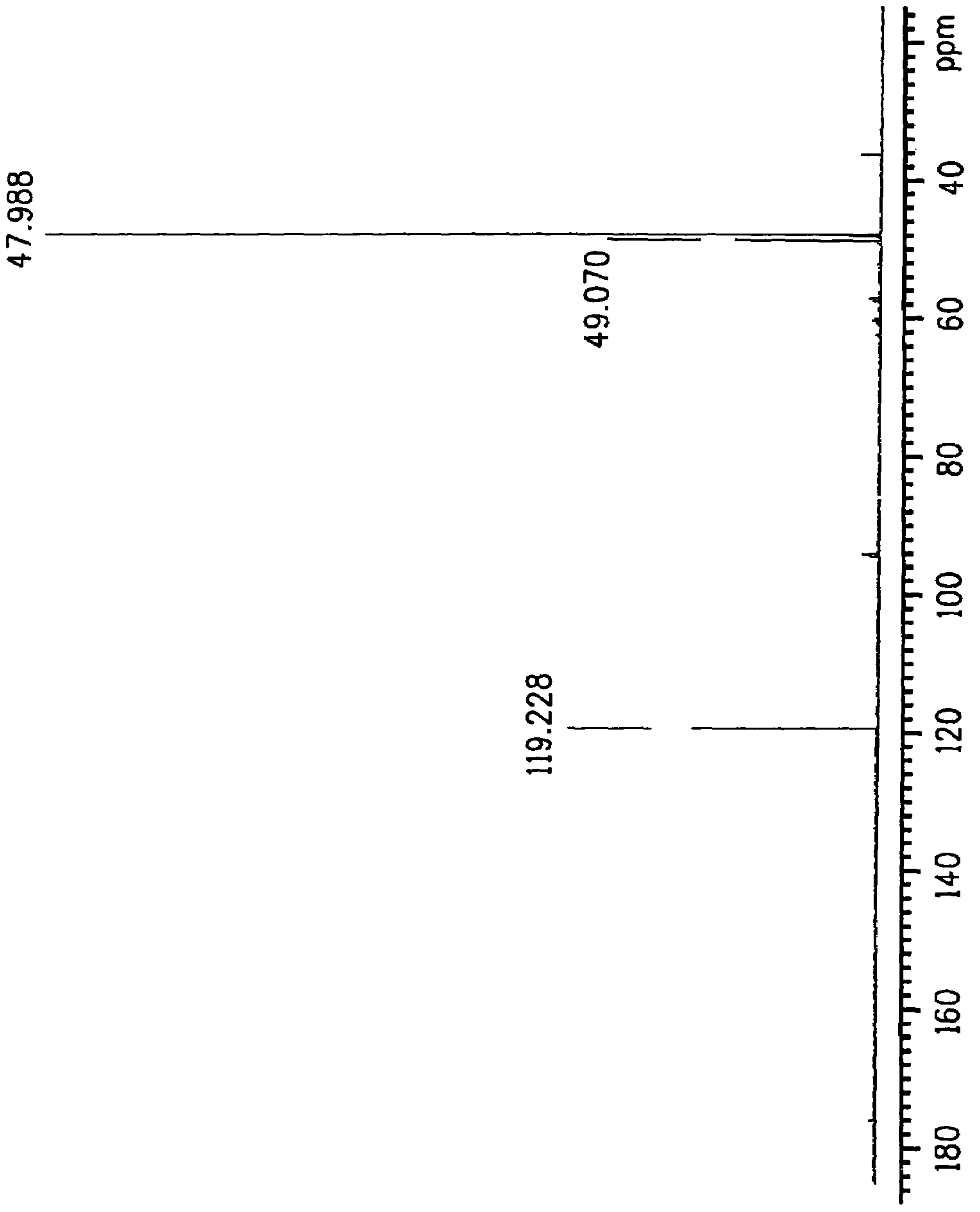

FIG. 4 shows the $^{13}C$ NMR spectrum of the resulting glycolonitrile solution, qualitatively indicating the purity of the glycolonitrile product. Again, the major resonances for glycolonitrile at about δ 48 and 119 ppm are evident in FIG. 4, while the levels of impurities are substantially reduced from the levels observed in FIG. 1 and FIG. 2. FIG. 4 also clearly shows the resonance at δ 49 ppm for the methanol from the formalin feed used in Example 3.

EXAMPLES 4-8

Pre-Heating 100% of Formaldehyde Continuous Feed

In Examples 4-8, the following glycolonitrile synthesis procedure was repeated five separate times.

Approximately 0.56 mL of 16.7 wt % aqueous NaOH solution was added to 218.0 g of 37 wt % aqueous solution of formaldehyde (containing 7 wt % to 8 wt % methanol). The resulting solution was used for the continuous formaldehyde feed.

The reaction vessel, equipped with a magnetic stirbar, was initially charged with a mixture of 3.3 g HCN in 35.3 g water and placed within a water bath maintained at around 20° C., on top of a stirplate and lab jack assembly in a lowered position. The approximately 36-inch section of the formaldehyde feed line (1/8" OD (about 3.18 mm)×0.085" ID (about 2.16 mm)) directly preceding the inlet to the reaction flask was heated to 120° C. after filling the formaldehyde feed line, and the flow of heated formaldehyde feed was first established by observing two-phase flow from the outlet of the formaldehyde feed line. After establishing two-phase flow out of the formaldehyde feed line, the reaction vessel was raised to introduce the formaldehyde feed directly into the liquid reaction mixture. The stirplate, water bath, and lab jack assembly was then raised accordingly to provide reactor mixing and to maintain the reaction temperature around 20-25° C., which was accomplished by periodically adding ice and/or dry ice to the external water bath.

The reactants were each continuously pumped into the reaction vessel over a period of about 2.0 hr, as follows:

82.4 mL/hr of 50 wt % aqueous HCN solution (d=0.86 g/mL)

92.7 mL/hr of 37 wt % aqueous formaldehyde, described above (d=1.09 g/mL).

After 2.0 hr, the feeds were stopped, and the reaction vessel, water bath, stirplate, and lab jack assembly was lowered to remove the formaldehyde feed line from the reaction product. The reaction mixture was removed from the reaction vessel and then quenched by adding of 1.3 mL of an aqueous solution of 70% glycolic acid (70% Glypure®; E.I. DuPont de Nemours, Wilmington, Del.), resulting in a glycolonitrile product solution at about pH 3.

Each of the glycolonitrile reaction product solutions was individually concentrated to remove the excess unreacted HCN and the methanol from the commercial source of formaldehyde. The concentration step was performed under vacuum with mild heating using an external oil bath at 60-70° C.

The weight of each concentrated glycolonitrile product solution was recorded, and the glycolonitrile concentration was determined by HPLC.

The conditions used in Examples 4-8, and the resulting GLN yield is reported in Table 1.

TABLE 1

Glycolonitrile Yield.

| Example # | Weight of GLN Solution (g) | Glycolonitrile Concentration (M) | Yield (% recovered GLN) |
|---|---|---|---|
| 4 | 116 | 13.9 | 61% |
| 5 | 139 | 17.7 | 94% |
| 6 | 163 | 13.7 | 85% |
| 7 | 150 | 16.7 | 95% |
| 8 | 182 | 11.6 | 80% |

Figure 5:
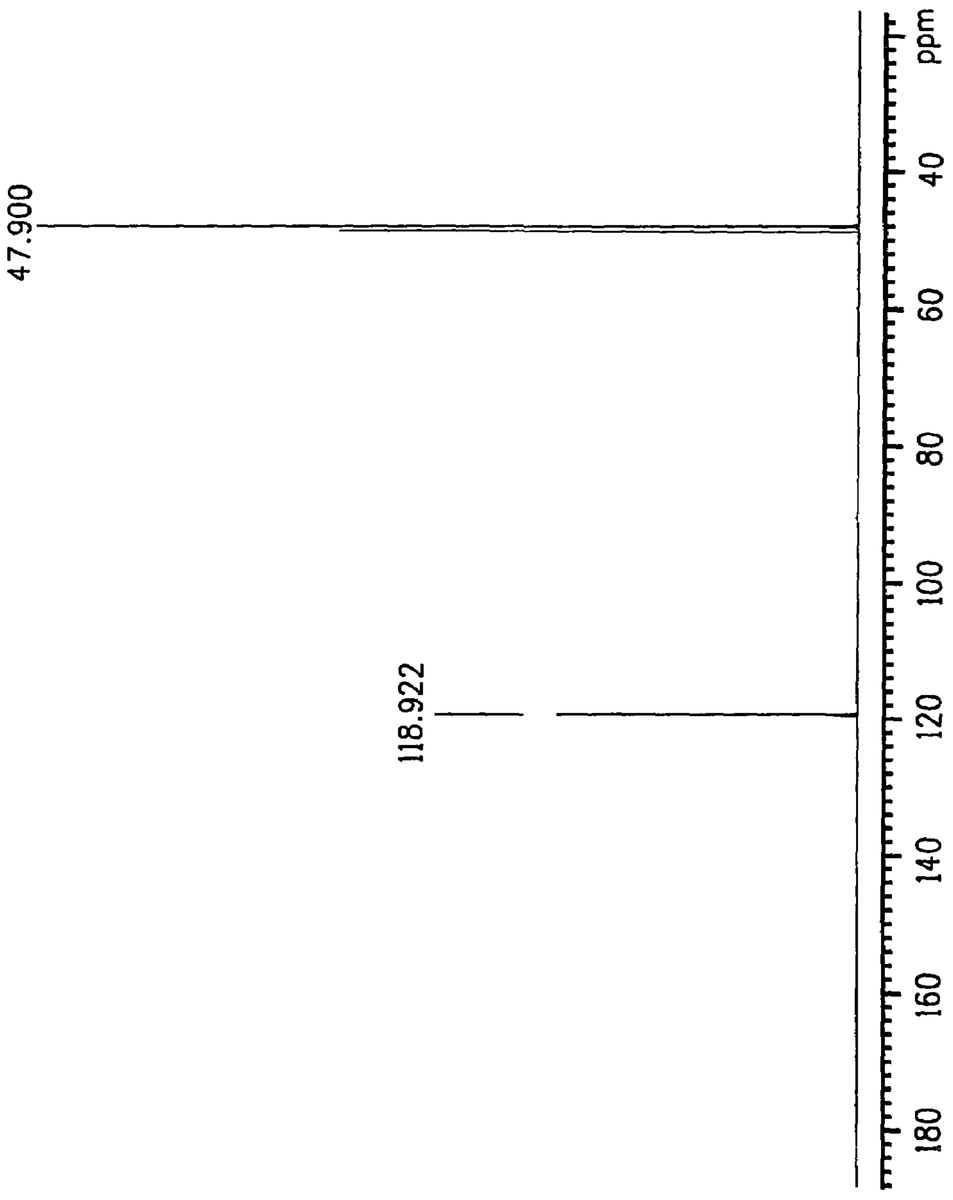
FIG. 5 shows the $^{13}C$ NMR spectrum of the composite sample produced by mixing the 5 concentrated glycolonitrile samples prepared in Examples 4-8, quantitatively indicating the purity of the glycolonitrile product. The quantitative $^{13}C$ NMR analysis was performed on the composite sample to determine the purity of the glycolonitrile produced.

The five concentrated glycolonitrile product solutions produced in Examples 4-8 were combined into a composite product sample, and a quantitative $^{13}C$ NMR analysis was performed on the composite sample to determine the purity of the glycolonitrile produced. FIG. 5 shows the $^{13}C$ NMR spectrum of the composite sample. The quantitative $^{13}C$ NMR analysis showed that the glycolonitrile product purity was greater than 99.9% in the composite sample.

EXAMPLE 9

Pre-Heating 100% of Formaldehyde Continuous Feed

Approximately 0.27 mL of 16.7 wt % aqueous NaOH solution was added to 54.5 g of 37 wt % aqueous solution of formaldehyde (containing 7-8% methanol). The resulting solution was used for the continuous formaldehyde feed.

The reaction vessel, equipped with a magnetic stirbar, was initially charged with a mixture of 0.29 g HCN in 10.3 g water and placed within a water bath maintained at around 25° C., on top of a stirplate. The approximately 12-inch section of the formaldehyde feed line (1/8" OD×0.085" ID) directly preceding the inlet to the reaction flask was heated to 150° C. after filling the formaldehyde feed line, and the flow of heated formaldehyde feed was first established outside the reaction vessel by observing two-phase flow from the outlet of the formaldehyde feed line. After establishing heated formaldehyde feed, the end of the formaldehyde feed line was placed directly into the liquid reaction mixture. The reaction temperature was maintained around 20-25° C., which was accomplished by periodically adding ice and/or dry ice to the external water bath. The reactants were each continuously pumped into the reaction vessel over a period of about 2.0 hr, as follows:

7.02 mL/hr of 50 wt % aqueous HCN solution (d=0.86 g/mL)

7.67 mL/hr of 37 wt % aqueous formaldehyde, described above (d=1.09 g/mL).

After 2.0 hr, the feeds were stopped, and the formaldehyde feed line was removed from the reaction product. The reaction mixture was removed from the reaction vessel and then quenched by adding of 0.060 mL of 70% Glypuree® glycolic acid, resulting in a glycolonitrile product solution at about pH 3.

Figure 6:
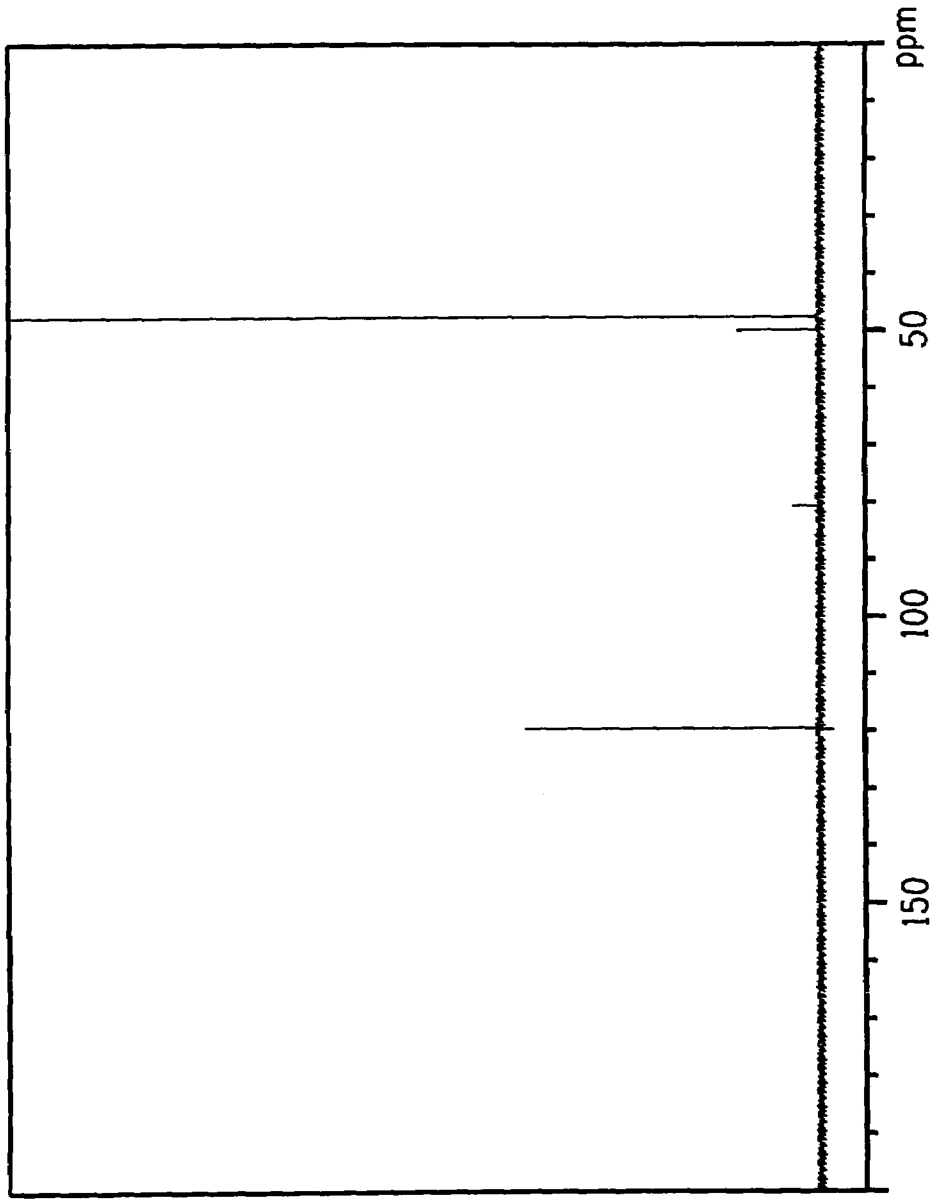
FIG. 6 shows $^{13}C$ NMR spectrum of the resulting glycolonitrile solution, qualitatively indicating the purity of the glycolonitrile product produced in Example 9.

FIG. 6 shows the $^{13}C$ NMR spectrum of the resulting glycolonitrile solution, qualitatively indicating the purity of the glycolonitrile product.

EXAMPLE 10

Pre-Heating 100% of Formaldehyde Continuous Feed

Approximately 0.40 mL of 16.7 wt % aqueous NaOH solution was added to 58.0 g of 37 wt % aqueous solution of formaldehyde (containing 7-8% methanol). The resulting solution was used for the continuous formaldehyde feed.

The reaction vessel, equipped with a magnetic stirbar, was initially charged with a mixture of 0.29 g HCN in 10.3 g water and placed within a water bath maintained at around 25° C., on top of a stirplate. The approximately 24-inch section of the formaldehyde feed line (⅛" OD×0.085" ID) directly preceding the inlet to the reaction flask was heated to 90° C. after filling the formaldehyde feed line. After establishing heated formaldehyde feed outside of the reaction vessel, the end of the formaldehyde feed line was placed directly into the liquid reaction mixture. The reaction temperature was maintained around 20-25° C., which was accomplished by periodically adding ice and/or dry ice to the external water bath. The reactants were each continuously pumped into the reaction vessel over a period of about 2.0 hr, as follows:

7.02 mL/hr of 50 wt % aqueous HCN solution (d=0.86 g/mL)

7.67 mL/hr of 37 wt % aqueous formaldehyde, described above (d=1.09 g/mL).

After 2.0 hr, the feeds were stopped, and the formaldehyde feed line was removed from the reaction product. The reaction mixture was removed from the reaction vessel and then quenched by adding of 0.10 mL of 70% Glypure® glycolic acid, resulting in a glycolonitrile product solution at about pH 3-4.

Figure 7:
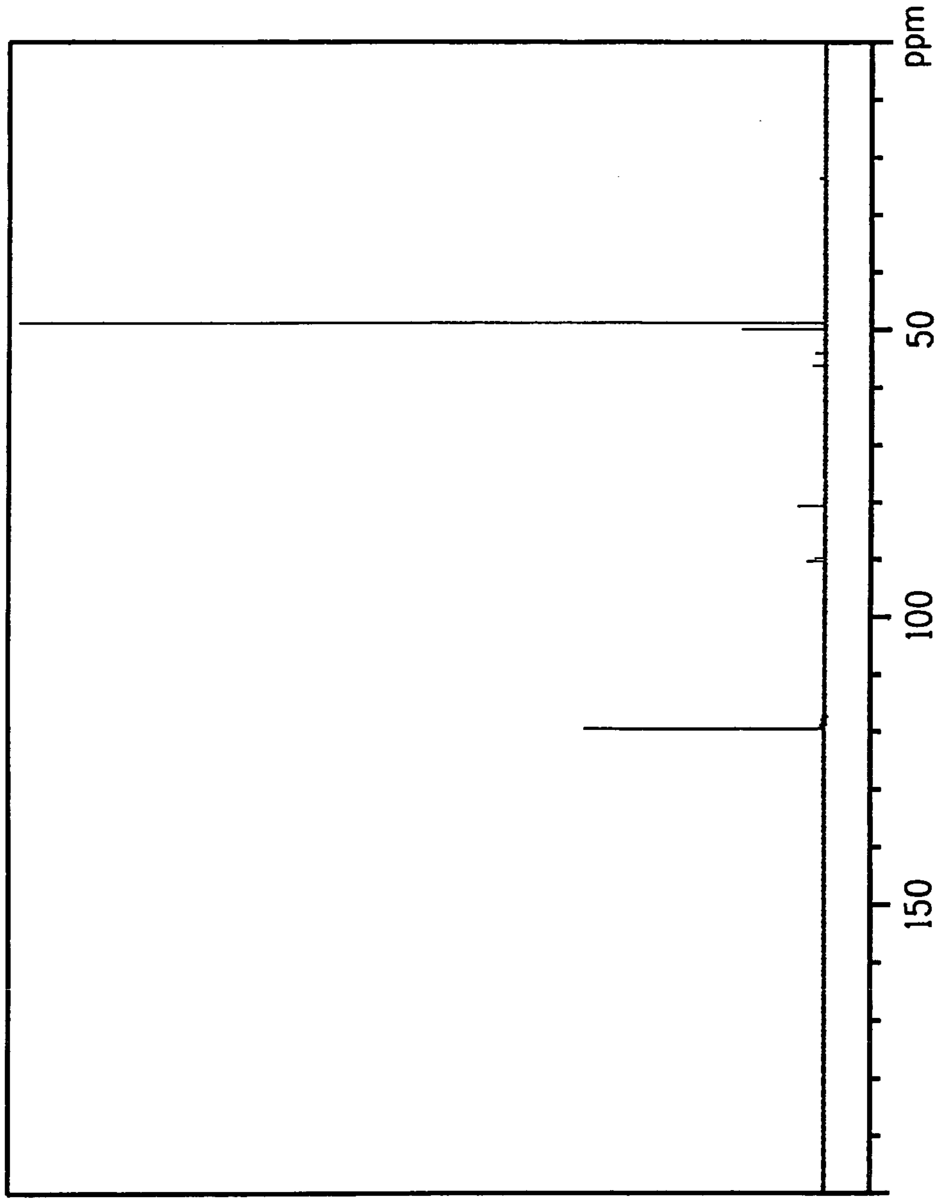
FIG. 7 shows $^{13}C$ NMR spectrum of the resulting glycolonitrile solution, qualitatively indicating the purity of the glycolonitrile product produced in Example 10.

FIG. 7 shows the $^{13}C$ NMR spectrum of the resulting glycolonitrile solution, qualitatively indicating the purity of the glycolonitrile product.

EXAMPLE 11

Construction of High Copy Nitrilase Expression Plasmid

Synthetic oligonucleotide primers

```
165 (5'-CGACTGCAGTAAGGAGGAATAGGACATGGTTTCGTATAACAG
CAAGTTC-3'; SEQ ID NO: 1)

and

166 (5'-TGATCTAGAGCTTGGAGAATAAAGGGGAAGACCAGAGATG-
3'; SEQ ID NO: 2)
```

which incorporate PstI and XbaI restriction sites (underlined), respectively) were used to PCR amplify the nitrilase gene from *A. facilis* 72W (ATCC 55746) genomic DNA (SEQ ID NO:5).

Typical PCR parameters are as follows:

Step 1: 5 minutes at 95° C.

Step 2: 0.5 minute at 95° C. (denaturation)

Step 3: 0.5 minute at 55° C. (annealing)

Step 4: 1 minute at 74° C. (extension)

Steps 2-4 are repeated 25 cycles

PCR reagents are supplied by and used as recommended by Roche Diagnostics Corporation (Indianapolis, Ind.).

The only change from native *Acidovorax facilis* 72W sequence is a change to the first nucleotide from G to A to facilitate expression in *E. coli*. In so doing, the start codon of the nitrilase gene was changed from the native GTG to ATG. Accordingly, the first amino acid of the corresponding nitrilase protein is changed from the native valine to methionine (SEQ ID NO: 6). Oligonucleotide primer 165 also introduces a ribosome binding site (bold) and a codon (TAG) to stop translation of lacZ prior to initiation of translation of nitrilase. The PCR product was digested with PstI and XbaI, and cloned into pUC19 (GenBank® L09137; New England Biolabs, Beverly, Mass.) digested with PstI and XbaI, to generate the plasmid identified as pSW138.

EXAMPLE 12

Expression of Active Nitrilase in *E. coli*

Plasmid pSW138 was used to transform *E. coli* MG1655 (ATCC 47076) and *E. coli* FM5 (ATCC 53911) to generate the two strains identified as (1) MG1655/pSW138 and (2) FM5/pSW138, respectively. Each strain was grown, induced, harvested, and assayed for nitrilase activity (conversion of glycolonitrile to glycolic acid) as described below. Replicates of six are performed for each strain.

1. Bacterial Growth

Strain inoculums were grown in LB media supplemented with ampicillin (50 mg/L), at 37° C. with shaking (200 rpm) for 16-18 hours.

2. Induction of Nitrilase Expression

Sufficient inoculum was added to fresh LB media supplemented with ampicillin (50 mg/L) and IPTG (1 mM) to give an initial OD (600 nm) of approximately 0.1. Cultures were incubated at 37° C. with shaking (200 rpm) for approximately 6-8 hours.

3. Bacterial Harvest

Bacterial cells were harvested by centrifugation, removing as much liquid as possible, and cell pellets were frozen at −70° C.

4. Assay for Nitrilase Activity

Into a temperature controlled (25° C.) 20-mL glass scintillation vial equipped with a micro stir bar was added 3.0 mL of substrate solution (0.667 M glycolonitrile; TCl) and 1.0 mL of cell suspension (400 mg wet cell weight/mL in 100 mM sodium pyrophosphate pH 6.0, 1 µg/mL DNAse). Final glycolonitrile concentration was 500 mM and final cell concentration was 100 mg/mL. Samples (100 µL) were removed at 5, 10, 15, 30, 45 and 60 min and added to assay mix (100 µL deionized water, 3 µL 6.0 N HCl, 200 µL 200 mM n-propanol), followed by vortexing and centrifugation. Resulting supernatants were analyzed by HPLC (HPX 87H column, 30 cm×7.8 mm; 0.01 N $H_2SO_4$ mobile phase; 1.0 mL/min flow at 50° C.; 10-µL injection volume; 20 min analysis time) for glycolonitrile (GLN) and glycolic acid (GLA) Dry cell weights (dcw) were determined on duplicate samples by microwave drying. Nitrilase activity was reported as U/g dcw, where 1 unit (U) converts 1 μmol of GLN to GLA in 1 min at 25° C. (Table 2).

TABLE 2

| Strain | Nitrilase activity (U/g dcw) |
|---|---|
| MG1655/pSW138 | 22.1 |
| FM5/pSW138 | 3.3 |

EXAMPLE 13

Construction of *A. facilis* 72W Nitrilase Random Mutagenesis Libraries by Error-Prone Polymerase Chain Reaction Genomic DNA was prepared from *A. facilis* 72W (ATCC 55746) using a Puregene® DNA isolation kit according to the manufacturer's instructions (Gentra Systems, Minneapolis, Minn.). Error-prone PCR was performed on the *A. facilis* 72W nitrilase gene (coding sequence; SEQ ID NO:5) using primers identified as SEQ ID NO: 3 (5'-GCGCATATG GTTTCGTATAACAGCAAGTTCC-3') and SEQ ID NO: 4 (5'-ATAGGATCCTTATGGCTACTTTGCTGGGACCG-3') according to instructions supplied with the GeneMorph® PCR Mutagenesis Kit (Stratagene, La Jolla, Calif.). Reaction conditions recommended to produce a low mutation frequency (0-3 mutations/kb) and a medium mutation frequency (3-7 mutations/kb) were employed. Ten percent of the 1.1 kb PCR product was ligated into the expression vector pTrcHis2 TOPO® according to instructions supplied with the pTrcHis2 TOPO® TA Expression kit (Invitrogen, Carlsbad, Calif.). One half of the ligation mixture was transformed into *E. coli* TOP10 according to supplier's recommendations (Invitrogen). One percent of the transformation mixture was plated onto LB plates supplemented with 50 mg/L ampicillin. Resultant transformants numbered 200-400 colonies, suggesting that the total PCR product produced was capable of generating 400,000-800,000 colonies, more than enough required to screen for improved enzyme activity. Mutation frequencies were confirmed by nucleotide sequence analysis of a randomly selected sample of clones. Sequence analysis also confirmed that approximately 50% of inserts were in the forward orientation, as expected. SDS-PAGE analysis confirmed that essentially all clones with forward orientation inserts expressed the ~41 kDa nitrilase protein when grown and induced as recommended (Invitrogen).

In addition, the native *A. facilis* 72W nitrilase gene was amplified by standard PCR using primers identified as SEQ ID NO: 3 and SEQ ID NO: 4, and the resulting DNA product was cloned into pTrcHis2-TOPO® (Invitrogen) according to manufacturer recommendations, to generate the plasmid pNM18. Transformation of *E. coli* TOP10 or *E. coli* FM5 (ATCC 53911) with pNM18 produced strains useful as respective controls. The *A. facilis* 72W nitrilase "control" sequence in pNM18 (SEQ ID NO: 5) is identical to the coding sequence of the wild-type *A. facilis* 72W except for a change in the start codon from GTG to ATG, facilitating expression in *E. coli*.

EXAMPLE 14

Screening *A. facilis* 72W Nitrilase Random Mutagenesis Libraries for Increased Nitrilase Activity Approximately 10,000 colonies from the low mutation frequency error-prone PCR library (constructed as described in Example 13) were plated on LB agar supplemented with 50 mg/L ampicillin. High throughput screening was performed in 96-well microtiter plates using robotics. After growth of individual colonies in liquid LB supplemented with 50 mg/L ampicillin and 1 mM IPTG (isopropyl-β-D-thiogalactopyranoside) for 18 h at 37° C., 200 rpm shaking, cultures were supplied with 50 mM glycolonitrile (GLN) for 1 h at 37° C., 80 Hz linear shaking. Reactions were stopped by filtering out the bacterial cells, and supernatants to be analyzed were sealed in microtiter plates and stored at 4° C. until analysis.

Production of glycolic acid (GLA) was measured by atmospheric pressure chemical ionization (APCI) mass spectrometry in the negative ion mode monitoring the M-H ion, m/z 75, in single ion mode. The mass spectrometer used was a Micromass (Waters) Quattro Ultima triple quad, with the following settings: source temperature=150° C., probe temperature=300° C., cone gas=80 L/hr, Desolvation gas=700-800 L/hr. Cone voltage=35 V, Corona voltage=20 mA. Multiplier=600 V, Dwell=0.1 s, Interchannel Delay=0.02 s. The mobile phase was 50/50 MeOH/$H_2O$ at 3.5 mL/min per needle with a 1:5 split of eluent before introduction into the mass spectrometer using a LC Packings Acurate splitter. Samples were delivered by a Gilson 215 auto-sampler with a 889 serial injection 8-valve bank injecting 30 mL of sample into 5-mL sample loops. A Hudson Plate Crane XT plate handling robot delivered plates to the deck of the Gilson auto-sampler. A needle and injection port wash with the same solvent at 5 mL/min was performed between each set of 8 injections. By this method, seven strains with increased nitrilase activity were identified and isolated.

EXAMPLE 15

Identification of Mutations in *A. facilis* 72W Nitrilase Conferring Increased Nitrilase Activity Nucleotide sequence analysis was used to identify any mutations present in the nitrilase gene of the seven TOP10 mutant strains isolated as described in Example 14, and the corresponding amino acid changes were deduced. All seven strains showed the identical nitrilase sequence (SEQ ID NO: 8), with a single amino acid change, Leu at position 201 changed to Gln (L201Q) in the plasmid identified as pNM18-201Q. This change had no detectable effect on nitrilase protein production (compared to the native enzyme), as measured by SDS-PAGE analysis.

EXAMPLE 16

Saturation Mutagenesis of Nitrilase at Amino Acid Residue Position 201

A saturation mutagenesis library at amino acid position 201 of the *A. facilis* 72W nitrilase enzyme was constructed using degenerate oligonucleotides and the QuikChange® Site-Directed Mutagenesis Kit (Stratagene, La Jolla, Calif.) according to the manufacturer's instructions. Approximately 500 members of this library were screened for increased nitrilase activity as previously described (Example 14).

Nucleotide sequencing analysis was used to determine any amino acid changes at position 201 that conferred increased nitrilase activity. In addition to L201Q (SEQ ID NO: 8), the following mutations conferring increased nitrilase activity were identified from the screen: L201G (SEQ ID NO: 16), L201H (SEQ ID NO: 18), L201K (SEQ ID NO: 20), L201N (SEQ ID NO: 22), L201S (SEQ ID NO: 24), L201A (SEQ ID NO:10), L201C (SEQ ID NO: 12), and L201T (SEQ ID NO: 14) in the plasmids identified as pNM18-201G, pNM18-201H, pNM18-201K, pNM18-201N, pNM18-201S, pNM18-201A, pNM18-201C, and pNM18-201T, respectively.

EXAMPLE 17

Targeted Saturation Mutagenesis of the *A. facilis* 72W Nitrilase Catalytic Domain We hypothesized that the catalytic domain within the *A. facilis* 72W nitrilase (SEQ ID NO: 6) may be a suitable region to mutate in an attempt to increase nitrilase activity toward 2-hydroxynitriles, namely glycolic acid.

Saturation mutagenesis within the *A. facilis* 72W nitrilase (SEQ ID NO: 6) catalytic domain (160G 161<u>G</u> 162L 163<u>N</u> 164C 165<u>W</u> 166E 167<u>H</u> 168<u>F</u> 169<u>Q</u> 170<u>P</u> 171L 172<u>S</u> 173<u>K</u>) of those residues not universally conserved among known bacterial nitrilases (underlined) was completed using degenerate oligonucleotides and the QuikChange® Site-Directed Mutagenesis Kit (Stratagene, La Jolla, Calif.) according to the manufacturer's instructions. Specifically, nine mini-libraries (500-1000 colonies) were constructed, one for each of the active site residues targeted (underlined above). These libraries were screened for increased nitrilase activity as previously described. Nucleotide sequencing analysis was used to determine any amino acid changes that conferred increased nitrilase activity. The following changes conferring increased nitrilase activity were identified: F168K (SEQ ID NO: 26), F168M (SEQ ID NO: 28), F168T (SEQ ID NO: 30), and F168V (SEQ ID NO: 32) in the plasmids identified as pNM18-168K, pNM18-168M, pNM18-168T, and pNM18-168V, respectively.

EXAMPLE 18

Construction of MG1655/pSW138-168K, MG1655/pSW138-168M, MG1655/pSW138-168T, MG1655/pSW138-168V, MG1655/pSW138-201Q, MG1655/pSW138-201G, MG1655/pSW138-201H, MG1655/pSW138-201K, MG1655/pSW138-201N, and MG1655/pSW138-201S Each of the plasmids pNM18-168K, pNM18-168M, pNM18-168T, pNM18-168V, pNM18-201Q, pNM18-201G, pNM18-201H, pNM18-201K, pNM18-201N, and pNM18-201S was cleaved with EcoRI and the smaller EcoRI fragment (907 bp) was subcloned into the plasmid pSW138 (described in Example 11) which had also been cleaved with EcoRI, to generate the plasmids pSW138-168K, pSW138-168M, pSW138-168T, pSW138-168V, pSW138-201Q, pSW138-201G, pSW138-201H, pSW138-201K, pSW138-201N, and pSW138-201S, respectively. Each of the plasmids pSW138-168K, pSW138-168M, pSW138-168T, pSW138-168V, pSW138-201Q, pSW138-201G, pSW138-201H, pSW138-201K, pSW138-201N, and pSW138-201S was used to transform *E. coli* MG1655 to generate the strains MG1655/pSW138-168K, MG1655/pSW138-168M, MG1655/pSW138-168T, MG1655/pSW138-168V, MG1655/pSW138-201Q, MG1655/pSW138-201G, MG1655/pSW138-201H, MG1655/pSW138-201K, MG1655/pSW138-201N, and MG1655/pSW138-201S; respectively.

EXAMPLE 19

Nitrilase Activity of Mutants Produced by 10-Liter Fermentation

*E. coli* seed cultures were grown in 500 mL LB media supplemented with 0.1 mg ampicillin per mL for 6-10 h ($OD_{550}$=1-2) at 30° C. with shaking (300 rpm) prior to inoculation of the fermentor.

Growth of nitrilase strains was in 14-L Braun Biostat C fermentors (B. Braun Biotech International Gmbh, Melsungen, Germany) using mineral medium with glucose, ammonia, and salts. IPTG (for FM5/pNM18 based strains) or lactose (for MG1655/pSW138 based strains) was used for induction.

Pre-sterilization fermentor media (7.5 L) is described in Table 3. Post-sterilization additions include filter sterilized trace elements (Table 4), 0.1 mg ampicillin per mL, 2 g casamino acids (Difco) per L, 4 g glucose per L, and 500 mL seed culture.

Fermentation set points are described in Table 5. $NH_4OH$ (40% w/v) and $H_2PO_4$ (20% w/v) were used for pH control. The dissolved oxygen concentration was controlled at 25% of air saturation with the agitation to rise first with increase oxygen demand and the aeration to follow. The fermentation feed protocols used with IPTG induction and lactose induction are given in Tables 6 and 7, respectively. Glucose feed rates were reduced if glucose accumulated above 5 g/L. For FM5/pNM18 based strains, IPTG was added to 0.5 mM at $OD_{550}$=20-30. After 40-56 hrs cells were chilled to 5-10° C. and harvested by centrifugation. Nitrilase activity was determined as described (Example 12) and results are shown in Table 8.

TABLE 3

Fermentation media, pre-sterilization.

| | |
|---|---|
| $(NH_4)_2SO_4$ | 5.0 g/L |
| $K_2HPO_4$ | 4.0 g/L |
| $KH_2PO_4$ | 3.5 g/L |
| $MgSO_4*7H_2O$ | 0.6 g/L |
| $Na_3Citrate*2H_2O$ | 1.0 g/L |
| NZ Amine AS (Quest) | 2.5 g/L |
| Antifoam - Biospumex 153K | 0.25 mL/L |

TABLE 4

Fermentation trace elements

| | Concentration |
|---|---|
| Citric acid | 10 g/L |
| $CaCl_2*2H_2O$ | 1.5 g/L |
| $FeSO_4*7H_2O$ | 5 g/L |
| $ZnSO_4*7H_2O$ | 0.39 g/L |
| $CuSO_4*5H_2O$ | 0.38 g/L |
| $CoCl_2*6H_2O$ | 0.2 g/L |
| $MnCl_2*4H_2O$ | 0.3 g/L |

TABLE 5

| Fermentation set points | | | |
|---|---|---|---|
| | Initial Set-Point | Minimum | Maximum |
| Stirrer (rpm) | 400 | 400 | 1000 |
| Airflow (slpm) | 2 | 2 | 10 |
| pH | 6.8 | 6.8 | 6.8 |
| Pressure (kPa) | 0.5 | 0.5 | 0.5 |
| DO | 25% | 25% | 25% |
| Temperature ° C. | 30 | 30 | 30 |

TABLE 6

| Fermentation feed protocol used with IPTG induction | | |
|---|---|---|
| EFT (hr) | Feed Rate (g/min) | Substrate |
| 0 | 0 | Glucose (batched) |
| 5 | 0.27 | Glucose (50% w/w) |

TABLE 7

| Fermentation feed protocol used with lactose induction | | |
|---|---|---|
| EFT (hr) | Feed Rate (g/min) | Substrate |
| 0 | 0 | Glucose (batched) |
| 5 | 0.27 | Glucose (50% w/w) |
| 14 | 1.3 | Lactose (25% w/w) |

TABLE 8

| Nitrilase Activity for Mutants Grown in 10-Liter Fermentations | | | |
|---|---|---|---|
| Mutation (SEQ ID NO.) | *E. coli* Strain | Nitrilase Activity (GLA U/ g dcw) | Fold Increase vs. Respective Control |
| None (SEQ ID NO: 6) | FM5/pNM18 (control) | 387 | NA |
| None (SEQ ID NO: 6) | MG1655/pSW138 (control) | 490 | NA |
| F168K (SEQ ID NO: 26) | FM5/pNM18-168K | 1250 | 3.2 |
| F168K (SEQ ID NO: 26) | MG1655/pSW138-168K | 1230 | 2.5 |
| F168M (SEQ ID NO: 28) | MG1655/pSW138-168M | 1261 | 2.6 |
| F168T (SEQ ID NO: 30) | FM5/pNM18-168T | 2152 | 5.6 |
| F168T (SEQ ID NO: 30) | MG1655/pSW138-168T | 837 | 1.7 |
| F168V (SEQ ID NO: 32) | MG1655/pSW138-168V | 1763 | 3.6 |
| L201Q (SEQ ID NO: 8) | FM5/pNM18-201Q | 2603 | 6.7 |
| L201Q (SEQ ID NO: 8) | MG1655/pSW138-201Q | 2410 | 4.9 |
| L201G (SEQ ID NO: 16) | FM5/pNM18-201G | 2985 | 7.7 |
| L201H (SEQ ID NO: 18) | FM5/pNM18-201H | 2322 | 6.0 |
| L201H (SEQ ID NO: 18) | MG1655/pSW138-201H | 1334 | 2.7 |
| L201K (SEQ ID NO: 20) | FM5/pNM18-201K | 4434 | 11.5 |

TABLE 8-continued

| Nitrilase Activity for Mutants Grown in 10-Liter Fermentations | | | |
|---|---|---|---|
| Mutation (SEQ ID NO.) | *E. coli* Strain | Nitrilase Activity (GLA U/ g dcw) | Fold Increase vs. Respective Control |
| L201N (SEQ ID NO: 22) | FM5/pNM18-201N | 2542 | 6.6 |
| L201N (SEQ ID NO: 22) | MG1655/pSW138-201N | 2695 | 5.5 |
| L201S (SEQ ID NO: 24) | FM5/pNM18-201S | 1463 | 3.8 |

EXAMPLE 20

Determination of Nitrilase Activity for *E. coli* TOP10/pNM18, *E. coli* TOP10/pNM18-201A, *E. coli* TOP10/pNM18-201C, and *E. coli* TOP10/pNM128-201T (Shake Flask)

In duplicate, 10 mL of an overnight culture (LB+50 µg/mL ampicillin, 37° C. with shaking) was added to 200 mL (LB+50 ug/ml ampicillin+1 mM IPTG) and incubated at 37° C. with shaking for 4-5 hrs (final OD600 approximately 2.0). Cells were collected by centrifugation at 4° C. and stored frozen at −80° C.

To a 4-mL glass vial equipped with a magnetic stir bar was added 1.0 mL of 1.0 M glycolonitrile in water, and the vial and its contents equilibrated to 25° C. in a temperature controlled water bath. With stirring, 1.0 mL of 0.100 M potassium phosphate buffer (pH 7.0) containing 40-100 mg wet cell paste pre-equilibrated to 25° C. was added to the vial (final [GLN]=0.5M). Samples (0.100 mL) were taken at predetermined times and mixed with a solution comprised of 0.100 mL water, 0.020 mL of 6.0 N acetic acid and 0.200 mL of 0.20 M sodium butyrate in water (HPLC external standard). The resulting mixture was centrifuged and the resulting supernatant analyzed by HPLC for glycolic acid using a Supelco® (Sigma Aldrich Corp.) LC-18-DB column (15 cm×4.6 mm): mobile phase: aqueous 10 mM sodium acetate (NaOAc), 10 mM acetic acid (AcOH), 7.5% (v/v) methanol. The dry cell weight (dcw) of each cell paste was determined and used to calculate cell-specific nitrilase activity. Table 9 summarizes the increases in nitrilase activity for the nitrilase mutants compared to the native nitrilase.

TABLE 9

| Nitrilase activity for mutants L201A, L201C, and L201T versus control (shake flasks). | | | |
|---|---|---|---|
| Mutation (SEQ ID NO.) | *E. coli* strain | Nitrilase Activity (GLA U/g dcw) | Fold Increase in activity (vs. control) |
| None (SEQ ID NO: 6) | TOP10/pNM18 (Control) | 135 | NA |
| L201A (SEQ ID NO: 10) | TOP10/pNM18-201A | 371 | 2.7 |
| L201C (SEQ ID NO: 12) | TOP10/pNM18-201C | 289 | 2.1 |
| L201T (SEQ ID NO: 14) | TOP10/pNM18-201T | 308 | 2.3 |

EXAMPLE 21

Preparation of Immobilized *E. coli* SS1001 (ATCC PTA-1177)

*E. coli* strain SS1001 (ATCC PTA-1177) is a transformed *E. coli* strain expressing the *Acidovorax facilis* 72W nitrilase (U.S. Pat. No. 6,870,038; herein incorporated by reference). The coding sequence of the recombinantly expressed (*E. coli* SS1001) nitrilase (SEQ ID NOs: 37-38) contains 2 minor sequence changes in comparison to the wild-type 72W nitrilase sequence (SEQ ID NO: 5). The start codon was changed from GTG to ATG to facilitate recombinant expression and an artifact was introduced during cloning that resulted in a single amino acid change near the C-terminal (Pro367 [CCA]→Ser [TCA];).

This strain was grown in a 10-L fermentation as previously described (see Example 8 of U.S. Ser. No. 10/919,182), and the cell paste (glycolonitrile (GLN) was used in a process to convert GLN to glycolic acid (GLA) as follows.

*E. coli* SS1001 cells were first immobilized in carrageenan beads (the immobilized *E. coli* SS1001) according to the following procedure. With rapid stirring, 9 g of carrageenan (FMC GP911; FMC Corp., Philadelphia, Pa.) was slowly added to 231 g deionized distilled water at 50° C., the resulting mixture heated to 80° C. until carrageenan was completely dissolved, and the resulting solution cooled with stirring to 47° C. In a separate beaker equipped with stir bar, 75.9 g of frozen *E. coli* SS1001 cells (39.53% dcw) was added to 84.1 g of 0.35 M $Na_2HPO_4$ (pH 7.3) at ca. 25° C. and mixed until the cells were suspended, then a deoxyribonuclease I solution (10 μL of 12,500 U/mL DNase (Sigma Aldrich, St. Louis, Mo.)/100 mL of cell suspension) was added. The cell suspension was heated with stirring to 45-46° C. immediately before addition to carrageenan solution. With stirring, 160.0 g of *E. coli* SS1001 cell suspension at 47° C. was added to the carrageenan solution at 47° C., and the resulting cell/carrageenan suspension was pumped through an electrically-heated 20 gauge needle at 47° C. and dripped into 0.25 M $KHCO_3$ (pH=7.3) with stirring at room temperature (ca. 21-22° C.); the flow rate through the needle was set at 5-8 mL/min. The resulting beads were allowed to harden for 1 h with stirring, and were stored in 0.25 M $KHCO_3$ (pH 7.3). Chemical crosslinking of the beads was performed by addition of 0.5 g of 25% glutaraldehyde (GA) in water (Sigma M 752-07) to 20 g beads suspended in 48 mL of 0.25 M $KHCO_3$ (pH 7.3), and stirring for 1 h at room temperature. To the suspension of beads was then added 2.0 g of 12.5 wt % polyethylenimine (PEI, BASF LUPASOL PS; BASF Aktiengesellschaft, Ludwigshafen, Germany) in water followed by mixing for an additional 1 h at room temperature. The GA/PEI-crosslinked beads were stored in 1.0 M $NH_4HCO_3$ (pH 7.3) at 5° C.

Biocatalytic conversion of GLN to GLA was followed by HPLC. Aliquots (0.2 mL) of the reaction mixture were added to 0.01 mL 6 M HCl and 0.8 mL of 0.25 M n-propanol in water (HPLC external standard), and analyzed by HPLC (HPX 87H column (Bio-Rad, Hercules, Calif.), 30 cm×7.8 mm; 0.01 N $H_2SO_4$ mobile phase; 1.0 mL/min flow at 50° C.; 10 μL injection volume; refractive index (RI) detector, 20 min analysis time) for GLN and GLA. The nitrilase activity of the GA/PEI-crosslinked carrageenan/7.5% (dcw) *E. coli* SS1001 beads, was ~12 U/g beads, where 1 unit (U) converts 1 μmol of GLN to GLA in 1 min at 25° C.

EXAMPLE 22

Conversion of 1 M Glycolonitrile (GLN) to Ammonium Glycolate ($NH_4GLA$)

A 50-mL jacketed reaction vessel with overhead stirring was charged with 4 g *E. coli* SS1001 beads (Example 21), 13.73 mL deionized water, 0.4 mL 5 M $NH_4GLA$, and 1.87 mL GLN (ca. 52 wt % in water (TCI)), 0.89 M GLN final concentration, pH adjusted to pH 7.6, the mixture stirred at 25° C., and 0.2 mL aliquots were taken out to follow the reaction progress by HPLC. When all GLN was converted to $NH_4GLA$, product solution was decanted, 14.13 mL deionized water and 1.87 mL GLN were added to biocatalyst, pH adjusted to pH 7.6, and biocatalyst recycle was repeated. The initial rate of $NH_4GLA$ synthesis at the first biocatalyst recycle was 143 mM/h. Percent decrease in initial rate of $NH_4GLA$ synthesis vs. the recycle number are shown in Table 10 ("1 M").

EXAMPLE 23

Conversion of Approximately 3 M Glycolonitrile (GLN) to Ammonium Glycolate ($NH_4GLA$)

A 50-mL jacketed reaction vessel with overhead stirring was charged with 4 g *E. coli* SS1001 beads (Example 11), 6.39 mL deionized water, 4 mL 1 M $KHCO_3$, and 5.61 mL GLN (ca. 52 wt % in water (TCl)), 2.68 M GLN final concentration, pH was adjusted to pH 7.6, the mixture stirred at pH 25° C., and 0.2 mL aliquots were taken out to follow the reaction progress by HPLC. When all GLN was converted to $NH_4GLA$, product solution was decanted, 6.39 mL deionized water, 4 mL 1 M $KHCO_3$, and 5.61 mL GLN were added to biocatalyst, pH adjusted to pH 7.6, and biocatalyst recycle was repeated. The initial rate of $NH_4GLA$ synthesis at the first biocatalyst recycle was 207 mM/h. Percent decrease in initial rate of $NH_4GLA$ synthesis vs. the recycle number are shown in Table 10 ("3 M").

EXAMPLE 24

Addition of Approximately 3 M Glycolonitrile in Approximately 1 M Increments (1 M+1 M+1 M) to Yield Ammonium Glycolate ($NH_4GLA$)

A 50-mL jacketed reaction vessel with overhead stirring was charged with 4 g *E. coli* SS1001 beads (Example 21), 8.13 mL deionized water, 4 mL 1 M $KHCO_3$, and 1.87 mL GLN (ca. 52 wt % in water (TCI)), 0.89 M GLN, pH was adjusted to pH 7.6, the mixture stirred at 25° C., and 0.2 mL aliquots were taken out to follow the reaction progress by HPLC. When all GLN was converted to $NH_4GLA$, second portion of 1.87 mL GLN was added, pH was adjusted to pH 7.6, and when all GLN was consumed, the third portion of 1.87 mL GLN was added, pH adjusted to pH 7.6, and reaction completed yielding approximately 3 M $NH_4GLA$ solution. Product solution was decanted, 8.13 mL deionized water, 4 mL 1M $KHCO_3$, and 1.87 mL GLN were added to biocatalyst, pH adjusted to pH 7.6, GLN conversion proceeded to completion, and addition of GLN, water and buffer, pH adjustment, and completion of GLN conversion were repeated twice more to finish the recycle (step-wise conversion of GLN in three approximately 1 M increments), and biocatalyst recycles were repeated. The initial rate of $NH_4GLA$ synthesis in the first 1 M GLN solution in a first recycle (three ~1 M portions of GLN per recycle) was 155 mM/h. Percent decrease in initial rate of $NH_4GLA$ synthesis vs. the recycle number are shown in Table 10 ("(1 M+1 M+1 M)=3 M").

EXAMPLE 25

Continuous Addition of Glycolonitrile (GLN) to 0.2 M GLN to Yield Ammonium Glycolate ($NH_4GLA$)

A 50-mL jacketed reaction vessel with overhead stirring was charged with 4 g *E. coli* SS1001 beads (Example 21), 8 mL deionized water, 4 mL 1 M $KHCO_3$, and 0.4 mL GLN (ca. 52 wt % in water (TCI)), pH was adjusted to pH 7.6, the mixture stirred at 25° C., GLN solution was continuously added up to 3 M GLN at a rate of GLN consumption to keep GLN concentration around 0.2 M, and 0.2 mL aliquots were taken out to follow the reaction progress by HPLC. When all GLN was converted to $NH_4GLA$, product solution was decanted, 8 mL deionized water, 4 mL 1M $KHCO_3$, and 0.4 mL GLN were added to biocatalyst, pH adjusted to pH 7.6, and a new biocatalyst recycle was repeated with GLN addition up to 3 M GLN at a rate of GLN consumption. The initial rate of $NH_4GLA$ synthesis for the first biocatalyst recycle (3 M GLN total per recycle) was 144 mM/h. Percent decrease in initial rate of $NH_4GLA$ synthesis vs the recycle number are shown in Table 10 ("0.2 M Continuous").

Table 10. Percent decrease in initial rate of $NH_4GLA$ synthesis vs. recycle number at 3 M GLN, 1 M GLN, addition of 3 M GLN in three 1 M increments, and at continuous addition of GLN starting with 0.2 M GLN (nd=not determined).

TABLE 10

Percent decrease in initial rate of $NH_4GLA$ ssynthesis vs. recycle number at 3 M GLN, 1 M GLN, addition of 3 M GLN in three 1 M increments, and at continuous addition of GLN starting with 0.2 M GLN

| Reaction # (reactions 2-19 are recycle reactions with the same catalyst as in reaction 1) | 3 M GLN (% initial reaction rate) | 1 M GLN (% initial reaction rate) | (1 M + 1 M + 1 M) = 3 M GLN (% initial reaction rate) | 0.2 M Continuous Feed GLN (% initial reaction rate) |
|---|---|---|---|---|
| 1 | 100 | 100 | 100 | 100 |
| 2 | 62 | nd | 89 | 95 |
| 3 | nd | 75 | nd | 56 |
| 4 | 7 | 95 | 88 | 52 |
| 5 | | nd | nd | |
| 6 | | 78 | nd | |
| 7 | | nd | 59 | |
| 8 | | 79 | | |
| 9 | | nd | | |
| 10 | | nd | | |
| 11 | | nd | | |
| 12 | | nd | | |
| 13 | | 44 | | |
| 14 | | nd | | |
| 15 | | nd | | |
| 16 | | nd | | |
| 17 | | nd | | |
| 18 | | 29 | | |
| 19 | | 25 | | |

(nd = not determined).

EXAMPLE 26

Preparation of GA/PEI-crosslinked carrageenan/*E. coli* FM5/pNM18-210A Beads Comprised of Different Levels of Cross-Linking The plasmid pNM18-210A, which expresses the nitrilase mutant 210Ala (SEQ ID NO: 34) from the plasmid pTrcHis2-TOPO® was used to transform *E. coli* FM5, to generate the strain identified as FM5/pNM18-210A. This strain was grown in a 10-L fermentation as previously described (see Example 8 of U.S. Ser. No. 10/919,182; herein incorporated by reference), and the cell paste was used in a process to convert GLN to glycolic acid (GLA) as follows.

*E. coli* FM5/pNM18-210A cells were first immobilized in carrageenan beads according to the following procedure. With rapid stirring, 12 g of carrageenan (FMC GP911) was slowly added to 228 g deionized distilled water at 50° C., the resulting mixture heated to 80° C. until carrageenan was completely dissolved, and the resulting solution cooled with stirring to 52° C. In a separate beaker equipped with stir bar, 74.9 g of frozen *E. coli* FM5/pNM18-210A cells (26.7% dcw) was added to 8.51 g of 0.35 M $Na_2HPO_4$ (pH 7.3) at ca. 25° C. and mixed until the cells were suspended, then a deoxyribonuclease I solution (10 μL of 12,500 U/mL DNase (Sigma)/100 mL of cell suspension) was added. The cell suspension was filtered consecutively through a 230 micron and 140 micron Nupro TF strainer element filter, and heated with stirring to 50° C. immediately before addition to carrageenan solution. With stirring, 160.0 g of *E. coli* FM5/pNM18-210A cell suspension at 50° C. was added to the carrageenan solution at 52° C., and the resulting cell/carrageenan suspension was pumped through an electrically-heated 20 gauge needle at 47° C. and dripped into 0.25 M $KHCO_3$ (pH=7.3) with stirring at room temperature (ca. 21-22° C.); the flow rate through the needle was set at 5-8 mL/min. The resulting beads were allowed to harden for 1 h with stirring, and were stored in 0.25 M $KHCO_3$ (pH 7.3). Chemical crosslinking of the beads was performed by either addition of 0.5 g (hereinafter referred to as "Biocatalyst 1") or 2.0 g (hereinafter referred to as "Biocatalyst 2") of 25% glutaraldehyde (GA) in water (Sigma M 752-07) to 20 g beads suspended in 48 mL of 0.25 M $KHCO_3$ (pH 7.3), and stirring for 1 h at room temperature. To the suspension of beads was then added either 2.0 g (Biocatalyst 1) or 4.0 g (Biocatalyst 2) of 12.5 wt % polyethylenimine (PEI, BASF LUPASOL PS) in water, and mixing for an additional 18 h at room temperature. The GA/PEI-crosslinked beads were stored in 1.0 M $NH_4HCO_3$ (pH 7.3) at 5° C.

Biocatalytic conversion of GLN to GLA was followed by HPLC. Aliquots (0.2 mL) of the reaction mixture were added to 0.01 mL 6 M HCl and 0.8 mL of 0.25 M n-propanol in water (HPLC external standard), and analyzed by HPLC (HPX 87H column, 30 cm×7.8 mm; 0.01 N $H_2SO_4$ mobile phase; 1.0 mL/min flow at 50° C.; 10 μL injection volume; RI detector, 20 min analysis time) for GLN and GLA. The nitrilase activity of the GA/PEI-crosslinked carrageenan/5% (dcw) *E. coli* FM5/pNM18-210A beads for both Biocatalyst 1 and Biocatalyst 2, was ~13 U/g beads, where 1 unit (U) converts 1 μmol of GLN to GLA in 1 min at 25° C.

EXAMPLE 27 (COMPARATIVE)

Conversion of Glycolonitrile (GLN) to Ammonium Glycolate ($NH_4GLA$) without Additives in Air A 50-mL jacketed reaction vessel with overhead stirring was charged with 4 g Biocatalyst 1, 12.42 mL deionized water, 0.5 mL 4 M $NH_4GLA$, and 1.78 mL GLN (ca. 52 wt % in water (Fluka)), 1 M GLN final concentration, at pH 7.6, the mixture stirred at 25° C., and 0.2 mL aliquots were taken out to follow the reaction progress by HPLC. When all GLN was converted to $NH_4GLA$, second portion of 1.78 mL GLN was added, pH was adjusted to pH 7.6 with ammonium hydroxide, and when all GLN was consumed, the third portion of 1.78 mL GLN was added, pH adjusted to pH 7.6, and reaction completed yielding 3.1 M $NH_4GLA$ solution. Product solution was decanted, 12.42 mL deionized water and 1.78 mL GLN were added to biocatalyst, pH adjusted to pH 7.6, GLN conversion proceeded to completion, and addition of GLN, pH adjustment, and completion of GLN conversion were repeated twice more to finish the recycle (step-wise conversion of GLN in three 1 M increments), and biocatalyst recycles were repeated. Percent decrease in initial rate of conversion of the first 1 M GLN solution in the recycle vs recycle number are shown in Table 11 (recycle reactions are reactions 2 through 8).

EXAMPLE 28

Conversion of Glycolonitrile (GLN) to Ammonium Glycolate ($NH_4GLA$) without Additives in Oxygen-Free Environment A 50-mL jacketed reaction vessel with overhead stirring under nitrogen was charged with 4 g Biocatalyst 1, 12.42 mL deionized water, 0.5 mL 4 M $NH_4GLA$, and 1.78 mL GLN (ca. 52 wt % in water (Fluka)), 1 M GLN final concentration, at pH 7.6, the mixture stirred at 25° C., and 0.2 mL aliquots were taken out to follow the reaction progress by HPLC. When all GLN was converted to $NH_4GLA$, 1.78 ml GLN and 0.2 mL water were added, pH was adjusted to pH 7.6 with ammonium hydroxide, and when all GLN was consumed, the third portion of 1.78 mL GLN and 0.2 mL deionized water were added, pH adjusted to pH 7.6, and reaction completed, yielding 3.1 M $NH_4GLA$ solution. Product solution was decanted, 12.62 mL deionized water and 1.78 mL GLN were added to biocatalyst, pH adjusted to pH 7.6, GLN conversion proceeded to completion, and addition of 1.78 mL GLN and 0.2 mL deionized water, pH adjustment, conversion of GLN to completion were repeated twice more to finish the recycle (step-wise conversion of GLN in three increments), and biocatalyst recycles were repeated. The percent decreased in the initial rate for conversion of the first 1 M GLN solution in a recycle vs the recycle number are shown in Table 11 (recycle reactions are reactions 2 through 8).

EXAMPLE 29

Converting Glycolonitrile (GLN) to Ammonium Glycolate ($NH_4GLA$) in the Presence of Thiosulfate or Dithionite in Oxygen-Free Environment Biocatalyst recycles were performed as described in Example 28 except instead of 12.42 mL of deionized water, 12.22 mL of deionized water and 0.2 mL of 1 M solution of additive (potassium thiosulfate, $K_2S_2O_3$ or sodium dithionite, $K_2S_2O_4$,) in water were added to start the recycle, and instead of 0.2 mL water, 0.2 mL 1 M solution of additive in water was added to reaction vessel along with each addition of 1.78 mL GLN. Percent decrease in initial rate for conversion of the first 1 M GLN solution in a recycle vs the recycle number are shown in Table 11 (recycle reactions are reactions 2 through 8).

TABLE 11

Percent decrease in initial rate of $NH_4GLA$ synthesis for conversion of the first 1 M GLN solution in a recycle reaction (3 M GLN total per recycle) vs the recycle reaction number after addition of thiosulfate or dithionite to the reaction under nitrogen, or for GLN conversion without additives under nitrogen or in air (nd = not determined).

| Reaction # | $K_2S_2O_3/N_2$ (% initial reaction rate) | $Na_2S_2O_4/N_2$ (% initial reaction rate) | control/$N_2$ (% initial reaction rate) | control/air (% initial reaction rate) |
|---|---|---|---|---|
| 1 | 100 | 100 | 100 | 100 |
| 2 | 114 | 96 | 77 | 116 |
| 3 | 104 | 91 | 97 | 81 |
| 4 | 101 | 76 | 112 | nd |
| 5 | 104 | 72 | 74 | 66 |
| 6 | 102 | 79 | 74 | nd |
| 7 | 86 | 64 | 63 | 7 |
| 8 | 92 | 74 | 68 | |

EXAMPLE 30

Conversion of Glycolonitrile (GLN) to Ammonium Glycolate ($NH_4GLA$) without Additives in Air at pH 6.0

A 50-mL jacketed reaction vessel with overhead stirring was charged with 4 g Biocatalyst 1, 12.42 mL deionized water, 0.5 mL 4 M $NH_4GLA$, and 1.78 mL GLN (ca. 52 wt % in water (Fluka)), 1 M GLN final concentration, at pH 6.0, the mixture stirred at 25° C., and 0.2 mL aliquots were taken out to follow the reaction progress by HPLC. When all GLN was converted to $NH_4GLA$, second portion of 1.78 mL GLN was added, pH was adjusted to pH 6.0 with ammonium hydroxide, and when all GLN was consumed, the third portion of 1.78 mL GLN was added, pH adjusted to pH 6.0, and reaction completed yielding 3.1 M $NH_4GLA$ solution. Product solution was decanted, 12.42 mL deionized water and 1.78 mL GLN were added to biocatalyst, pH adjusted to pH 6.0, GLN conversion proceeded to completion, and addition of GLN, pH adjustment, and completion of GLN conversion were repeated twice more to finish the recycle (step-wise conversion of GLN in three increments), and biocatalyst recycles were repeated. Decrease in initial rate of conversion of the first 1 M GLN solution in the recycle vs recycle number for Biocatalyst 1 are shown in Table 12 (recycle reactions are reactions 2 through 4)

TABLE 12

Percent decrease in initial rate of $NH_4GLA$ synthesis for conversion of first 1 M GLN solution in a recycle (3 M GLN total per recycle) vs the recycle number at pH 6.0 for Biocatalyst 1.

| Reaction # | Biocatalyst 1 (*E. coli* FM5/pNM18-210A) pH 6.0 (% initial reaction rate) |
|---|---|
| 1 | 100 |
| 2 | 71 |
| 3 | 50 |
| 4 | 24 |

EXAMPLE 31

Conversion of Glycolonitrile (GLN) to Ammonium Glycolate ($NH_4GLA$) Using Immobilized *E. coli* MG1655/pSW138 Cells Expressing *A. facilis* 72W Nitrilase at Various Reaction pHs A 50-mL jacketed reaction vessel equipped with overhead stirring and temperature control was charged with 4 g of GA/PEI-crosslinked carrageenan beads (prepared using the process as described in Example 21), washed twice for 15 min with 72 mL of 0.1 M $NH_4GLA$ (pH 7.0)) containing 5% (dcw) *E. coli* MG1655/pSW138 expressing the *A. facilis* 72W nitrilase (SEQ ID NO: 6). To the vessel was then added 10.88 g of distilled water and 2.98 mL 4.0 M $NH_4GLA$ (pH 7.5), the appropriate amounts of either 70 wt % glycolic acid (GLA) (Aldrich) or 1:4 dilution of ammonium hydroxide (28-30 wt %) in water (Table 13), and the reaction vessel was flushed with nitrogen. The mixture was stirred at 25° C. and 2.15 mL of 49.88 wt % glycolonitrile (GLN) in water (2.25 g, 19.6 mmol (Fluka)) was added to yield 1 M GLN at pH 4.0, 4.7, 5.5, 6.7, or 7.5 (Table 14).

Four 0.100-mL reaction samples were removed at predetermined times after the GLN addition and analyzed by HPLC to determine the initial reaction rate. The initial reaction rates as an average of rates in duplicate runs at each pH are listed in Table 14.

TABLE 13

Amounts of 70 wt % glycolic acid in water (GLA) or 1:4 dilution of 28-30 wt % ammonium hydroxide ($NH_4OH$) in water used to prepare reaction solutions of indicated pH.

| pH | Aqueous GLA (mL) | Aqueous $NH_4OH$ (mL) |
|---|---|---|
| 4.0 | 0.700 | 0 |
| 4.7 | 0.150 | 0 |
| 5.5 | 0 | 0 |
| 6.7 | 0 | 0.050 |
| 7.5 | 0 | 0.100 |

TABLE 14

Initial reaction rate for conversion of GLN to $NH_4GLA$ using immobilized *E. coli* MG1655/pSW138 cells expressing *A. facilis* 72W nitrilase at various pHs (average of duplicate reactions).

| pH | Initial Reaction Rate (mM GLA/h) |
|---|---|
| 4.0 | 0 |
| 4.7 | 68 |
| 5.5 | 347 |
| 6.7 | 354 |
| 7.5 | 351 |

EXAMPLE 32

Hydrolysis of Glycolonitrile to Ammonium Glycolate Using Immobilized *E. coli* FM5/pNM18 Expressing *A. facilis* 72W Nitrilase in the Presence or in the Absence of Hydrogen Cyanide (HCN)

A 50-mL jacketed reaction vessel equipped with overhead stirring and temperature control was charged with 4 g of GA/PEI-crosslinked carrageenan beads (prepared using the process described in Example 21), washed twice for 15 min with 72 mL of 0.1 M $NH_4GLA$ (pH 7.5)) containing 5% (dcw) *E. coli* FM5/pNM18 expressing the *A. facilis* 72W nitrilase (SEQ ID NO: 6). To the vessel was then added 10.9 g of distilled water and 3.0 mL 4.0 M $NH_4GLA$ (pH 7.5), and the reaction vessel was flushed with nitrogen. The mixture was stirred at 25° C. and an aliquot of 1.777 mL of 60.51 wt % glycolonitrile (GLN) in water (1.885 g, 20.0 mmol (Fluka, redistilled)) with or without 0.063 mL 50 wt % HCN in water (0.054 g, 1 mmol) was first added, followed immediately by addition of 0.320 mL of a 1:16 dilution of ammonium hydroxide (28-30 wt %) in water. Four 0.100-mL reaction samples were removed at predetermined times after the first GLN addition and analyzed by HPLC to determine the initial reaction rate. At completion of GLN conversion, the second aliquot each of GLN and ammonium hydroxide was added to maintain the concentration of GLN at ≦1 M and pH within a range of 7.0-7.5, and after the GLN conversion was completed, the third aliquot of each of GLN and ammonium hydroxide was added. At completion of the reaction, there was 100% conversion of GLN to produce glycolic acid (as the ammonium salt) in >99% yield, and the concentration of ammonium glycolate produced from added GLN was approximately 2.5 M (3.0 M total ammonium glycolate, including initial ammonium glycolate buffer, in a final reaction volume of ca. 23.7 mL).

At the end of the first reaction, the aqueous product mixture was decanted from the catalyst (under nitrogen), to the reaction vessel then added 13.9 mL of distilled, deionized water, and a second reaction was performed at 25° C. by the addition of aliquots of aqueous GLN and ammonium hydroxide as described immediately above. The initial reaction rates for consecutive batch reactions with catalyst recycle are listed in Table 15 (recycle reactions are reactions 2 through 9).

TABLE 15

Initial reaction rate for conversion of GLN to GLA in consecutive batch reactions with catalyst recycle using immobilized *E. coli* FM5/pNM18 expressing *A. facilis* 72W nitrilase in the presence and in the absence of HCN.

| Rxn # | HCN (mM GLA/h) | No additive (mM GLA/h) |
|---|---|---|
| 1 | 260 | 183 |
| 2 | 289 | 269 |
| 3 | 291 | 218 |
| 4 | 271 | 222 |
| 5 | 238 | 235 |
| 6 | 257 | 240 |
| 7 | 250 | 208 |
| 8 | 239 | 177 |
| 9 | 213 | 188 |

EXAMPLE 33

Affect of Addition of Either Formaldehyde or Hydrogen Cyanide in Consecutive Batch Reactions for Hydrolysis of Glycolonitrile to Ammonium Glycolate Using Immobilized *E. coli* FM5/pNM18 Expressing the *A. facilis* 72W Nitrilase The reactions were run, characterized, and the biocatalyst was recycled as described in Example 32 for reactions without addition of HCN, except that each aliquot of 1.777 mL of 60.51 wt % glycolonitrile (GLN) in water (1.885 g, 20.0 mmol (Fluka, redistilled)) contained either 0.074 mL 37 wt % HCHO in water (0.081 g, 1 mmol) (recycles 1, 2, 3, and 6) or 0.063 mL 50 wt % HCN in water (0.054 g, 1 mmol) (recycles 4, 5, and 7) (Table 16). The data for reactions without addition of HCHO or HCN are repeated from Table 15 for comparison.

Table 16. Initial reaction rate for conversion of GLN to GLA in consecutive batch reactions with catalyst recycle using immobilized *E. coli* FM5/pNM18 expressing *A. facilis* 72W nitrilase at addition of HCHO (reactions 1, 2, 3, and 6) or addition of HCN (reactions 4, 5, and 7) to the same reaction series, and without addition of HCHO or HCN.

TABLE 16

Initial reaction rate for conversion of GLN to GLA in consecutive batch reactions with catalyst recycle using immobilized *E. coli* FM5/pNM18 expressing *A. facilis* 72W nitrilase at addition of HCHO (reactions 1, 2, 3, and 6) or addition of HCN (reactions 4, 5, and 7) to the same reaction series, and without addition of HCHO or HCN.

| Reaction # | HCHO Initial rate (mM GLA/h) | HCN Initial rate (mM GLA/h) | No additives initial rate (mM GLA/h) |
|---|---|---|---|
| 1 | 192 | | 183 |
| 2 | 152 | | 269 |
| 3 | 90 | | 218 |
| 4 | | 234 | 222 |
| 5 | | 218 | 235 |
| 6 | 113 | | 240 |
| 7 | | 219 | 208 |
| 8 | | | 177 |
| 9 | | | 188 |

EXAMPLE 34

Hydrolysis of Glycolonitrile to Ammonium Glycolate Using *E. coli* FM5/pNM18-L201Q Cells Expressing *A. facilis* 72W Nitrilase Mutant L201Q A 50-mL centrifuge tube was charged with 1.25 mL uniform suspension obtained using 6 g of *E. coli* FM5/pNM18-L201Q expressing the *A. facilis* 72W nitrilase mutant L201Q (SEQ ID NO: 8) and 7.54 mL 0.35 M $Na_2HPO_4$ (pH 7.5), 35 mL 0.35 M Na2HPO$_4$ (pH 7.5) was added, the tube was centrifuged at 5000 rpm for 20 min, the supernatant was carefully and fully removed from cell paste, and 935 mg of the centrifuged cell paste was transferred to a 150-mL jacketed reaction vessel equipped with overhead stirring and temperature control. To the vessel was then added 52.54 mL of 0.3 M $NH_4$GLA (pH 7.5), 7.88 mL 4.0 M $NH_4$GLA (pH 7.5), and 9.63 mL of distilled water, and the reaction vessel was flushed with nitrogen. The mixture was stirred at 25° C., 7.82 mL of 54.61 wt % glycolonitrile (GLN) in water (8.18 g, 78.3 mmol (Fluka)) was added, and pH was adjusted to pH 7.5 by a 1:4 dilution of ammonium hydroxide (28-30 wt %) in water. To determine the initial reaction rates, four 0.050-mL reaction samples were removed at predetermined times after the first GLN addition, added to assay mix (0.025 mL of 6.0 N HCl and 0.800 mL 0.18 M n-propanol), vortexed, centrifuged at 12,000 rpm for 6 min, and supernate was analyzed by HPLC as described in Example 12. At completion of GLN conversion, the second aliquot of GLN was added, pH was adjusted to 7.5 with ammonium hydroxide, and after the GLN conversion was completed, the third GLN aliquot was added and pH was adjusted to pH 7.5. At completion of the reaction, there was 100% conversion of GLN to produce glycolic acid (as the ammonium salt) in >99% yield, and the concentration of ammonium glycolate produced from added GLN was approximately 2.5 M (2.9 M total ammonium glycolate, including initial ammonium glycolate buffer, in a final reaction volume of ca. 94.05 mL).

At the end of the first reaction, the aqueous product mixture was centrifuged from the cell pastes (5000 rpm, 20 min). The cell paste was weighed and transferred back to the reaction vessel. To the vessel then added 52.54 mL 0.3 M $NH_4$GLA (pH 7.5), 7.88 mL 4.0 M $NH_4$GLA (pH 7.5) and 9.63 mL of distilled water, the reaction vessel was flushed with nitrogen, and a second reaction was performed at 25° C. by the addition of aliquots of aqueous GLN and ammonium hydroxide as described immediately above. The weight of cell paste recovered after reaction 4 by centrifugation of reaction solution as described above was 964 mg.

The initial reaction rates for consecutive batch reactions with catalyst recycle are listed in Table 17 (recycle reactions are reactions 2 through 4).

TABLE 17

Initial reaction rate for conversion of GLN to GLA in consecutive batch reactions with catalyst recycle using *E. coli* FM5/pNM18-L201Q cell paste expressing *A. facilis* 72W nitrilase mutant L201Q.

| Reaction # | Initial Rate (mM GLA/h) |
|---|---|
| 1 | 180 |
| 2 | 157 |
| 3 | 147 |
| 4 | 133 |

EXAMPLE 35

Hydrolysis of Glycolonitrile to Ammonium Glycolate Using Immobilized *E. coli* MG1655/pSW138 Transformants Expressing *A. facilis* 72W Nitrilase or *A. facilis* 72W Nitrilase Mutants A 50-mL jacketed reaction vessel equipped with overhead stirring and temperature control was charged with 8 g of GA/PEI-crosslinked carrageenan beads (prepared using the process as described in Example 21), washed twice for 15 min with 72 mL of 0.1M $NH_4$GLA (pH 7.0)) containing 5% (dcw) *E. coli* MG1655/pSW138 transformant expressing the *A. facilis* 72W nitrilase (SEQ ID NO: 6), or the *A. facilis* 72W nitrilase mutants F168V (SEQ ID NO: 32), F168M (SEQ ID NO: 28), F168K (SEQ ID NO: 26), F168T (SEQ ID NO: 30), and L201Q (SEQ ID NO: 8). To the vessel was then added 14.632 g of distilled water and 6.0 mL 4.0 M $NH_4$GLA (pH 7.0), and the reaction vessel flushed with nitrogen. The mixture was stirred at 25° C. while programmable syringe pumps were used to add eight aliquots of 1.08 mL of 59 wt % glycolonitrile (GLN) in water (1.14 g, 12.0 mmol (Fluka, redistilled)) and 0.288 mL of a 1:16 dilution of ammonium hydroxide (28-30 wt %) in water (2.304 mL total); one aliquot each of GLN and ammonium hydroxide was added simultaneously every 2 h to maintain the concentration of GLN at ≦400 mM and the pH within a range of 6.5-7.5. Four 0.050-mL reaction samples were removed at predetermined times after the first GLN addition and analyzed by HPLC to determine the initial reaction rate. At completion of the reaction, there was 100% conversion of GLN to produce glycolic acid (as the ammonium salt) in >99% yield, and the concentration of ammonium glycolate produced from added GLN was approximately 2.4 M (3.0 M total ammonium glycolate, including initial ammonium glycolate buffer, in a final reaction volume of ca. 39.5 mL).

At the end of the first reaction, the aqueous product mixture was decanted from the catalyst (under nitrogen), leaving ca. 10.3 g of a mixture of immobilized cell catalyst (8.0 g) and remaining product mixture (ca. 2.3 g). To the reaction vessel then added 18.3 mL of distilled, deionized water, and a second reaction was performed at 25° C. by the addition of aliquots of aqueous GLN and ammonium hydroxide as described immediately above. The initial reaction rates for consecutive batch reactions with catalyst recycle are listed in Table 18 (recycle reactions are reactions 2 through 55).

The catalyst productivity (total grams GLA produced/gram dry cell weight (dcw) enzyme catalyst) was calculated for each nitrilase from the total number of consecutive batch reactions with catalyst recycle that resulted in 100% conversion of glycolonitrile. The catalyst productivity for each enzyme catalyst was: *E. coli* MG1655/pSW138-F168V, 1001 g GLA/g dcw (55 consecutive batch reactions); *E. coli* MG1655/pSW138-F168M, 473 g GLA/g dcw (26 consecutive batch reactions); *E. coli* MG1655/pSW138-F168K, 473 g GLA/g dcw (26 consecutive batch reactions); *E. coli* MG1655/pSW138-F168T, 364 g GLA/g dcw (20 consecutive batch reactions); *E. coli* MG1655/pSW138-L201Q, 346 g GLA/g dcw (19 consecutive batch reactions); *E. coli* MG1655/pSW138, 182 g GLA/g dcw (10 consecutive batch reactions).

TABLE 18

Initial reaction rates for conversion of GLN to GLA in consecutive batch reactions with catalyst recycle using immobilized *E. coli* MG1655/pSW138 transformants expressing *A. facilis* 72W nitrilase or *A. facilis* 72W nitrilase mutants

| Rxn # | MG1655/ pSW138- F168V (mM GLA/h) | MG1655/ pSW138- F168M (mM GLA/h) | MG1655/ pSW138- F168K (mM GLA/h) | MG1655/ pSW138- F168T (mM GLA/h) | MG1655/ pSW138- L201Q (mM GLA/h) | MG1655/ pSW138 (mM GLA/h) |
|---|---|---|---|---|---|---|
| 1 | 1050 | 658 | 652 | 423 | 757 | 330 |
| 2 | 698 | 538 | 560 | 389 | 611 | 220 |
| 3 | 719 | 488 | 394 | 453 | 497 | 207 |
| 4 | 654 | 452 | nd | 311 | 435 | 174 |
| 5 | 719 | 441 | 322 | 494 | 549 | 193 |
| 6 | 559 | 378 | 439 | 456 | 416 | 171 |
| 7 | 531 | 258 | 435 | 408 | 482 | 207 |
| 8 | 634 | 407 | 209 | 378 | 453 | 141 |
| 9 | 586 | 340 | 294 | 502 | 653 | 123 |
| 10 | 609 | 303 | 420 | 468 | 537 | 92 |
| 11 | 432 | 313 | 426 | 428 | 443 | 76 |
| 12 | 397 | 560 | 361 | 481 | 388 | |
| 13 | 318 | 430 | 422 | 391 | 359 | |
| 14 | 449 | 391 | 387 | 255 | 302 | |
| 15 | 259 | 304 | 444 | 260 | 246 | |
| 16 | 370 | 308 | 452 | 362 | 377 | |
| 17 | 401 | 330 | 448 | 318 | 307 | |
| 18 | 579 | 384 | nd | 299 | 252 | |
| 19 | 392 | 253 | nd | 233 | 282 | |
| 20 | nd | nd | 487 | 372 | 209 | |
| 21 | nd | nd | nd | nd | nd | |
| 22 | 356 | 247 | nd | 144 | 116 | |
| 23 | nd | nd | 355 | 165 | 129 | |
| 24 | nd | nd | 300 | | | |
| 25 | 402 | 219 | 252 | | | |
| 26 | 407 | 134 | 270 | | | |
| 27 | 390 | 87 | 141 | | | |
| 28 | 280 | 45 | | | | |
| 29 | 297 | 24 | | | | |
| 30 | 277 | | | | | |
| 31 | 300 | | | | | |

TABLE 18-continued

Initial reaction rates for conversion of GLN to GLA in consecutive batch reactions with catalyst recycle using immobilized *E. coli* MG1655/pSW138 transformants expressing *A. facilis* 72W nitrilase or *A. facilis* 72W nitrilase mutants

| Rxn # | MG1655/ pSW138- F168V (mM GLA/h) | MG1655/ pSW138- F168M (mM GLA/h) | MG1655/ pSW138- F168K (mM GLA/h) | MG1655/ pSW138- F168T (mM GLA/h) | MG1655/ pSW138- L201Q (mM GLA/h) | MG1655/ pSW138 (mM GLA/h) |
|---|---|---|---|---|---|---|
| 32 | 325 | | | | | |
| 33 | 344 | | | | | |
| 34 | 340 | | | | | |
| 35 | 317 | | | | | |
| 36 | 277 | | | | | |
| 37 | 191 | | | | | |
| 38 | 279 | | | | | |
| 39 | 325 | | | | | |
| 40 | 372 | | | | | |
| 41 | 257 | | | | | |
| 42 | 329 | | | | | |
| 43 | 530 | | | | | |
| 44 | 235 | | | | | |
| 45 | 291 | | | | | |
| 46 | 339 | | | | | |
| 47 | 226 | | | | | |
| 48 | 309 | | | | | |
| 49 | 406 | | | | | |
| 50 | 456 | | | | | |
| 51 | 242 | | | | | |
| 52 | 168 | | | | | |
| 53 | 217 | | | | | |
| 54 | 220 | | | | | |
| 55 | 59 | | | | | |

(nd = not determined).

EXAMPLE 36

Characterization of Ammonium Glycolate Obtained by Conversion of GLN Using Immobilized *E. coli* MG1655/pSW138 Transformant Expressing *A. facilis* 72W Nitrilase Mutant F168V To evaluate composition of product solutions obtained by GLN (Fluka, redistilled) hydrolysis with immobilized MG1655/pSW138-F168V biocatalyst (see Example 35, Table 18), the product solutions produced in reactions 5, 10, and 38 were characterized by HPLC and $^1$H NMR spectroscopy. Concentration of glycolate determined by HPLC was 3.1 M. Quantitative $^1$H NMR spectra were obtained using a Varian Unity Inova spectrometer (Varian, Inc., Palo Alto, Calif.) operating at 500 MHz. Samples were prepared by adding 150 μL of the reaction product along with 400 μL of $D_2O$ to a 5 mm NMR tube.

$^1$H NMR spectra were acquired using a spectral width of 6000 Hz with the transmitter located at 5 ppm, and a 90-degree pulse (5.9 microseconds at a transmitter power of 49 db). An acquisition time of 4 seconds was used which led to a total data size of 48,000 points. The longest $^1$H $T_1$ (8 sec) was associated with the methanol $CH_3$ protons, and the total delay time prior to acquisition was therefore set to 50 seconds (i.e., more than 5 times the methanol $CH_3$ $T_1$). This pre-delay time was split between a simple delay time ("d1") and a solvent saturation pulse of 30 seconds applied on resonance for residual water at a transmitter power of −6 db. Signal averaging of 32 scans was preceded by 4 steady-state ("dummy") scans to give a total experiment time of approximately 32 minutes. Assignments were obtained by comparison of $^1$H NMR chemical shifts with those obtained in previous 2-dimensional NMR correlation experiments, and by spiking experiments.

The impurities observed in the ammonium glycolate product solutions by $^1$H NMR spectroscopy were categorized, on the basis of their functional groups, into the following functional group categories: formaldehyde-derived, formic acid-derived, methanol-derived, and methyl-derived. Integrated peak areas of proton signals for each of the categories were assigned as follows: two protons were assigned to formaldehyde functionality, one proton assigned to formic acid functionality, three protons assigned to methanol functionality, and three protons assigned to methyl functionality. Integrated peak areas for ammonium glycolate were divided by 2 (the number of ammonium glycolate protons) and assigned a value of 100%. Integrated peak areas of the protons observed for each of the impurity functional group categories were divided by the number of corresponding protons (see above), and the resulting integrated peak area divided by the integrated peak area of one glycolate proton present in the sample to determine the percent concentration of the impurity relative to the concentration of ammonium glycolate present. The yield of ammonium glycolate (based on 100% conversion of GLN) and the % purity of ammonium glycolate (based on relative concentration of glycolate and total impurities) is listed in Table 19.

TABLE 19

Yield and purity of ammonium glycolate produced by the conversion of GLN using immobilized *E. coli* MG1655/pSW138 transformant expressing *A. facilis* 72W nitrilase mutant F168V.

| Reaction # | ammonium glycolate yield (%) | ammonium glycolate purity (%) |
|---|---|---|
| Example 26, reaction 5 | 99% | 98.5 |
| Example 26, reaction 10 | 99% | 98.5 |
| Example 26, reaction 38 | 99% | 98.8 |

EXAMPLE 37

Hydrolysis of Glycolonitrile Obtained from Hydrogen Cyanide and Formaldehyde to Ammonium Glycolate Using Immobilized *E. coli MG*1655/pSW138 Transformant Expressing *A. facilis* 72W Nitrilase Mutants F168V Glycolonitrile used for the reactions below was prepared as described in Examples 4-8, except the experimental set-up was modified to avoid the raising of the reaction flask and corresponding bath/stir plate assembly at the start of the HCHO feed into the reactor. The outlet of the heated section of the HCHO feed line was directly connected to an insulated 3-way ball valve which, in turn, could direct the HCHO feed through separate lines into either the reaction vessel or an external scintillation vial. At the beginning of the synthesis procedure, the HCHO feed was directed by the 3-way valve into the scintillation vial. Upon the apparent onset of 2-phase flow of the HCHO feed, the 3-way valve was turned to direct the HCHO feed into the reaction flask.

Biotransformation reactions were run as described in Example 35 except that the reaction volume was one half of the reactions in Example 35 and pH was maintained at pH 7.5. To a reaction vessel were added 4 g biocatalyst beads, 7.32 g of distilled water, and 3 mL 4.0 M $NH_4$GLA (pH 7.5), the vessel was flushed with nitrogen, the mixture was stirred at 25° C., and programmable syringe pumps were used to add eight aliquots of 0.54 mL of 60 wt. % glycolonitrile (GLN) in water (0.58 g, 6.0 mmol (GLN prepared as described above) and 0.15 mL of a 1:16 dilution of ammonium hydroxide (28-30 wt %) in water (1.2 mL total); one aliquot each of GLN and ammonium hydroxide was added simultaneously every 2 h. At the end of the first reaction, the aqueous product mixture was decanted from the catalyst (under nitrogen), 10.32 mL of deionized water was added, and a new biocatalyst recycle was started with addition of GLN and ammonium hydroxide as described immediately above. The initial reaction rates for consecutive batch reactions with catalyst recycle are listed in Table 20 (recycle reactions are reactions 2 through 24). For all reactions, the conversion of GLN to GLA was 100%, and the yield of GLA was greater than 99%.

TABLE 20

Initial reaction rates for conversion of GLN produced (as described in Example 37) to GLA in consecutive batch reactions with catalyst recycle using immobilized *E. coli* MG1655/pSW138 transformant expressing *A. facilis* 72W nitrilase mutant F168V (nd = not determined).

| Rxn # | Initial rate (mM GLA/h) |
|---|---|
| 1 | 1177 |
| 2 | 771 |
| 3 | 514 |
| 4 | 526 |
| 5 | nd |
| 6 | 425 |
| 7 | 440 |
| 8 | 386 |
| 9 | 434 |
| 10 | 329 |
| 11 | 469 |
| 12 | 396 |
| 13 | 358 |
| 14 | 318 |
| 15 | 387 |
| 16 | 365 |
| 17 | nd |
| 18 | 387 |

TABLE 20-continued

Initial reaction rates for conversion of GLN produced (as described in Example 37) to GLA in consecutive batch reactions with catalyst recycle using immobilized *E. coli* MG1655/pSW138 transformant expressing *A. facilis* 72W nitrilase mutant F168V (nd = not determined).

| Rxn # | Initial rate (mM GLA/h) |
|---|---|
| 19 | 415 |
| 20 | nd |
| 21 | nd |
| 22 | 370 |
| 23 | nd |
| 24 | 260 |

EXAMPLE 38

Isolation of Glycolic Acid from Ammonium Glycolate by Fixed-Bed Ion Exchange Chromatography GLN synthesized from hydrogen cyanide and formaldehyde as described in Examples 4-8 (synthesis of high purity GLN), was converted to ammonium glycolate as described in Example 22, without additives (except that the reaction volume was scaled-up 18-fold), and fixed-bed ion exchange was used to convert the ammonium glycolate product solution to glycolic acid.

A 5 cm ID×60 cm borosilicate glass column (Spectrum-Chromatography) fitted with Teflon® PTFE end caps and Dowex® G-26 strongly acidic cation resin in the $H^+$ form (Dow Chemical Co) were used. A 5-gallon polypropylene feed jug was used to supply ultrapure water (18+MΩ, produced by a Sybron-Barnstead Nanopure II unit) to the column feed pump (Cole-Parmer variable-speed diaphragm pump with all-Teflon® head) for resin pre- and post-rinsing. The jug was nitrogen-purged at all times to prevent absorption of atmospheric $CO_2$. After pre-rinsing the filled column (initial height=23", bed volume=1147 mL) with ultrapure water to an effluent of >5 MΩ, the ammonium glycolate (1.3 liters (1428 g), pH=7.09) was pumped through the bed upflow at 40 mL; when the glycolate was depleted, the unit was switched back to ultrapure water pumping at the same rate to continue pushing the feed material through the bed. During the run the column effluent was captured continuously in 50 mL increments using pre-rinsed HDPP (high density polypropylene) sample bottles; a total of thirty-eight 50-mL samples of effluent were taken continuously and were analyzed for pH (pH meter), glycolate concentration (HPLC), and ammonium ion content (via ion chromatography).

Determination of ammonium ion content was done using Dionex IP25 pump equipped with CD20 conductivity detector and Dionex CS17 column (3-11 mM Methane Sulfonic Acid, 1.0 mL/min, suppressed with a Dionex CSRS ultra set to 100 microamp, 1.0 mL/min, 100 microliters sample loop), and cation 3-11 mM CS17 method was applied for the analysis.

Fractions 12 to 23 were combined (600 mL total), stirred overnight with 5 g fresh Dowex® G-26 resin (pre-rinsed 3 times with 45 mL of deionized water for 20 min), 651 g of glycolic acid solution was collected by filtration. The solution was concentrated by rotary evaporation to produce 70 wt % glycolic acid (140 g product). Analysis of the 70 wt % glycolic acid for impurities indicated the purity of glycolic acid was greater than 99.9%.

EXAMPLE 39

Solvent Extraction Using Approximately 70% C8-C10 Trialkylamine in Combination with 10% Methyl Isobutyl Ketone and 20% Kerosene at 25° C.

Into a 4-mL glass reactor equipped with magnetic stir bar was placed 1 mL of a mixed solvent containing 70% (volume/volume) of trialkyl amine (Alamine® 336; Cognis Corp., Cincinnati, Ohio), 10% (volume/volume) methyl isobutyl ketone (MIBK) and 20% (volume/volume) kerosene. The pH of an aqueous solution of ammonium glycolate (5 wt % to 40 wt %) was adjusted to about pH 2 to 3 with concentrated sulfuric acid ($H_2SO_4$), then 1 mL of the resulting aqueous solution was added to the reactor. The resulting mixture was stirred for 30 minutes at 25° C. The stirring was stopped and the two phases allowed to separate, then the organic and aqueous phases were each sampled and analyzed for glycolic acid concentration by HPLC. For each initial glycolic acid concentration, Table 21 lists the final concentration of glycolic acid in each phase of the resulting mixture, and the partition coefficient calculated for each initial glycolic acid concentration.

TABLE 21

| Initial wt % glycolic acid in aqueous phase | Final wt % glycolic acid in aqueous phase | Final wt % glycolic acid in organic phase | Partition coefficient of glycolic acid (organic wt %/aqueous wt %) |
|---|---|---|---|
| 3.6 | 1.9 | 2.0 | 1.1 |
| 8.5 | 4.5 | 4.8 | 1.1 |
| 12.1 | 6.5 | 6.6 | 1.0 |
| 16.1 | 9.2 | 8.6 | 0.94 |
| 20.6 | 10.9 | 9.8 | 0.90 |
| 25.1 | 15.4 | 13.1 | 0.85 |
| 29.1 | 19.6 | 14.2 | 0.73 |
| 32.8 | 22.9 | 15.4 | 0.67 |

EXAMPLE 40

Solvent Extraction Using Approximately 70% C8-C10 Trialkylamine in Combination with 10% Methyl Isobutyl Ketone and 20% Kerosene at 50° C.

Into a 4-mL glass reactor equipped with magnetic stir bar was placed 1 mL of a mixed solvent containing 70% (volume/volume) Alamine® 336 (Cognis), 10% (volume/volume) methyl isobutyl ketone (MIBK) and 20% (volume/volume) kerosene. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 50° C. The stirring was stopped and the two phases allowed to separate, then the organic and aqueous phases were each sampled and analyzed for glycolic acid concentration by HPLC. For each initial glycolic acid concentration, Table 22 lists the final concentration of glycolic acid in each phase of the resulting mixture, and the partition coefficient for each initial glycolic acid concentration.

TABLE 22

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 3.4 | 1.1 | 0.32 |
| 8.5 | 6.3 | 4.1 | 0.66 |
| 12.1 | 8.2 | 5.2 | 0.63 |
| 16.1 | 10.5 | 7.7 | 0.74 |
| 20.6 | 13.2 | 9.0 | 0.69 |
| 25.1 | 16.5 | 13.8 | 0.83 |
| 29.1 | 19.8 | 13.4 | 0.68 |
| 32.8 | 23.5 | 14.4 | 0.61 |

EXAMPLE 41

Solvent Extraction Using Approximately 70% C8-C10 Trialkylamine in Combination with 10% Methyl Isobutyl Ketone and 20% Kerosene at 75° C.

Into a 4-mL glass reactor equipped with magnetic stir bar was placed 1 mL of a mixed solvent containing 70% (volume/volume) Alamine® 336 (Cognis), 10% (volume/volume) methyl isobutyl ketone (MIBK) and 20% (volume/volume) kerosene. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 75° C. The stirring was stopped and the two phases allowed to separate, then the organic and aqueous phases were each sampled and analyzed for glycolic acid concentration by HPLC. For each initial glycolic acid concentration, Table 23 lists the final concentration of glycolic acid in each phase of the resulting mixture, and the partition coefficient for each initial glycolic acid concentration.

TABLE 23

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 3.9 | 0.6 | 0.16 |
| 8.5 | 7.6 | 1.7 | 0.22 |
| 12.1 | 9.8 | 3.4 | 0.35 |
| 16.1 | 12.6 | 5.0 | 0.40 |
| 20.6 | 15.5 | 7.5 | 0.49 |
| 25.1 | 18.3 | 10.2 | 0.56 |
| 29.1 | 22.7 | 12.3 | 0.54 |
| 32.8 | 26.3 | 13.7 | 0.52 |

EXAMPLE 42

Solvent Extraction Using Approximately 90% C8-C10 Trialkylamine in Combination with 10% Methyl Isobutyl Ketone at 25° C.

Into a 4-mL glass reactor equipped with magnetic stir bar was placed 1 mL of a mixed solvent containing 90% (volume/volume) Alamine® 336 (Cognis) and 10% (volume/volume) methyl isobutyl ketone (MIBK). The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 25° C. The stirring was stopped and the two phases allowed to separate, then the organic and aqueous phases were each sampled and analyzed for glycolic acid concentration by HPLC. For each initial glycolic acid concentration, Table 24 lists the final concentration of glycolic acid in each phase of the resulting mixture, and the partition coefficient for each initial glycolic acid concentration.

TABLE 24

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 1.8 | 3.6 | 1.98 |
| 8.5 | 4.3 | 6.8 | 1.57 |
| 12.1 | 5.9 | 8.1 | 1.38 |
| 16.1 | 8.4 | 12.2 | 1.44 |
| 20.6 | 12.6 | 14.2 | 1.13 |
| 25.1 | 13.6 | 16.2 | 1.19 |
| 29.1 | 16.6 | 18.9 | 1.14 |
| 32.8 | 21.1 | 19.4 | 0.92 |

EXAMPLE 43

Solvent Extraction Using Approximately 90% C8-C10 Trialkylamine in Combination with 10% Methyl Isobutyl Ketone at 75° C.

Into a 4-mL glass reactor equipped with magnetic stir bar was placed 1 mL of a mixed solvent containing 90% (volume/volume) Alamine® 336 (Cognis) and 10% (volume/volume) methyl isobutyl ketone (MIBK). The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 75° C. The stirring was stopped and the two phases allowed to separate, then the organic and aqueous phases were each sampled and analyzed for glycolic acid concentration by HPLC. For each initial glycolic acid concentration, Table 25 lists the final concentration of glycolic acid in each phase of the resulting mixture, and the partition coefficient for each initial glycolic acid concentration.

TABLE 25

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 2.4 | 1.8 | 0.75 |
| 8.5 | 5.6 | 4.0 | 0.70 |
| 12.1 | 7.7 | 5.8 | 0.76 |
| 16.1 | 10.9 | 7.9 | 0.73 |
| 20.6 | 12.8 | 10.0 | 0.79 |
| 25.1 | 16.0 | 13.8 | 0.87 |
| 29.1 | 18.4 | 15.5 | 0.84 |
| 32.8 | 21.7 | 18.6 | 0.86 |

EXAMPLE 44

Solvent Extraction Using Approximately 50% C8-C10 Trialkylamine in Combination with 10% Methyl Isobutyl Ketone and 40% Kerosene at 25° C.

Into a 4-mL glass reactor equipped with magnetic stir bar was placed 1 mL of a mixed solvent containing 50% (volume/volume) Alamine® 336 (Cognis), 10% (volume/volume) methyl isobutyl ketone (MIBK) and 40% (volume/volume) kerosene. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 25° C. The stirring was stopped and the two phases allowed to separate, then the organic and aqueous phases were each sampled and analyzed for glycolic acid concentration by HPLC. For each initial glycolic acid concentration, Table 26 lists the final concentration of glycolic acid in each phase of the resulting mixture, and the partition coefficient for each initial glycolic acid concentration.

TABLE 26

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 2.2 | 1.6 | 0.76 |
| 8.5 | 5.2 | 3.7 | 0.71 |
| 12.1 | 7.7 | 5.6 | 0.72 |
| 16.1 | 11.0 | 7.1 | 0.65 |
| 20.6 | 13.8 | 8.1 | 0.59 |
| 25.1 | 18.5 | 9.4 | 0.51 |
| 29.1 | 21.9 | 10.5 | 0.48 |
| 32.8 | 26.1 | 12.1 | 0.46 |

EXAMPLE 45

Solvent Extraction Using Approximately 50% C8-C10 Trialkylamine in Combination with 10% Methyl Isobutyl Ketone and 40% Kerosene at 75° C.

Into a 4-mL glass reactor equipped with magnetic stir bar was placed 1 mL of a mixed solvent containing 50% (volume/volume) Alamine® 336 (Cognis), 10% (volume/volume) methyl isobutyl ketone (MIBK) and 40% (volume/volume) kerosene. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 75° C. The stirring was stopped and the two phases allowed to separate, then the organic and aqueous phases were each sampled and analyzed for glycolic acid concentration by HPLC. For each initial glycolic acid concentration, Table 27 lists the final concentration of glycolic acid in each phase of the resulting mixture, and the partition coefficient for each initial glycolic acid concentration.

TABLE 27

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 2.7 | 1.0 | 0.38 |
| 8.5 | 6.6 | 2.1 | 0.32 |
| 12.1 | 9.4 | 3.3 | 0.35 |
| 16.1 | 13.5 | 3.8 | 0.28 |
| 20.6 | 16.2 | 5.4 | 0.33 |
| 25.1 | 20.1 | 7.0 | 0.35 |
| 29.1 | 23.9 | 8.3 | 0.35 |
| 32.8 | 27.4 | 9.5 | 0.35 |

EXAMPLE 46

Solvent Extraction Using Approximately 90% C8-C10 Trialkylamine in Combination with 10% 1-Octanol at 25° C.

Into a 4-mL glass reactor equipped with magnetic stir bar was placed 1 mL of a mixed solvent containing 90% (volume/ volume) Alamine® 336 (Cognis), 10% (volume/volume) 1-octanol. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 25° C. The stirring was stopped and the two phases allowed to separate, then the organic and aqueous phases were each sampled and analyzed for glycolic acid concentration by HPLC. For each initial glycolic acid concentration, Table 28 lists the final concentration of glycolic acid in each phase of the resulting mixture, and the partition coefficient for each initial glycolic acid concentration.

TABLE 28

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 1.9 | 2.0 | 1.09 |
| 8.5 | 4.4 | 4.6 | 1.03 |
| 12.1 | 5.8 | 7.5 | 1.30 |
| 16.1 | 8.5 | 10.2 | 1.20 |
| 20.6 | 10.4 | 12.4 | 1.20 |
| 25.1 | 13.8 | 15.2 | 1.10 |
| 29.1 | 17.2 | 16.9 | 0.99 |
| 32.8 | 21.7 | 17.7 | 0.82 |

EXAMPLE 47

Solvent Extraction Using Approximately 90% C8-C10 Trialkylamine in Combination with 10% 1-Octanol at 75° C.

Into a 4-mL glass reactor equipped with magnetic stir bar was placed 1 mL of a mixed solvent containing 90% (volume/volume) Alamine® 336 (Cognis), 10% (volume/volume) 1-octanol. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 75° C. The stirring was stopped and the two phases allowed to separate, then the organic and aqueous phases were each sampled and analyzed for glycolic acid concentration by HPLC. For each initial glycolic acid concentration, Table 29 lists the final concentration of glycolic acid in each phase of the resulting mixture, and the partition coefficient for each initial glycolic acid concentration.

TABLE 29

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 2.5 | 1.4 | 0.54 |
| 8.5 | 15.9 | 3.3 | 0.56 |
| 12.1 | 8.4 | 5.2 | 0.62 |
| 16.1 | 11.3 | 7.2 | 0.63 |
| 20.6 | 13.3 | 9.7 | 0.73 |
| 25.1 | 16.8 | 12.6 | 0.75 |
| 29.1 | 19.5 | 14.2 | 0.73 |
| 32.8 | 22.8 | 16.1 | 0.70 |

EXAMPLE 48

Solvent Extraction Using Approximately 70% C8-C10 Trialkylamine in Combination with 30% 1-Octanol at 25° C.

Into a 4-mL glass reactor equipped with magnetic stir bar was placed 1 mL of a mixed solvent containing 70% (volume/volume) Alamine® 336 (Cognis), 30% (volume/volume) 1-octanol. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 25° C. The stirring was stopped and the two phases allowed to separate, then the organic and aqueous phases were each sampled and analyzed for glycolic acid concentration by HPLC. For each initial glycolic acid concentration, Table 30 lists the final concentration of glycolic acid in each phase of the resulting mixture, and the partition coefficient for each initial glycolic acid concentration.

TABLE 30

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 1.8 | 2.0 | 1.10 |
| 8.5 | 4.5 | 4.5 | 1.01 |
| 12.1 | 6.8 | 7.0 | 1.02 |
| 16.1 | 9.7 | 8.7 | 0.90 |
| 20.6 | 12.8 | 9.8 | 0.76 |
| 25.1 | 16.9 | 11.2 | 0.67 |
| 29.1 | 20.7 | 12.3 | 0.60 |
| 32.8 | 24.9 | 13.4 | 0.54 |

EXAMPLE 49

Solvent Extraction Using Approximately 70% C8-C10 Trialkylamine in Combination with 30% 1-Octanol at 75° C.

Into a 4-mL glass reactor equipped with magnetic stir bar was placed 1 mL of a mixed solvent containing 70% (volume/volume) Alamine® 336 (Cognis), 30% (volume/volume) 1-octanol. The pH of an aqueous solution of ammonium giycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 75° C. The stirring was stopped and the two phases allowed to separate, then the organic and aqueous phases were each sampled and analyzed for glycolic acid concentration by HPLC. For each initial glycolic acid concentration, Table 31 lists the final concentration of glycolic acid in each phase of the resulting mixture, and the partition coefficient for each initial glycolic acid concentration.

TABLE 31

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 2.3 | 1.6 | 0.69 |
| 8.5 | 5.5 | 4.1 | 0.74 |
| 12.1 | 8.5 | 5.4 | 0.64 |
| 16.1 | 11.0 | 7.5 | 0.68 |
| 20.6 | 14.0 | 8.6 | 0.62 |
| 25.1 | 18.2 | 11.1 | 0.61 |
| 29.1 | 24.1 | 12.0 | 0.50 |
| 32.8 | 25.5 | 13.4 | 0.52 |

EXAMPLE 50

Solvent Extraction Using Approximately 90% C8-C10 Trialkylamine in Combination with 10% Toluene at 25° C.

Into a 4-mL glass reactor equipped with magnetic stir bar was placed 1 mL of a mixed solvent containing 90% (volume/volume) Alamine® 336 (Cognis), 10% (volume/volume) toluene. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 25° C. The stirring was stopped and the two phases allowed to separate, then the organic and aqueous phases were each sampled and analyzed for glycolic acid concentration by HPLC. For each initial glycolic acid concentration, Table 32 lists the final concentration of glycolic acid in each phase of the resulting mixture, and the partition coefficient for each initial glycolic acid concentration.

TABLE 32

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 1.9 | 2.4 | 1.22 |
| 8.5 | 4.6 | 6.5 | 1.41 |
| 12.1 | 6.0 | 8.9 | 1.46 |
| 16.1 | 8.8 | 10.8 | 1.23 |
| 20.6 | 11.0 | 13.2 | 1.20 |
| 25.1 | 14.4 | 18.2 | 1.26 |
| 29.1 | 17.7 | 17.8 | 1.00 |
| 32.8 | 23.0 | 19.8 | 0.86 |

EXAMPLE 51

Solvent Extraction Using Approximately 90% C8-C10 Trialkylamine in Combination with 10% Toluene at 75° C.

Into a 4-mL glass reactor equipped with magnetic stir bar was placed 1 mL of a mixed solvent containing 90% (volume/volume) Alamine® 336 (Cognis), 10% (volume/volume) toluene. The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 75° C. The stirring was stopped and the two phases allowed to separate, then the organic and aqueous phases were each sampled and analyzed for glycolic acid concentration by HPLC. For each initial glycolic acid concentration, Table 33 lists the final concentration of glycolic acid in each phase of the resulting mixture, and the partition coefficient for each initial glycolic acid concentration.

TABLE 33

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 2.6 | 1.3 | 0.51 |
| 8.5 | 6.0 | 3.5 | 0.58 |
| 12.1 | 8.3 | 5.5 | 0.67 |
| 16.1 | 11.9 | 7.5 | 0.63 |
| 20.6 | 13.8 | 9.0 | 0.65 |
| 25.1 | 16.4 | 12.0 | 0.73 |
| 29.1 | 19.3 | 14.5 | 0.75 |
| 32.8 | 22.0 | 16.6 | 0.75 |

EXAMPLE 52

Solvent Extraction Using Approximately 90% C8-C10 Trialkylamine in Combination with 10% Xylenes at 25° C.

Into a 4-mL glass reactor equipped with magnetic stir bar was placed 1 mL of a mixed solvent containing 90% (volume/volume) Alamine® 336 (Cognis), 10% (volume/volume) xylenes (mixed xylene isomers). The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 25° C. The stirring was stopped and the two phases allowed to separate, then the organic and aqueous phases were each sampled and analyzed for glycolic acid concentration by HPLC. For each initial glycolic acid concentration, Table 34 lists the final concentration of glycolic acid in each phase of the resulting mixture, and the partition coefficient for each initial glycolic acid concentration.

TABLE 34

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 1.9 | 2.5 | 1.31 |
| 8.5 | 4.4 | 6.1 | 1.39 |
| 12.1 | 5.7 | 8.0 | 1.40 |
| 16.1 | 8.2 | 10.3 | 1.25 |
| 20.6 | 10.1 | 12.8 | 1.27 |
| 25.1 | 15.1 | 15.1 | 1.00 |
| 29.1 | 16.2 | 22.7 | 1.40 |
| 32.8 | 20.5 | 18.6 | 0.91 |

EXAMPLE 53

Solvent Extraction Using Approximately 90% C8-C10 Trialkylamine in Combination with 10% Xylenes at 75° C.

Into a 4-mL glass reactor equipped with magnetic stir bar was placed 1 mL of a mixed solvent containing 90% (volume/volume) Alamine® 336 (Cognis), 10% (volume/volume) xylenes (mixed xylene isomers). The pH of an aqueous solution of ammonium glycolate (5 wt % to 40 wt %) was adjusted to pH 2 to 3 with concentrated sulfuric acid, then 1 mL of the resulting aqueous solution was added to the reactor. The resulting mixture was stirred for 30 minutes at 75° C. The stirring was stopped and the two phases allowed to separate, then the organic and aqueous phases were each sampled and analyzed for glycolic acid concentration by HPLC. For each initial glycolic acid concentration, Table 35 lists the final concentration of glycolic acid in each phase of the resulting mixture, and the partition coefficient for each initial glycolic acid concentration.

TABLE 35

| Initial wt % glycolic acid in aqueous phase | Final wt % glycolic acid in aqueous phase | Final wt % glycolic acid in organic phase | Partition coefficient (wt % org./wt % aq.) |
|---|---|---|---|
| 3.6 | 2.6 | 1.4 | 0.55 |
| 8.5 | 6.0 | 3.3 | 0.55 |
| 12.1 | 8.4 | 5.6 | 0.66 |
| 16.1 | 11.6 | 7.4 | 0.64 |
| 20.6 | 14.0 | 9.1 | 0.65 |
| 25.1 | 16.4 | 12.0 | 0.73 |
| 29.1 | 19.2 | 14.4 | 0.75 |
| 32.8 | 22.5 | 16.1 | 0.72 |

EXAMPLE 54

Back Extraction Using Water from a Loaded Solvent of Approximately 70% C8-C10 Trialkylamine in Combination with 10% Methyl Isobutyl Ketone and 20% Kerosene Following the procedures in Example 1, into a 1-L cylindrical glass vessel on an extraction mixer (mix by rotating back and forth vertically) was placed 100 mL of a mixed solvent containing 70% (volume/volume) Alamine® 336 (Cognis), 10% (volume/volume) methyl isobutyl ketone (MIBK) and 20% (volume/volume) kerosene. The pH of an aqueous solution of ammonium glycolate (10 wt % to 50 wt %) was adjusted to approximately pH 2 to 3 with concentrated sulfuric acid, then 100 mL of the resulting aqueous solution was added to the extraction mixer. The resulting mixture was stirred for 60 minutes at room temperature. The mixing was stopped and the two phases allowed to separate, then the organic and aqueous phases were each sampled and analyzed for glycolic acid concentration by HPLC. The organic phase was collected and used in the back extraction. This organic phase containing glycolic acid is referred as "loaded solvent" below.

Into a 85-mL pressure reaction glass tube (pressure reaction vessel, from Andrews Glass Co.) equipped with magnetic stir bar and double dip tubes was placed 10 mL deionized water and 10 mL of the loaded solvent. The vessel was then closed, and the headspace purged with nitrogen. The resulting mixture was stirred for 60 minutes at 120° C. under 40 psig (~275.8 kPa) nitrogen. The stirring was stopped and the two phases allowed to separate at 120° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent, Table 36 lists the final concentration of glycolic acid in each phase of the resulting mixture, and the partition coefficient for each initial glycolic acid concentration.

TABLE 36

| Initial wt % glycolic acid in loaded solvent | Final wt % glycolic acid in aqueous phase | Final wt % glycolic acid in organic phase | Partition coefficient (wt % org./wt % aq.) |
|---|---|---|---|
| 3.9 | 1.7 | 0.82 | 0.47 |
| 11.3 | 6.5 | 3.4 | 0.53 |
| 16.0 | 9.0 | 4.6 | 0.51 |
| 17.5 | 9.8 | 5.1 | 0.52 |

EXAMPLE 55

Back Extraction from a Loaded Solvent of Approximately 70% C8-C10 Trialkylamine in Combination with 10% Methyl Isobutyl Ketone and 20% Kerosene Into a 85-mL pressure reaction glass tube (pressure reaction vessel, from Andrews Glass Co.) equipped with magnetic stir bar and double dip tubes was placed 10 mL aqueous solution of glycolic acid (20 wt % or 40 wt %) and 10 mL of the loaded solvent (see Example 54). The vessel was then closed, and the headspace purged with nitrogen. The resulting mixture was stirred for 60 minutes at 120° C. under 40 psig (~275.8 kPa) nitrogen. The stirring was stopped and the two phases allowed to separate at 120° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent and aqueous solution, Table 37 lists the final concentration of glycolic acid in each phase of the resulting mixture, and the partition coefficient for each initial glycolic acid concentration.

TABLE 37

| Initial wt % glycolic acid in aqueous phase | Initial wt % glycolic acid in loaded solvent | Final wt % glycolic acid in aqueous phase | Final wt % glycolic acid in organic phase | Partition coefficient (wt % org./wt % aq.) |
|---|---|---|---|---|
| 20.0 | 16.0 | 20.7 | 12.1 | 0.59 |
| 40.0 | 17.5 | 33.7 | 17.3 | 0.51 |

EXAMPLE 56

Back Extraction Using Water from a Loaded Solvent of Approximately 70% C8-C10 Trialkylamine in Combination with 10% Methyl Isobutyl Ketone and 20% Kerosene Into a 85-mL pressure reaction glass tube (pressure reaction vessel, from Andrews Glass Co.) equipped with magnetic stir bar and double dip tubes was placed 10 mL deionized water and 10 mL of the loaded solvent (see Example 54). The vessel was then closed, and the headspace purged with nitrogen. The resulting mixture was stirred for 60 minutes at 140° C. under 40 psig (~275.8 kPa) nitrogen. The stirring was stopped and the two phases allowed to separate at 140° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent, Table 38 lists the final concentration of glycolic acid in each phase of the resulting mixture, and the partition coefficient for each initial glycolic acid concentration.

TABLE 38

| Initial wt % glycolic acid in loaded solvent | Final wt % glycolic acid in aqueous phase | Final wt % glycolic acid in organic phase | Partition coefficient (wt % org./wt % aq.) |
|---|---|---|---|
| 3.9 | 2.8 | 1.35 | 0.48 |
| 11.3 | 6.2 | 2.3 | 0.37 |
| 16.0 | 9.4 | 3.2 | 0.34 |
| 17.5 | 10.2 | 3.6 | 0.35 |

EXAMPLE 57

Back Extraction from a Loaded Solvent of Approximately 70% C8-C10 Trialkylamine in Combination with 10% Methyl Isobutyl Ketone and 20% Kerosene Into a 85-mL pressure reaction glass tube (pressure reaction vessel, from Andrews Glass Co.) equipped with magnetic stir bar and double dip tubes was placed 10 mL aqueous solution of glycolic acid (20 wt % or 40 wt %) and 10 mL of the loaded solvent (see Example 54). The vessel was then closed, and the headspace purged with nitrogen. The resulting mixture was stirred for 60 minutes at 140° C. under 40 psig (~275.8 kPa) nitrogen. The stirring was stopped and the two phases allowed to separate at 140° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent and aqueous solution, Table 39 lists the final concentration of glycolic acid in each phase of the resulting mixture, and the partition coefficient for each initial glycolic acid concentration.

TABLE 39

| Initial wt % glycolic acid in aqueous phase | Initial wt % glycolic acid in loaded solvent | Final wt % glycolic acid in aqueous phase | Final wt % glycolic acid in organic phase | Partition coefficient (wt % org./wt % aq.) |
|---|---|---|---|---|
| 20.0 | 16.0 | 21.9 | 11.7 | 0.54 |
| 40.0 | 17.5 | 34.4 | 18.7 | 0.54 |

EXAMPLE 58

Back Extraction Using Water from a Loaded Solvent of Approximately 70% C8-C10 Trialkylamine in Combination with 30% Toluene Into a 85-mL pressure reaction glass tube (pressure reaction vessel, from Andrews Glass Co.) equipped with magnetic stir bar and double dip tubes was placed 10 mL deionized water and 10 mL of the loaded solvent (see Example 54). The vessel was then closed, and the headspace purged with nitrogen. The resulting mixture was stirred for 60 minutes at 120° C. under 40 psig (~275.8 kPa) nitrogen. The stirring was stopped and the two phases allowed to separate at 120° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent, Table 40 lists the final concentration of glycolic acid in each phase of the resulting mixture, and the partition coefficient for each initial glycolic acid concentration.

TABLE 40

| Initial wt % glycolic acid in loaded solvent | Final wt % glycolic acid in aqueous phase | Final wt % glycolic acid in organic phase | Partition coefficient (wt % org./wt % aq.) |
|---|---|---|---|
| 3.7 | 2.6 | 0.75 | 0.28 |
| 10.7 | 6.7 | 2.9 | 0.42 |
| 14.2 | 8.5 | 4.4 | 0.52 |
| 15.7 | 10.0 | 3.8 | 0.38 |

EXAMPLE 59

Back Extraction from a Loaded Solvent of Approximately 70% C8-C10 Trialkylamine in Combination with 30% Toluene Into a 85-mL pressure reaction glass tube (pressure reaction vessel, from Andrews Glass Co.) equipped with magnetic stir bar and double dip tubes was placed 10 mL aqueous solution of glycolic acid (20 wt % or 40 wt %) and 10 mL of the loaded solvent (see Example 54). The vessel was then closed, and the headspace purged with nitrogen. The resulting mixture was stirred for 60 minutes at 120° C. under 40 psig (~275.8 kPa) nitrogen. The stirring was stopped and the two phases allowed to separate at 120° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent and aqueous solution, Table 41 lists the final concentration of glycolic acid in each phase of the resulting mixture, and the partition coefficient for each initial glycolic acid concentration.

TABLE 41

| Initial wt % glycolic acid in aqueous phase | Initial wt % glycolic acid in loaded solvent | Final wt % glycolic acid in aqueous phase | Final wt % glycolic acid in organic phase | Partition coefficient (wt % org./wt % aq.) |
|---|---|---|---|---|
| 20.0 | 14.2 | 21.9 | 11.7 | 0.54 |
| 40.0 | 15.7 | 34.4 | 18.7 | 0.54 |

EXAMPLE 60

Back Extraction Using Water from a Loaded Solvent of Approximately 70% C8-C10 Trialkylamine in Combination with 30% Toluene Into a 85-mL pressure reaction glass tube (pressure reaction vessel, from Andrews Glass Co.) equipped with magnetic stir bar and double dip tubes was placed 10 mL deionized water and 10 mL of the loaded solvent (see Example 54). The vessel was then closed, and the headspace purged with nitrogen. The resulting mixture was stirred for 60 minutes at 140° C. under 40 psig (~275.8 kPa) nitrogen. The stirring was stopped and the two phases allowed to separate at 140° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent, Table 42 lists the final concentration of glycolic acid in each phase of the resulting mixture, and the partition coefficient for each initial glycolic acid concentration.

TABLE 42

| Initial wt % glycolic acid in loaded solvent | Final wt % glycolic acid in aqueous phase | Final wt % glycolic acid in organic phase | Partition coefficient (wt % org./wt % aq.) |
|---|---|---|---|
| 3.7 | 2.7 | 0.70 | 0.26 |
| 10.7 | 7.6 | 2.3 | 0.30 |
| 14.2 | 9.5 | 3.6 | 0.38 |
| 15.7 | 10.1 | 2.8 | 0.28 |

EXAMPLE 61

Back Extraction from a Loaded Solvent of Approximately 70% C8-C10 Trialkylamine in Combination with 30% Toluene Into a 85-mL pressure reaction glass tube (pressure reaction vessel, from Andrews Glass Co.) equipped with magnetic stir bar and double dip tubes was placed 10 mL aqueous solution of glycolic acid (20 wt % or 40 wt %) and 10 mL of the loaded solvent (see Example 54). The vessel was then closed, and the headspace purged with nitrogen. The resulting mixture was stirred for 60 minutes at 140° C. under 40 psig (~275.8 kPa) nitrogen. The stirring was stopped and the two phases allowed to separate at 140° C., then the organic phase was sampled under pressure through the top dip tube into a Hoke cylinder, and aqueous phases was sampled under pressure through the bottom dip tube into another Hoke cylinder. Both phases were analyzed for glycolic acid concentration by HPLC.

For each initial glycolic acid concentration in the loaded solvent and aqueous solution, Table 43 lists the final concentration of glycolic acid in each phase of the resulting mixture, and the partition coefficient for each initial glycolic acid concentration.

TABLE 43

| Initial wt % glycolic acid in aqueous phase | Initial wt % glycolic acid in loaded solvent | Final wt % glycolic acid in aqueous phase | Final wt % glycolic acid in organic phase | Partition coefficient (wt % org./wt % aq.) |
|---|---|---|---|---|
| 20.0 | 14.2 | 23.2 | 10.2 | 0.44 |
| 40.0 | 15.7 | 37.4 | 16.9 | 0.45 |

EXAMPLE 62

Thermal Decomposition of Molten Ammonium Glycolate Salt Heated Up to ~133° C. for 3.5 Hours Approximately 54.65 g of 25 wt % ammonium glycolate solution was added to a 100-mL 3-neck flask, and water was removed by distillation. When the weight of liquid in the flask decreased to 13.63 g, the clear, viscous liquid was analyzed: 12% (mol/mol) of ammonium glycolate was converted to glycolamide, and 13% (mol/mol) of ammonium glycolate was converted to glycolic dimer (as combined glycolic acid dimer and ammonium glycolate dimer); glycolic acid (as combined glycolic acid and ammonium glycolate) and ammonium recovery were 70% (mol/mol) and 73% (mol/mol) respectively (yields calculated based on final molarity of products relative to final total molarity of ammonium glycolate and products). After a sample was removed for analysis by HPLC, Ion Electrode, GC, etc. (referred to as "sampling" from here on), 12.06 g of clear, viscous liquid remained in the flask. A vacuum of 254 mm Hg was imposed, and heating continued up to 133° C. over a period of 3.5 hours. Analysis of the resulting product showed 24% (mol/mol) conversion of starting ammonium glycolate to glycolamide, 32% (mol/mol) conversion of starting ammonium glycolate to glycolic dimer (as combined glycolic acid dimer and ammonium glycolate dimer), 20% (mol/mol) glycolic acid recovery (as, combined glycolic acid and ammonium glycolate) and 27% (mol/mol) of ammonium ion remaining. The combined yield of glycolic acid and glycolic acid dimer (separate from the ammonium glycolate and ammonium glycolate dimer present) was calculated to be at least approximately 9%.

EXAMPLE 63

Thermal Decomposition of Molten Ammonium Glycolate Salt Heated up to ~140-150° C. for Approximately 6 Hours Followed by Hydrolysis of Glycolic Acid Oligomers Approximately 54.82 g of 25 wt % ammonium glycolate solution was added to a 100-mL 3-neck flask, and water was removed by distillation. When the weight of liquid in the flask decreased 21.15 g, about 8 (mol/mol)% ammonia had been removed. After sampling, 19.91 g of clear, viscous liquid was left in the flask. A vacuum up to 74 mm Hg was imposed, and the temperature was raised to 140-150° C. within five hours and maintained for about an hour. The weight of residual liquid in the flask was 10.33 g. Analysis of this product indicated 24% (mol/mol) of ammonium glycolate was converted to glycolamide, 28% (mol/mol) of ammonium glycolate was converted to glycolic dimer (as combined glycolic acid dimer and ammonium glycolate dimer); glycolic acid (as combined glycolic acid and ammonium glycolate) and ammonium recovery were 20% and 11% (mol/mol), respectively. Approximately 7000 ppm of glycolide was also produced. After sampling, 9 g of the liquid was mixed with 9 g of water. The resulting solution was heated to about 105° C. and refluxed for two hours. No further reduction in ammonium ion was observed, and dimer and oligomer were converted to glycolic acid. Glycolamide concentration did not change significantly. Yield of glycolic acid dimer (as combined glycolic acid dimer and ammonium glycolate dimer) dropped from 24% (mol/mol) to 4% (mol/mol). Final glycolic acid recovery (as combined glycolic acid and ammonium glycolate) was 56% (mol/mol). Yield of glycolic acid was at least 45%.

EXAMPLE 64

Thermal Decomposition of Molten Ammonium Glycolate Salt Heated to ~140-150° C. for Approximately 1 Hour Followed by Heating at 170° C.

Approximately 54.85 g of 25 wt % ammonium glycolate solution was added to a 100-mL 3-neck flask, and water was removed by distillation under vacuum (633 to 379 mm-Hg). When the weight of liquid in the flask decreased to 13.33 g, 10% (mol/mol) of ammonium glycolate was converted to glycolamide, and 13% (mol/mol) of ammonium glycolate was converted to glycolic dimer (as combined glycolic acid dimer and ammonium glycolate dimer); glycolic acid (as combined glycolic acid and ammonium glycolate) and ammonium recovery were 72% and 76% (mol/mol) respectively. After sampling, 11.98 g of a clear, viscous liquid remained in the flask. A vacuum of 127 mm-Hg was imposed, and temprature was maintained at 140-150° C. for an hour. Then the temperature was raised to 170° C. The liquid color turned brown within minutes. Analysis of this product indicated 29% (mol/mol) of ammonium glycolate was converted to glycolamide, 16% (mol/mol) of ammonium glycolate was converted to glycolic dimer (as combined glycolic acid dimer and ammonium glycolate dimer); glycolic acid (as combined glycolic acid and ammonium glycolate) and ammonium ion recovery were 30% and 16% (mol/mol), respectively. The combined yield of glycolic acid and glycolic acid dimer was at least approximately 22%.

EXAMPLE 65

Thermal Decomposition of Molten Ammonium Glycolate Salt Heated at 80° C. for Approximately 3 Hours Followed by Heating at 130° C. for 3 Hours Approximately 29.1 g of 25% ammonium glycolate solution was produced from enzymatic hydrolysis of glycolonitrile using *E. coli* FM5/pNM18-H9 cells (See U.S. 60/638176; hereby incorporated by reference in its entirety). The immobilized biocatalyst was decanted from the product solution. The solution was then added to a 100-mL 3-neck flask, and water was distilled off at 70-80° C. under vacuum (635-381 mm-Hg). When the weight of liquid in the flask decreased to 7.02 g, 3% (mol/mol) of ammonium glycolate was converted to glycolamide, and 12% (mol/mol) of ammonium glycolate was converted to glycolic dimer (as combined glycolic acid dimer and ammonium glycolate dimer); glycolic acid (as combined glycolic acid and ammonium glycolate) and ammonium recovery were 85% and 76%(mol/mol) respectively After sampling, 4.2 g of a clear, viscous liquid remained in the flask. A vacuum of 127 mm-Hg was imposed and the temperature was maintained at 80° C. for three hours, then at 130° C. for three hours. Analysis of this product showed 26 (mol/mol)% conversion from glycolate to glycolamide, 28% (mol/mol) conversion from glycolate to glycolic dimer (as combined glycolic acid dimer and ammonium glycolate dimer), 44% (mol/mol) glycolic acid (as combined glycolic acid and ammonium glycolate) recovery, and 27% (mol/mol) of ammonium ion remained. Approximately 1.7 wt % of glycolide was also produced. The combined yield of glycolic acid and glycolic acid dimer was at least approximately 31%.

EXAMPLE 66

Thermal Decomposition of Molten Ammonium Glycolate Salt (Lyophilized) Heated to Approximately 80-90° C. for 6 Hours Approximately 341.7 g of 40 wt % ammonium glycolate solution was frozen and lyophilized to remove water. Then 146.4 g of lyophilized ammonium glycolate was added to a flask, and heated to 80-90° C., then a vacuum of 50 mm-Hg was imposed. After six hours, no more ammonia was released. Final weight of the clear, viscous liquid was 104.4 g; 3% (mol/mol) of ammonium glycolate was converted to glycolamide, and 6% (mol/mol) of ammonium glycolate was converted to glycolic dimer (as combined glycolic acid dimer and ammonium glycolate dimer); glycolic acid (as combined glycolic acid and ammonium glycolate) and ammonium recovery were 66% (mol/mol) and 62% (mol/mol), respectively. Approximately 0.14 wt % of glycolide was also produced. The combined yield of glycolic acid and glycolic acid dimer was at least approximately 6%.

EXAMPLE 67

Conversion of Glycolic Acid to Methyl Glycolate Using Heated Methanol Vapor as Esterifying Agent and Stripping Gas The purpose of Example 67 is to illustrate the ability of the present process to convert an aqueous solution of glycolic acid into methyl glycolate using heated methanol vapor as an esterifying agent and stripping gas. The methyl glycolate product was removed from the reaction chamber and selectively isolated from the vapor product stream using a partial condenser.

$^1$H NMR Analytical Method Used in Examples 67-74

An aliquot of sample (0.40 mL) was mixed with an equal volume of $CDCl_3$ containing 0.1% TMS (tetramethylsilane), and the resulting solution analyzed by $^1$H NMR spectroscopy (500 MHz) and $^{13}$C NMR spectroscopy (125 MHz). Samples were found to contain methanol, methyl glycolate, ammonium glycolate and glycolic acid, and the $^1$H NMR chemical shifts relative to TMS for the respective methylene and/or methoxy hydrogen atoms of these compounds are listed in Table 44 (when ammonium is not present in sample) and Table 45 (when ammonium is present in the sample).

TABLE 44

| Compound | Reference Peaks | Reference Peak |
|---|---|---|
| $CH_3OH$ | $CH_3O$—, singlet, δ = 3.388 | |
| $HOCH_2C(O)OCH_3$ | $HOCH_2$—, singlet, δ = 4.176 | —$OCH_3$, singlet, δ = 3.758 |
| $HOCH_2C(O)OH$ | $HOCH_2$—, singlet, δ = 4.153 | |

When ammonium is present in the sample the glycolic acid peak shifts as follows:

TABLE 45

| Compound | Reference Peaks | Reference Peak |
|---|---|---|
| $CH_3OH$ | $CH_3O$—, singlet, δ = 3.388 | |
| $HOCH_2C(O)OCH_3$ | $HOCH_2$—, singlet, δ = 4.176 | —$OCH_3$, singlet, δ = 3.758 |
| $HOCH_2C(O)OH$ | $HOCH_2$—, singlet, δ = 4.016 | |
| $HOCH_2C(O)ONH_4$ | $HOCH_2$—, singlet, δ = 3.945 | |

The identity of the compounds identified in the table above were confirmed by individually adding methanol, methyl glycolate, ammonium glycolate, or glycolic acid to a second aliquot of a reference sample and observing an increase in the relative peak integration for the respective methylene and/or methoxy hydrogen atoms of these compounds. The molar ratios of the components of each sample were determined by integration of the portion of the $^1$H NMR spectra containing the respective methylene or methoxy H-atoms of the three chemical components.

EXAMPLE 68

Conversion of Glycolic Acid to Methyl Glycolate Using Heated Methanol Vapor as Esterifying Agent and Stripping Gas The purpose of Example 68 is to illustrate the ability of the present process to convert an aqueous solution of glycolic acid into methyl glycolate using heated methanol vapor as an esterifying agent and stripping gas. The methyl glycolate product was removed from the reaction chamber and selectively isolated from the vapor product stream using a partial condenser.

Approximately 137 g of polytetramethylene ether glycol (PTMEG, used as a high boiling point fluid; Lyondell PolyMeg® 1000, product number 9707; Lot #PEZM30B-A; Lyondell Chemical Company, Houston, Tex.; CAS#25190-06-1) was charged to the reaction chamber (300 cc autoclave). The pressure controller (loaded back-pressure regulator) was adjusted to 25 psig (~172.4 kPa). The autoclave agitator was started and set at 1000 rpm. The autoclave internal temperature was set at 200° C. and the hot condenser surface temperature was set at 130° C. Once temperatures equilibrated, methanol (Brenntag Northeast Inc., Reading, Pa.; 99.99% pure, product code 838775) flow was initiated at 10 mL/min and methanol feed temperature to the autoclave was maintained at 250° C. The conditions were maintained for 45 minutes to allow the system to come to equilibrium. Glycolic acid feed (70 wt % aqueous solution; Sigma-Aldrich, Catalog #420581) was then initiates at 1.5 mL/min and maintained for 45 minutes for a total feed of 67 mL. Methanol flow was continued an additional 20 minutes past termination of the ammonium glycolate flow. Total methanol feed was 1160 mL.

Samples were collected from the hot condenser every 5 minutes during the methanol feed. The samples were analyzed by proton nuclear magnetic resonance spectroscopy ($^1$H NMR) and found to contain methanol, methyl glycolate, and a slight amount of glycolic acid. Results for samples from the hot condenser (2-3, 2-5, and 2-7) and the stainless steel collection drum (2-drum) are presented in Table 46. The molar ratio was reported by standardizing the methyl glycolate peak (i.e. the "$CH_3$ peak") area to 1.

TABLE 46

Molar ratio of methanol, methyl glycolate, and glycolic acid in samples from the hot condenser or stainless steel collection drum. Molar ratio calculated by standardizing methyl glycolate peak area to 1.

| Collection time (minutes) | Sample Identification No. | Methanol (MeOH) | Methyl Glycolate (MeGLA) | Glycolic Acid (GLA) |
|---|---|---|---|---|
| 10-15 | 2-3 | 3.8 | 1.0 | 0.1 |
| 20-25 | 2-5 | 3.2 | 1.0 | 0.2 |
| 30-35 | 2-7 | 2.9 | 1.0 | 0.2 |
| | 2-drum | 199.5 | 1.0 | nd |

nd—not detectable

The system was cooled down and samples were recovered from various vessels and a material balance was performed. Total mass balanced within 99%. The reactor contained 138 g of viscous liquid. The methanol recovery drum contained 912 g. and the total weight of all samples was 99 grams.

EXAMPLE 69

Conversion of Ammonium Glycolate to Methyl Glycolate Using Heated Methanol Vapor as Esterifying Agent and Stripping Gas (Reactor Temperature ~200° C.; Hot Condenser ~130° C.)

The purpose of Example 69 is to show the direct conversion of an aqueous solution of ammonium glycolate to methyl glycolate using heated methanol vapor as an esterifying agent and stripping gas.

An aqueous ammonium glycolate ($NH_4$GLA) solution (ammonium glycolate "solution A") was prepared by combining 659 g of 70 wt % aqueous glycolic acid solution (Sigma-Aldrich) with 357 g of 30 wt % aqueous ammonium hydroxide solution (EMD Chemicals, Darmstadt, Germany; product no. AX1303-6).

Approximately 138 g of PTMEG was charged to the reactor (autoclave). The pressure controller was adjusted to 25 psig (~172.4 kPa). The autoclave agitator was started and set at 1000 rpm. The autoclave temperature was set at 200° C. and the hot condenser was set at 130° C. Once temperatures equilibrated, methanol flow was initiated at 10 mL/min and methanol feed temperature to the autoclave was maintained at 250° C. The conditions were maintained for 15 minutes to allow the system to come to equilibrium. Ammonium Glycolate solution A was then pumped to the reactor at a rate of 2.2 mL/min and maintained for 60 minutes for a total feed of 132 mL. Methanol flow was continued an additional 35 minutes past termination of the ammonium glycolate feed. Total methanol feed was 1110 mL.

Samples were collected from the hot condenser every 5 minutes during the ammonium glycolate feed. The first 30 minutes of samples were combined to make samples designated with an "A" and the second 30 minutes of samples were combined to make samples designated with a "B". The samples (samples "5A" and "5B") were analyzed by $^1$H NMR and found to contain methanol, methyl glycolate, and ammonium glycolate. Results are summarized in Table 47

The system was cooled down and samples were recovered from various vessels and a material balance was performed. The autoclave contained 140 g of viscous liquid. The methanol recovery drum contained 913 g and the total weight of all samples was 123 grams.

EXAMPLE 70

Conversion of Ammonium Glycolate to Methyl Glycolate Using Heated Methanol Vapor as Esterifying Agent and Stripping Gas (Reactor Temperature ~170° C.; Hot Condenser ~100° C.)

Equipment and procedures were identical to Example 69 except the reactor (autoclave) temperature was maintained at 170° C. and the hot condenser was maintained at 100° C. Ammonium glycolate solution A was fed for 60 minutes and samples were combined as described in Example 68 to prepare samples "7A" and "7B". Results are summarized in Table 47.

EXAMPLE 71

Conversion of Ammonium Glycolate to Methyl Glycolate Using Heated Methanol Vapor as Esterifying Agent and Stripping Gas (Mineral Oil as Heat Transfer Fluid; Reactor ~170° C.; Hot Condenser ~100° C.)

Equipment and procedures were identical to those described in Example 70 unless otherwise noted.

Approximately 131 g of mineral oil (MultiTherm PG-1® heat transfer fluid, MultiTherm® LLC, Malvern, Pa.) was added to the reactor. The autoclave temperature was maintained at 170° C. and the hot condenser was maintained at 100° C. Ammonium glycolate solution A was fed for 60 minutes and samples were combined like Example 69 to prepare samples "8A" and "8B". Results are summarized in Table 47.

EXAMPLE 72

Conversion of Ammonium Glycolate to Methyl Glycolate Using Heated Methanol Vapor as Esterifying Agent and Stripping Gas (Mineral Oil as Heat Transfer Fluid, Reactor ~200° C.; Hot Condenser ~130° C.)

Equipment and procedures were identical to those described in Example 69 unless otherwise noted.

Approximately 128 g of mineral oil (MultiTherm PG-1® heat transfer fluid, MultiTherm® LLC, Malvern, Pa.) was added to the reactor. The autoclave temperature was maintained at 200° C. and the hot condenser was maintained at 130° C. An ammonium glycolate solution (ammonium glycolate "solution B") was prepared by combining 75 g of glycolic acid crystals (99% glycolic acid, Sigma Aldrich Catalogue #124737) with 68.5 g of aqueous ammonium hydroxide solution (30 wt %, EMD Chemicals) and 25 g of deionized water. Ammonium glycolate solution B was fed for 60 minutes and samples were combined like Example 69 to prepare samples "9A" and "9B". Results are summarized in Table 47.

EXAMPLE 73

Conversion of Ammonium Glycolate to Methyl Glycolate Using Heated Methanol Vapor as Esterifying Agent and Stripping Gas (No High Boiling Point Fluid; Reactor ~200° C.: Hot Condenser ~130° C.)

Equipment and procedures were identical to Example 69 except no high boiling point fluid was used. Instead, the agitator was removed and 94 grams of packing material ("ProPak" ¼ inch high efficiency packing made from Hastelloy® C276, Ace Glass Inc.) was added to the reactor (autoclave). The methanol feed line was inserted through the packing so methanol addition was at the bottom of the autoclave. An ammonium glycolate solution (ammonium glycolate "solution C") was prepared by combining equal mass of 70 wt % aqueous glycolic acid solution (Sigma Aldrich) and 30 wt % aqueous ammonium hydroxide solution (EMD Chemicals) followed by minor adjustments with GLA and ammonium to achieve a pH between 7.0 and 7.5. The ammonium glycolate feed was added to the top of the packing in the reactor.

The reactor temperature was maintained at 200° C. and the hot condenser was maintained at 130° C. Ammonium glycolate solution C was fed at 2.2 mL/minute for 60 minutes and samples were combined like Example 69 to prepare samples "11A" and "11B". Results are summarized in Table 47.

EXAMPLE 74

Conversion of Ammonium Glycolate to Methyl Glycolate Using Heated Methanol Vapor as Esterifying Agent and Stripping Gas (No Heat Transfer Fluid; Reactor ~170° C.; Hot Condenser ~100° C.)

Equipment and procedures were identical to Example 73 except the autoclave temperature was maintained at 170° C. and the hot condenser was maintained at 100° C. Ammonium glycolate "solution C" was fed for 60 minutes and samples were combined like Example 69 to prepare samples "13A" and "13B". Results are summarized in Table 47.

TABLE 47

Molar ratio of methanol, methyl glycolate, ammonium glycolate, and glycolic acid in samples from the hot condenser. Molar ratio calculated by standardizing methyl glycolate peak area to 1.

| Collection Time (minutes) | Sample Identification No. | Methanol (MeOH) | Methyl Glycolate (MeGLA) | Glycolic Acid (GLA) | Ammonium Glycolate ($NH_4GLA$) |
|---|---|---|---|---|---|
| 0-30 | 5A | 17.4 | 1.0 | 0.66 | 0.19 |
| 30-60 | 5B | 6.7 | 1.0 | 0.45 | 0.09 |
| 0-30 | 7A | 26.8 | 1.0 | 0.30 | 0.15 |
| 30-60 | 7B | 8.8 | 1.0 | 0.24 | 0.13 |
| 0-30 | 8A | 11.7 | 1.0 | 0.21 | 0.15 |
| 30-60 | 8B | 52.7 | 1.0 | 0.47 | 0.51 |
| 0-25 | 9A | 12.8 | 1.0 | 0.49 | 0.15 |
| 25-50 | 9B | 6.1 | 1.0 | 0.47 | 0.17 |
| 0-30 | 11A | 70.6 | 1.0 | 1.18 | 0.24 |
| 30-60 | 11B | 26.6 | 1.0 | 0.59 | 0.16 |
| 0-30 | 13A | 27.4 | 1.0 | 0.26 | 0.17 |
| 30-60 | 13B | 17.9 | 1.0 | 0.19 | 0.17 |

What is claimed is:

1. A process for producing glycolic acid from formaldehyde and hydrogen cyanide comprising:
   (a) providing an aqueous formaldehyde feed stream that is heated to a temperature of about 90° C. to about 150° C. for a determinable period of time;
   (b) contacting the heated aqueous feed stream of (a) with hydrogen cyanide at a temperature suitable for glycolonitrile synthesis, whereby glycolonitrile is produced;
   (c) contacting the glycolonitrile of step (b) in a suitable aqueous reaction mixture with an enzyme catalyst comprising a polypeptide having nitrilase activity, said polypeptide having the amino acid sequence of SEQ ID NO:32 whereby glycolic acid is produced; and
   (d) recovering the glycolic acid produced in (c) in the form of a salt or acid.

2. The process of claim 1 wherein the glycolic acid is recovered using a recovery method selected from the group consisting of reactive solvent extraction, ion exchange, electrodialysis, polymerization, thermal decomposition, alcoholysis, and combinations thereof.

3. The process of claim 2 wherein the recovery method is selected from the group consisting of ion exchange and reactive solvent extraction.

4. The process of claim 1 wherein an amount of sodium hydroxide is added to the aqueous formaldehyde feed stream prior to heating the aqueous formaldehyde feed stream wherein the molar ratio of sodium hydroxide to formaldehyde is about 1:50 to about 1:2000.

5. The process of claim 1 wherein the molar ratio of hydrogen cyanide to formaldehyde is at least 1.01 to about 1.15:1.

6. The process of claim 1 wherein the heated aqueous formaldehyde feed stream is reacted with hydrogen cyanide at a reaction temperature of about 0° C. to about 70° C.

7. The process of claim 6 wherein the heated aqueous formaldehyde feed stream is reacted with hydrogen cyanide at a reaction temperature of about 10° C. to about 30° C.

8. The process of claim 1 wherein the aqueous formaldehyde feed stream comprises about 0.1 wt % to about 15 wt % methanol.

9. The process of claim 1 wherein the enzyme catalyst is in the form of a whole microbial cell, a permeabilized microbial cell, a microbial cell extract, partially purified enzyme, or purified enzyme.

10. The process of claim 9 wherein said whole microbial cell is a transformed microbial host cell recombinantly expressing said polypeptide.

11. The process of claim 10 wherein the transformed microbial host cell is selected from the group consisting of *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Kiebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacterla* sp., *Bacillus* sp., *Eschenchia* sp., *Pseudomonas* sp., *Rhizobium* sp., and *Streptomyces* sp.

12. The process of claim 11 wherein the transformed microbial host is *Eschenchia coli.*

13. The process of claim 12 wherein the transformed microbial host cell is an *Escherlchia coli* strain selected from the group consisting of *E. coil* MG1655 having international depository number ATCC 47076 and *E. coli* FM5 having international depository number ATCC 53911.

14. The process of any one of claims 9-13 wherein the enzyme catalyst is immobilized in or on a soluble or insoluble support.

15. The process of claim 1 wherein the concentration of ammonium glycolate produced in the aqueous reaction mixture is about 0.02 wt % to about 90 wt %.

16. The process of claim 15 wherein the concentration of ammonium glycolate produced in the aqueous reaction mixture is about 0.02 wt % to about 40 wt %.

17. The process of claim 1 wherein the glycolonitrile concentration in the aqueous reaction mixture is in the range of about 5 mM to about 1 M.

18. The process of claim 17 wherein the glycolonitrile concentration in the aqueous reaction mixture is maintained by continuous or aliquot addition.

19. The process of claim 1 wherein the pH in the aqueous reaction mixture is maintained between about 5.5 and about 7.7.

20. The process of claim 1 wherein the enzymatic conversion of glycolonitrile to glycolic acid occurs under substantially oxygen free conditions.

21. The process of claim 1 wherein the aqueous reaction mixture further comprises a stabilizer selected from the group consisting of potassium thiosulfate and sodium dithionite at a concentration of less than 5 wt %.

22. The process of claim 1, wherein said enzyme catalyst provides a catalyst productivity of at least 300 grams of glycolic acid per gram dry cell weight of enzyme catalyst.

23. The process of claim 22, wherein said enzyme catalyst provides a catalyst productivity of at least 450 grams of glycolic acid per gram dry cell weight of enzyme catalyst.

24. The process of claim 23, wherein said enzyme catalyst provides a catalyst productivity of at least 1000 grams of glycolic acid per gram dry cell weight of enzyme catalyst.

25. A process for producing glycolic acid from formaldehyde and hydrogen cyanide comprising:

(a) providing an aqueous formaldehyde feed stream that is heated to a temperature of about 90° C. to about 150° C. for a determinable period of time;

(b) contacting the heated aqueous feed stream of (a) with hydrogen cyanide at a temperature suitable for glycolonitrile synthesis, whereby glycolonitrile is produced;

(c) contacting the glycolonitrile of step (b) in a suitable aqueous reaction mixture with an enzyme catalyst comprising a polypeptide having nitrilase activity; said polypeptide having an amino acid sequence of SEQ ID NO:32, whereby glycolic acid is produced; and (d) recovering the glycolic acid produced in (c) by ion exchange; wherein said glycolic acid has a purity of at least 99.9%.

* * * * *